United States Patent [19]
Moriya et al.

[11] Patent Number: 5,804,414
[45] Date of Patent: Sep. 8, 1998

[54] METHOD OF AMPLIFYING GENES USING ARTIFICIAL TRANSPOSONS IN CORYNEFORM BACTERIA

[75] Inventors: Mika Moriya; Hiroshi Matsui; Kenzo Yokozeki; Seiko Hirano; Atsushi Hayakawa; Masako Izui; Masakazu Sugimoto, all of Kawasaki, Japan

[73] Assignee: Ajinomoto Co., Inc., Tokyo, Japan

[21] Appl. No.: 674,168

[22] Filed: Jul. 1, 1996

[30] Foreign Application Priority Data

Jun. 30, 1995 [JP] Japan .................................. 7-166541

[51] Int. Cl.⁶ ............................ C12N 1/21; C12P 13/04; C12P 21/00; C12P 21/04
[52] U.S. Cl. ...................... 435/69.1; 435/106; 435/115; 435/172.3; 435/252.32
[58] Field of Search ................... 435/172.3, 106, 435/115, 69.1, 252.32

[56] References Cited

U.S. PATENT DOCUMENTS

5,380,657  1/1995  Schaefer et al. ................. 435/172.3

FOREIGN PATENT DOCUMENTS

| | | |
|---|---|---|
| 30154/89 | 8/1989 | Australia . |
| 2037431 | 4/1991 | Canada . |
| 0 435 132 | 7/1991 | European Pat. Off. . |
| 0 445 385 | 9/1991 | European Pat. Off. . |
| 0 506 780 | 10/1992 | European Pat. Off. . |
| 0 584 375 | 3/1994 | European Pat. Off. . |
| 7-107976 | 4/1995 | Japan . |
| 7-327680 | 12/1995 | Japan . |
| WO 92/02627 | 2/1992 | WIPO . |

OTHER PUBLICATIONS

Tauch et al., Plasmid 33:168–179 (1995).
Tauch et al., Plasmid 34:119–131 (1995).
Molecular Microbiology, vol. 11, No. 4, pp. 739–746, 1994, Alain A. Vertes, et al., "Isolation and Characterization of IS31831, a Transposable Element from *Corynebacterium Glutamicum*".
Molecular Microbiology, vol. 14, No. 3, pp. 571–581, 1994, Celine Bonamy, et al., "Identification of IS1206, a *Corynebacterium Glutamicum* IS3–related Insertion Sequence and Phylogenetic Analysis".
Mol Gen Genet, vol. 245, pp. 397–405, 1994, Alain A. Vertes, et al., "Transposon Mutagenesis of Coryneform Bacteria".
FEMS Microbiology Letters, vol. 126, pp. 1–6, 1995, Wolfgang Jaeger, et al., "Isolation of Insertion Elements from Gram–Positive Brevibacterium, Corynebacterium and Rhodococcus Strains Using the *Bacillus Subtilis* sacB Gene as a Positive Selection Marker".

*Primary Examiner*—Johnny F. Railey, II
*Attorney, Agent, or Firm*—Oblon, Spivak, McClelland, Maier & Neustadt, P.C.

[57] ABSTRACT

A method of amplifying a desired gene in a chromosome of a coryneform bacterium, which comprises forming an artificial transposon in which a drug resistance gene and the desired gene are inserted into an insertion sequence of the coryneform bacterium, and introducing said artificial transposon into the coryneform bacterium. In accordance with the method of the present invention, a desired gene can be amplified in a chromosome in coryneform bacteria which are used in the industrial production of amino acids or nucleic acids.

12 Claims, 38 Drawing Sheets

METHOD OF AMPLIFYING GENES USING ARTIFICIAL TRANSPOSONS IN CORYNEFORM BACTERIA

DETAILED DESCRIPTION OF THE INVENTION

1. Field of the Invention

The present invention relates to a method of amplifying a desired gene in a chromosome of a coryneform bacterium using an artificial transposon which is transposable in the coryneform bacterium and to a coryneform bacterium obtained by this method. When the desired gene is a gene that participates in biosynthesis of amino acids or nucleic acids, amino acids or nucleic acids can be produced using the thus-obtained coryneform bacterium. A method of amplifying a desired gene in a chromosome is important in improving the breeding of coryneform bacteria which are used in the industrial production of amino acids or nucleic acids.

2. Description of the Background

Methods for improving the breeding of coryneform bacteria and efficiently producing amino acids or nucleic acids are known. A large number of breeding means are based on genetic engineering. Gene manipulation has been developed for the breeding of coryneform bacteria using plasmids or phages. Various techniques have been described including transformation using protoplasts (Katsumata et al., 1984, J. Bacteriol., 159, 306; Santamaria et al., 1985, J. Bacteriol, 161, 463), development of various vectors (Miwa et al, 1984, Agric. Biol. Chem., 48, 2901; Katsumata et al, 1984, J. Bacteriol., 159, 306; Santamaria et al, 1984, J. Gen. Microbiol., 130, 2237; Yeh et al, 1986, Gene, 47, 301; Patek et al, 1989, Appl. Microbiol. Biotechnol., 31, 65), development of a method of controlling gene expression (Tsuchiya & Morinaga, 1988, Bio/Technology, 6 , 428), and development of cosmids (Miwa et al, 1985, Gene, 39, 281).

The cloning of genes derived from coryneform bacteria was reported (Matsui et al, 1986, Nucleic Acids Res., 14, 10113; Follettie et al, 1986, J. Bacteriol, 167, 695; Mateos et al, 1987, Nucleic Acids Res., 15, 10598; Mateos et al, 1987, Nucleic Acids Res., 15, 3922; Melumbres et al, 1988, Nucleic Acids Res., 16, 9859; Matsui et al, 1988, Agric. Biol. Chem., 52, 525; Peoples et al, 1988, Mol. Microbiol., 2, 63; Eikmanns et al, 1989, Mol. Gen. Genet., 218, 330; and O'Regan, 1989, Gene, 77, 237). An increase in the yields of various amino acids was reported by Sano et al (1987, Agric. Biol. Chem., 51, 597).

Recently, transposable elements of coryneform bacteria have been reported (WO 92/02627; WO 93/18151; EP0445385; Japanese Laid-Open Patent Application (hereinafter referred to as "Japanese Kokai") No. 46,867/1994; Vertes et al, 1984, Mol. Microbiol., 11, 739; Bonamy et al, 1994, Mol. Microbiol., 14, 571; Vertes et al, 1994, Mol. Gen. Genet., 245, 397; Jagar et al, 1995, FEMS Microbiology Letters, 126, 1; and Japanese Kokai No. 107,976/1995).

A transposable element is a DNA fragment that can be transposed in a chromosome. Transposable elements are present in a broad range of organisms including procaryotes and eucaryotes. Detailed information is available for eucaryotes such as maize, drosophilae, yeasts and the like, and for procaryotes such as *Escherichia coli* and the like (Mobile DNA, American Society for Microbiology, Washington D.C. (1989)).

Transposable elements for bacteria are grouped into two types—insertion sequences and transposons. An insertion sequence is a DNA fragment which has a size of approximately from 760 to 2,000 bp, has inverted repeats of approximately from 8 to 20 bp at both ends and encodes transposase, an enzyme necessary for transposition thereinside.

A transposon is a transposable element having the inverted repeats and the transposase as well as a gene such as a drug resistance gene which does not directly participate in transposition performance. One common type of transposon has a drug resistance gene held between two insertion sequences and another has a drug resistance gene inserted in the insertion sequence.

Transposition of such insertion sequences and transposons results in the duplication of a nucleotide sequence of approximately 10 bp at a target gene site having introduced therein the insertion sequence or the transposon (Mobile Genetic Elements, Academic Press, New York, pp. 159–221 (1983)).

Transposons Tn10 and Tn5 of *Escherichia coli* and Mu phage are commonly used in chromosomal genetic engineering. It is considered that 1) the transposon is transposed into a chromosomal gene to disrupt the gene, repressing the expression of this chromosomal gene, 2) a promoter sequence is inserted into a transposon to express the chromosomal gene present in the insertion site, and 3) a foreign or self desired gene is contained in a transposon for transposition to introduce the new gene into a chromosome (Mobile DNA, American Society for Microbiology, Washington D.C., pp. 879–925 (1989)).

A transposable element which is an insertion sequence has been recently found in coryneform bacteria, but a transposable element which is a transposon having a drug resistance gene or the like is as of yet unknown. A transposon in which a kanamycin resistance gene was artificially inserted has been produced (WO93/18151; Japanese Kokai No. 107,976/1995; and Vertes et al, 1994, Mol. Gen. Genet., 245, 397) and transposed into a chromosome. The artificial transposon produced therein includes one in which a drug resistance gene is held between two insertion sequences (WO93/18151) and one in which a drug resistance gene is inserted in an insertion sequence (Japanese Kokai No. 107,976/1995; and Vertes et al, 1994, Mol. Gen. Genet., 245, 397).

Unfortunately, transposition by multi-copying such an artificial transposon is not observed nor is the increase in the number of copies satisfactory. Accordingly, a technique for amplifying genes with the use of an artificial transposon which is useful in the industries of amino acids or nucleic acids has not yet been established.

SUMMARY OF THE INVENTION

Accordingly, one object of the present invention to provide a method comprising forming an artificial transposon containing a drug resistance gene and a gene to be amplified using an insertion sequence of a coryneform bacterium as a scaffold and amplifying the desired gene in a chromosome of the coryneform bacterium.

Another object of the present invention is to provide a coryneform bacterium in which a specific gene is amplified in a chromosome.

Another object of the present invention is to provide a method for producing a substance by using a coryneform bacterium in which a specific gene is amplified in a chromosome.

In order to solve the above-mentioned problems, present inventors have variously constructed an artificial transposon-like sequence having such a structure that a drug resistance gene and a desired gene which do not participate in the transposition performance is inserted between inverted repeats at both ends of an insertion sequence derived from a chromosomal DNA of a coryneform bacterium. As a result, they have found that this transposon-like sequence (artificial transposon) is transposed with good efficiency, and that a microorganism in which many copies of the artificial transposon are transposed into its chromosome can be formed at good efficiency by selecting such mutants based on their drug resistance. These findings have led to the completion of the present invention.

The present invention comprises:

A method of introducing and amplifying a desired gene on a chromosome, which comprises forming an artificial transposition which has a structure that a drug resistance gene and a gene to be amplified are held between an inverted repeat, wherein said artificial transposon is transposable in a coryneform bacterium, introducing said artificial transposon into the coryneform bacterium, introducing said artificial transposon into the coryneform bacterium and transposing said transposon into the chromosome of the coryneform bacterium.

DETAILED DESCRIPTION OF THE PREFERRED EMBODIMENTS

Figure 1:
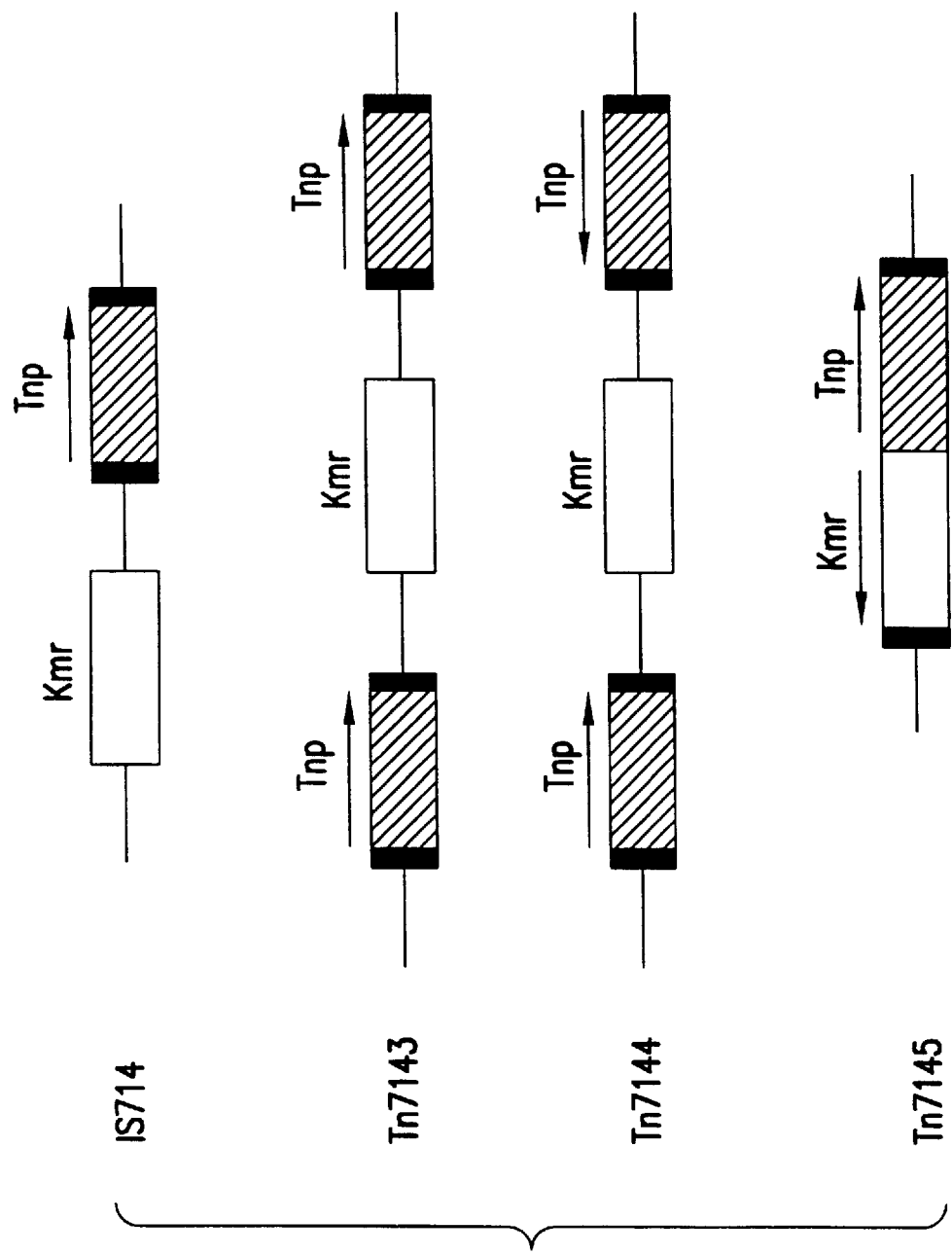
FIG. 1 is a view showing structures of various artificial transposons. Kmr represents a neomycin phosphotransferase gene (kanamycin resistance gene), and Tnp represents a transposase gene. The black-colored portion indicates an inverted repeat sequence.

The inverted repeat referred to in the present invention is preferably ones which exist on the both terminals of a transposable element isolated from a coryneform bacterium. Suitable insertion sequences include SEQ ID NOs: 1, 5 and 9 (IS714, IS719 and IS903, respectively). These sequences are described in WO93/18151.

Insertion sequence IS714 is shown in SEQ ID NO: 1 and forms an inverted repeat with SEQ ID NO: 3 at the 5' terminus of sense strand and SEQ ID NO: 4 at the 5' terminus of the reverse strand. Insertion sequence IS719 is shown in SEQ ID NO: 5 and forms an inverted repeat with SEQ ID NO: 7 at the 5' terminus of the sense strand and SEQ ID NO: 8 at the 5' terminus of the reverse strand. An inverted repeat can be formed by putting at each of the 5' terminus of the sense strand and the 5' terminus of the reverse strand one sequence selected from the group consisting of SEQ ID NO: 3, 4, 7 and 8. In addition, an inverted repeat can be formed by putting at each of the 5' terminus of the sense strand and the 5' terminus of thereverse strand two sequences each selected from a group consisting of SEQ ID NO: 3, 4, 7 and 8.

Insertion sequence IS903 shown in SEQ ID NO: 9 forms an inverted repeat with SEQ ID NO: 10 at the 5' terminus of the sense strand and SEQ ID NO: 11 at the 5' terminus of the reverse strand. An inverted repeat can be formed by putting at each of the 5' terminus of the sense strand and the 5' terminus of the reverse strand one sequence selected from the group consisting of SEQ ID NO: 10 and 11. Alternatively, an inverted repeat can be formed by putting at each of the 5' terminus of the sense strand and the 5' terminus of the reverse strand two sequences selected from the group consisting of SEQ ID NO: 10 and 11.

The inverted repeat of the present invention can be formed with any sequence other than those listed in SEQ ID NOs: 3, 4, 7, 8, 10 and 11, so long as a transposable element if formed.

Suitable drug resistance genes to be inserted into the insertion sequence includes kanamycin resistance gene, a chloramphenicol resistance gene and tetracycline resistance gene as well as genes which have resistance to various drugs, such as ampicillin resistance gene, methotrexate resistance gene and the like. A drug resistance gene which has a correlation between the degree of drug resistance and the number of copies of the drug resistance gene is preferable.

The higher the copy number of the drug resistance gene is, the greater the expression of the protein to inactivate the drug. It can be generally considered that a clone having a high copy number of the drug resistance gene can grow even under the condition of high concentration of the drug by inactivating it. Accordingly, a drug resistance gene which has a correlation between the degree of drug resistance and the number of copies of the drug resistance gene is preferable in order to select a clone having a high copy number of the gene.

Suitable genes to be amplified include genes which participate in biosynthesis of various amino acids and nucleic acids can be mentioned. Suitable genes include glutamic acid dehydrogenase gene for biosynthesis of glutamic acid, glutamine synthetase gene for biosynthesis of glutamine, aspartokinase gene (hereinafter aspartokinase is referred to as "AK", provided that a gene coding for an AK protein is hereinafter referred to as "lysC", if necessary), dihydrodipicolinate synthase gene (hereinafter dihydrodipicolinate synthase is referred to as "DDPS", provided that a gene coding for a DDPS protein is hereinafter referred to as "dapA", if necessary), dihydrodipicolinate reductase gene (hereinafter dihydrodipicolinate reductase is referred to as "DDPR", provided that a gene coding for a DDPR protein is hereinafter referred to as "dapB", if necessary), diaminopimelate decarboxylase gene (hereinafter diaminopimelate decarboxylase is referred to as "DDC", provided that a gene coding for a DDC protein is hereinafter referred to as "lysA", if necessary), and diaminopimelate dehydrogenase gene (hereinafter diaminopimelate dehydrogenase is referred to as "DDH", provided that the gene coding for a DDH protein hereinafter referred to as "ddh", if necessary) for biosynthesis of lysine, homoserine dehydrogenase gene for biosynthesis of threonine, acetohydroxy acid synthetase gene for biosynthesis of isoleucine or valine, 2-isopropylmalic acid synthetase gene for biosynthesis of leucine, glutamic acid kinase gene for biosynthesis of proline or arginine, phosphoribosyl-ATP pyrophosphorylase gene for biosynthesis of histidine, deoxyarabinohepturonic acid phosphate (DAHP) synthetase gene for biosynthesis of aromatic amino acids such as tryptophan, tyrosine and phenylalanine, and phosphoribosylpyrophosphate (PRPP) amidotransferase gene, inosine guanosine kinase gene, inosinic acid (IMP) dehydrogenase gene and guanylic acid (GMP) synthetase gene for biosynthesis of nucleic acids such as inosinic acid and guanylic acid. The DNA sequences of the above-mentioned enzymes are available through Genbank and EMBL databases.

Alternatively, genes coding for physiologically active proteins such as interleukin 2, interleukin 6 and the like can also be used. The DNA sequence of IL-2 is disclosed in Tanighuchi et al, Nature, 302, 305 (1983) and that of IK-6 in Hirano et al, Nature, 324, 73 (1986).

Suitable coryneform bacteria in accordance with the present invention include, as described in Bergey's Manual of Determinative Bacteriology, 8th ed., p. 599 (1974), aerobic Gram-positive rod-shaped, bacteria which are classified to the genus Corynebacterium, bacteria which were once classified to the genus Brevibacterium but now are classified to the genus Corynebacterium (Int. J. Syst. Bacteriol., 41, 255 (1981)), bacterium of the genus Brevibacterium, and bacteria of the genus Microbacterium.

Generally, the following microorganisms which are known as L-glutamic acid-producing bacteria are useful in accordance with the present invention:
Corynebacterium acetoacidophilum
Corynebacterium acetoglutamicum
Corynebacterium callunae
Corynebacterium glutamicum
Corynebacterium lilium (Corynebacterium glutamicum)
Corynebacterium melassecola
Brevibacterium divaricatum (Corynebacterium glutamicum)
Brevibacterium flavum (Corynebacterium glutamicum)
Brevibacterium immariophilum
Brevibacterium lactofermentum (Corynebacterium glutamicum)
Brevibacterium roseum
Brevibacterium saccharolyticum
Brevibacterium thiogenitalis
Brevibacterium ammoniagenes (Corynebacterium ammoniagenes)
Microbacterium ammoniaphilum
Corynebacterium thermoaminogenes The following wild strains and mutant strains derived therefrom are preferred:
Corynebacterium acetoacidophilum ATCC 13870
Corynebacterium acetoglutamicum ATCC 15806
Corynebacterium callunae ATCC 15991
Corynebacterium glutamicum ATCC 13020
Corynebacterium lilium (Corynebacterium glutamicum) ATCC 15990
Corynebacterium melassecola ATCC 17965
Brevibacterium divaricatum (Corynebacterium glutamicum) ATCC 14020
Brevibacterium flavum (Corynebacterium glutamicum) ATCC 14067
Brevibacterium immariophilum ATCC 14068
Brevibacterium lactofermentum (Corynebacterium glutamicum) ATCC 13869
Brevibacterium roseum ATCC 13825
Brevibacterium saccharolyticum ATCC 14066
Brevibacterium thiogenitalis ATCC 19240
Brevibacterium ammoniagenes (Corynebacterium ammoniagenes) ATCC 6871
Microbacterium ammoniaphilum ATCC 15354
Corynebacterium thermoaminogenes AJ 12340 (FERM BP-1539)

The artificial transposon of the present invention comprises (i) a drug resistance gene and (ii) a desired gene which are both held between (iii) an inverted repeat. The artificial transposon has the ability to transpose in a coryneform bacterium as determined in Examples 1 and 8.

The transposition system of the present invention also contains a transposase. Suitable transposases in accordance with the present invention have, for example, an amino acid sequence of SEQ ID NOs: 2 or 6. In addition, these transposases can also contain deletions, insertions, additions, substitutions or inversions of one or more amino acid residues so long as it has a transposase activity. Transposase activity can be determined by a transposition frequency. It is enough for a mutated transposase if it maintains the ability to catalyze transposition.

The transposase gene of the present invention has, for example, a nucleic acid sequence from the 130 to the 1437 position of SEQ ID NO: 1 or a sequence from the 130 to the 1437 position of SEQ ID NO: 5. However the transposase gene can also be one of these sequences containing a deletion, an insertion, an addition, a substitution or a inversion of one or more amino acid residues as long as the gene product has a transposase activity.

The transposase gene can be located inside the artificial transposon on the present invention. That is, the transposon gene can also be held between the inverted repeat—so long as it is placed at a position which does not interfere with the functioning of the drug resistance gene and the desired gene. The transposase gene can be located inside the artificial transposon as long as the transposase gene, the drug resistance gene and the desired gene do function. These genes do not have to retain their full activity, but you cannot figure out how much activity must be retained.

Alternatively, the transposase gene can be placed outside the artificial transposon of the present invention. In this case, the transposase gene can either be carried on the same plasmid having the artificial transposon or on a second plasmid (i.e., a plasmid other than the one having the artificial transposon). The transposon gene can also exist on a chromosome.

The artificial transposon of the present invention can be easily constructed using a transposable element as the starting material. In the present invention, any insertion sequence can be used so long as it is present in the chromosome of the above-mentioned coryneform bacteria, has a size of approximately from 760 to 2,000 bp, has inverted repeats of approximately from 8 to 20 bp and encodes therein a transposase necessary for transposition. Such an insertion sequence can be obtained according to the method disclosed in WO93/18151.

That is, a DNA fragment containing an insertion sequence can be obtained by 1) introducing plasmid pEC701 into a coryneform bacterium for transformation, 2) selecting the strain transformed with pEC701 using kanamycin resistance as a marker, 3) spreading the coryneform bacterium containing plasmid pEC701 on an agar plate containing isopropyl-β-thiogalactoside (IPTG) and selecting the thus-grown strain, 4) analyzing the regulatory gene region or the structural gene region of the chloramphenicol acetyl transferase gene in the plasmid contained in the selected strain, and 5) finding the sequence inserted in this gene.

Alternatively, the above-mentioned DNA fragment can be obtained by 1) introducing plasmid pEC901 into a coryneform bacterium for transformation, 2) selecting the strain transformed with pEC901 using kanamycin resistance as a marker, 3) incubating the coryneform bacterium containing pEC901 at 30° C. and selecting the strain that expresses chloramphenicol resistance even at 30° C., 4) analyzing the cI repressor gene of the plasmid contained in the selected strain, and 5) finding the sequence inserted in this gene.

Preferred insertion sequences of the coryneform bacterium includes three types of insertion sequences represented by SEQ ID NOs: 1, 5 and 9, namely IS714, IS719 and IS903. These nucleotide sequences are not necessarily the only ones. An insertion sequence including an inverted repeat sequence in which a part of bases are replaced with other bases or deleted or a new sequence is inserted or added can be used in the construction of the artificial transposon so long as it serves as an insertion sequence.

A variety of artificial transposons can be constructed on the basis of these insertion sequences. The structures of some of these artificial transposons are shown in FIG. 1. Of these, the artificial transposon which is used in the present invention has a structure where the drug resistance gene and the gene to be amplified are inserted in the insertion sequence.

In IS714, shown in the SEQ ID NO: 1, a restriction enzyme Nhe I site is at position 37 to 42. This position is suitable for inserting the drug resistance gene and the gene to be amplified, since the insertion at the position does not interfere the functions of the inverted repeat and transposase.

In IS719, shown in SEQ ID NO: 5, a restriction enzyme Nhe I site is at position 37 to 42. This position is suitable for inserting a drug resistance gene and a desired gene to be amplified, since the insertion at the position does not interfere the functions of the inverted repeat and transposase.

In IS903, shown in SEQ ID NO: 9, a restriction enzyme Xcm I site is at position 34 to 48. This position is suitable for inserting a drug resistance gene and a desired gene to be amplified, since the insertion at the position does not interfere the functions of the inverted repeat and transposase.

The artificial transposons on the present invention can be constructed by inserting into the above insertion sequences a gene which is resistant to a drug such as kanamycin (neomycin), chloramphenicol or tetracycline. The construction of an artificial transposons in accordance with the present invention is described below. In particular, the insertion sequence IS714 is modified to contain a drug resistance gene and a gene useful for production of amino acids or nucleic acids (e.g. aspartokinase). The nucleotide sequence of IS714 is shown in SEQ ID NO: 1.

(1) Construction of an artificial transposon containing a kanamycin resistance gene Plasmid pEC701-IS14 having a sequence of IS714 which is an insertion sequence of *Brevibacterium lactofermentum* AJ12036 (FERM BP-734) which is a wild strain of a coryneform bacterium (refer to WO93/18151) is cleaved with restriction endonucleases Pvu II and Eco RI to obtain a fragment of 1.6 kb containing IS714. Meanwhile, a fragment containing IS714 is inserted into a restriction endonuclease Sal I site of plasmid pHSC4 having a temperature-sensitive replication origin which is derived from a coryneform bacterium (refer to Japanese Kokai No. 7,491/1993) to construct plasmid pHIS714.

Figure 2:
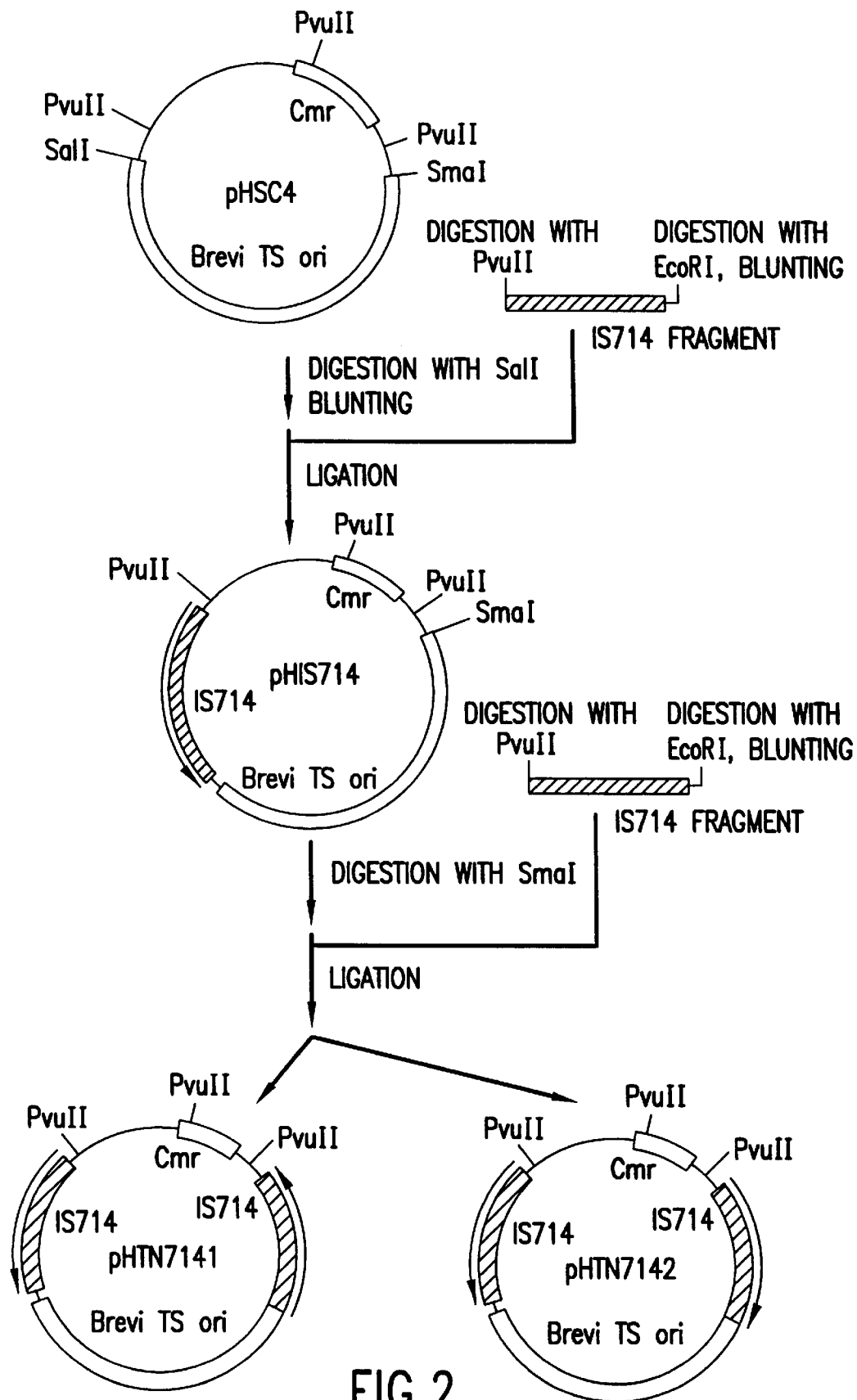
FIG. 2 is a view showing construction of the plasmids pHTN7141 and pHTN7142 each containing the artificial transposon.

The above-obtained fragment of 1.6 kb containing IS714 is further inserted in the Sma I site of pHIS714. Thus, plasmid pHTN7141 and pHTN7142 containing the IS714 fragments in opposite directions are constructed as shown in FIG. 2.

Figure 3:
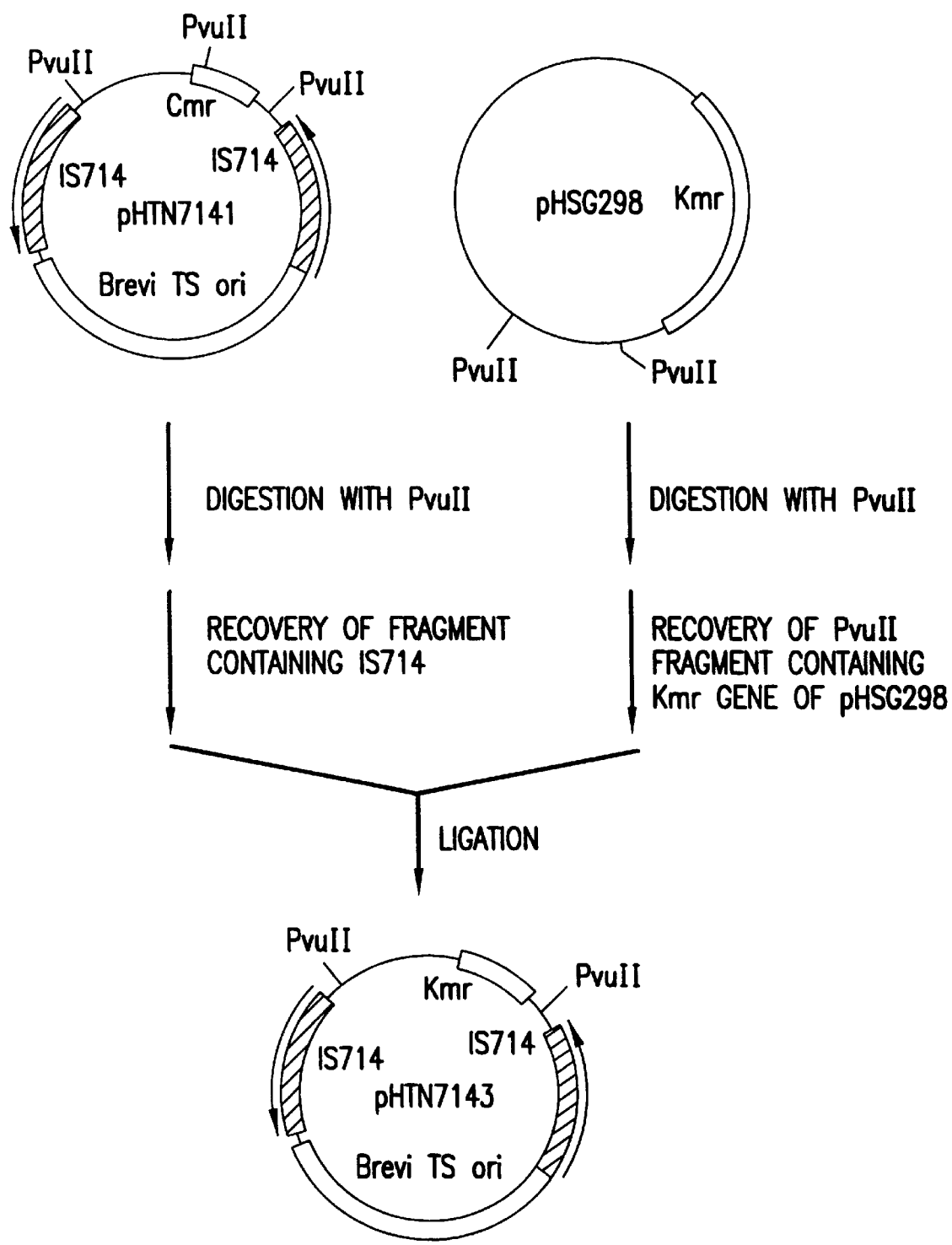
FIG. 3 is a view showing construction of the plasmid pHTN7143 containing the artificial transposon.

Then, pHTN7141 and pHTN7142 are cleaved with restriction endonuclease Pvu II, making it possible to cut out a fragment containing two sequences of IS714 and the sequence of the temperature-sensitive replication origin of pHSC4. Meanwhile, plasmid vector pHSG298 (made by Takara Shuzo) has also two restriction endonuclease Pvu II sites. A fragment of 2.3 kb containing a neomycin phosphotransferase gene (kanamycin resistance gene) can be obtained by cleaving this plasmid vector with restriction endonuclease Pvu II. pHTN7141 and pHSG298 are cleaved with restriction endonuclease Pvu II, and the resulting fragments are then ligated to transform *Brevibacterium lactofermentum* AJ12036. Plasmid pHTN7143 is obtained from the strain which has kanamycin resistance as shown in FIG. 3.

Figure 4:
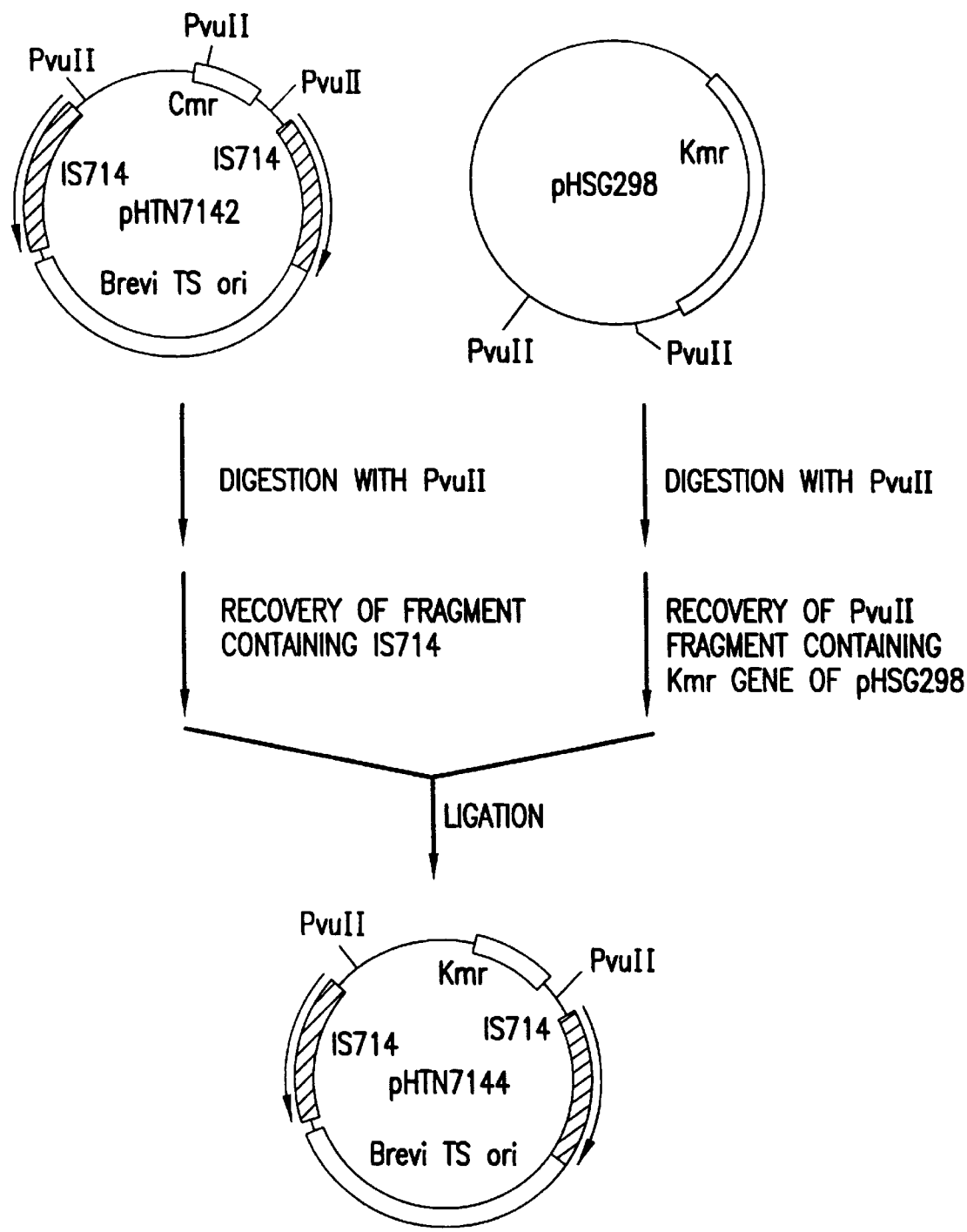
FIG. 4 is a view showing construction of the plasmid pHTN7144 containing the artificial transposon.
Figure 5:
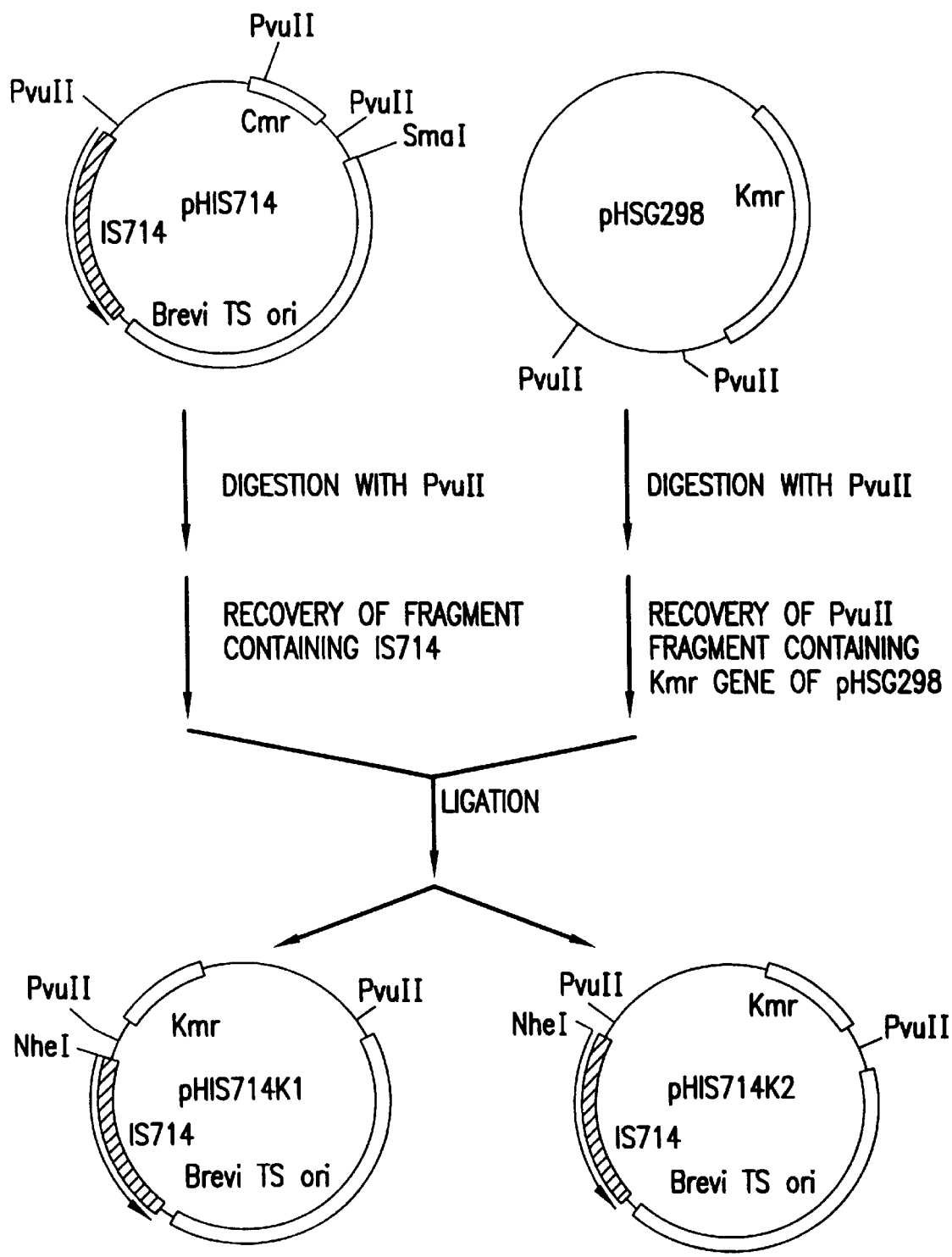
FIG. 5 is a view showing construction of the plasmids pHIS714K1 and pHIS714K2.

Plasmid pHTN7144 is obtained from plasmid pHTN7142 and pHSG298 in the above-mentioned manner as shown in FIG. 4. pHTN7143 and pHTN7144 have a structure that the neomycin phosphotransferase gene is held between two sequences of IS714. Plasmids pHIS714K1 and pHIS714K2 are constructed from plasmid pHIS714 and pHSG298 as control plasmids in the above-mentioned manner as shown in FIG. 5. In pHIS714K1 and pHIS714K2, the directions of the inserted fragments each containing the neomycin phosphotransferase gene are opposite to each other.

Figure 6:
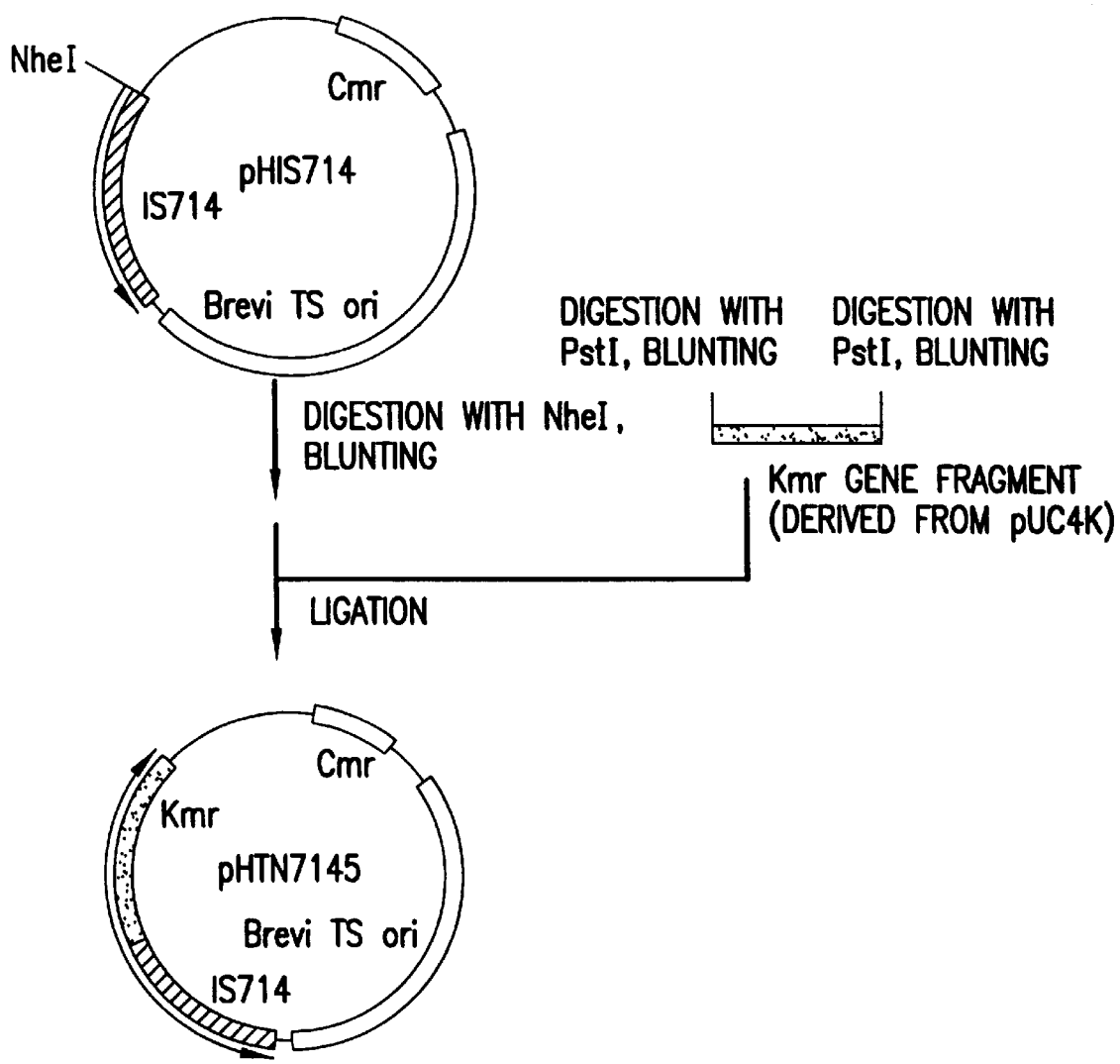
FIG. 6 is a view showing construction of the plasmid pHTN7145 containing the artificial transposon.

In order to minimize the artificial transposon, an artificial transposon is constructed in which a neomycin phosphotransferase gene is inserted into one IS714. In IS714, a restriction endonuclease Nhe I site is present in a position where the transposase function is not impaired. Plasmid pHIS714 is cleaved with restriction endonuclease Nhe I, and the ends thereof are blunted. On the other hand, a neomycin phosphotransferase gene region is cut out from plasmid pUC4K (made by Pharmacia Biotech) with restriction endonuclease Pst I, and the ends thereof are blunted. Both fragments are ligated to obtain desired plasmid pHTN7145 as shown in FIG. 6.

(2) Construction of an artificial transposon containing a chloramphenicol resistance gene A fragment of approximately 1.1 kb containing a chloramphenicol acetyltransferase gene can be obtained by cleaving plasmid vector pHSG398 (made by Takara Shuzo) with restriction endonuclease Acc II. Then, this Acc II fragment is inserted into a Sma I site of pUC18 (made by Takara Shuzo), and the thus-obtained plasmid is cloned. The desired clone is selected to obtain plasmid pUC18-CM.

Figure 7:
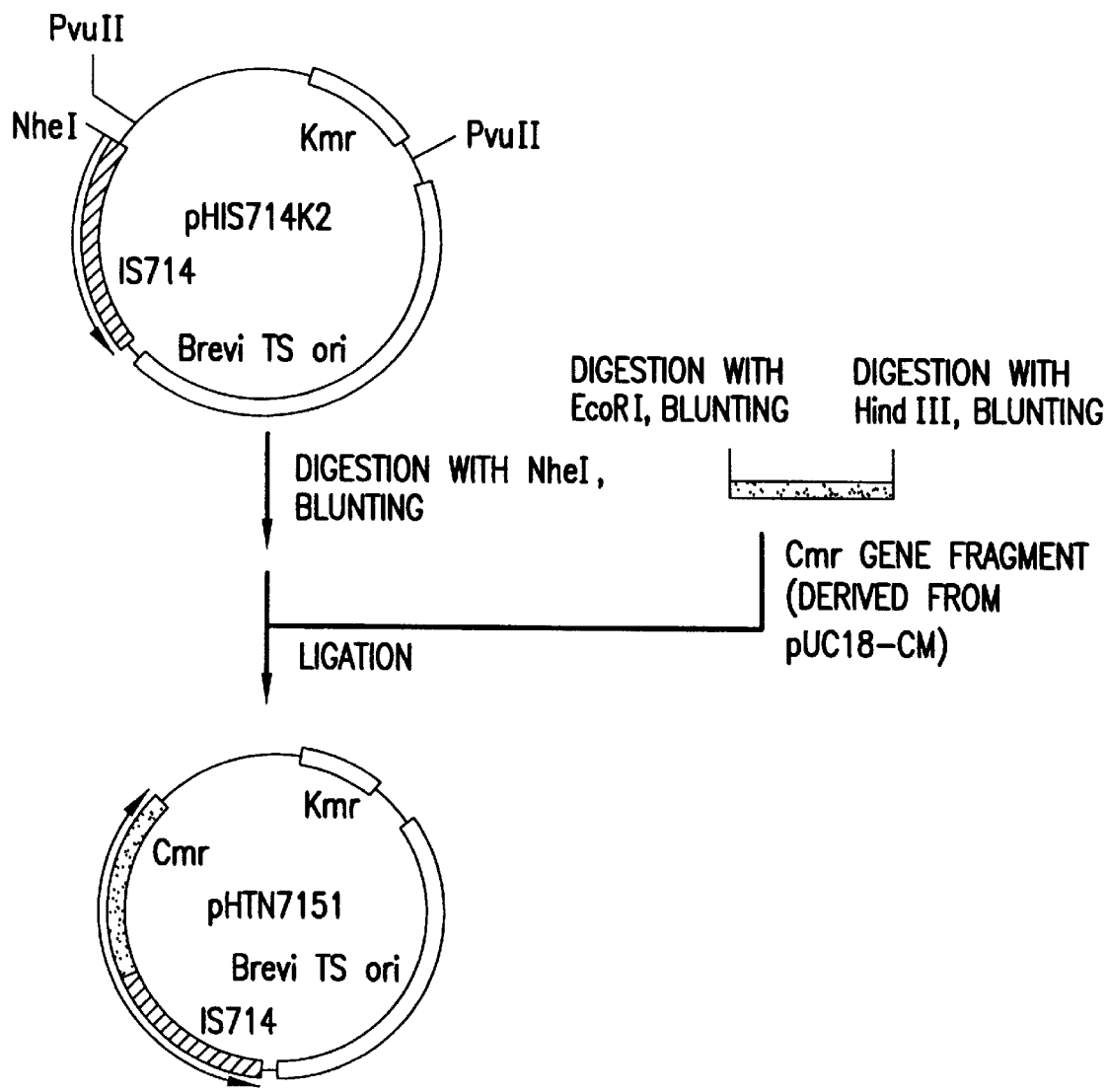
FIG. 7 is a view showing construction of the plasmid pHTN7151 containing the artificial transposon.

Further, in the above-constructed pHIS714K2, the restriction endonuclease Nhe I site of IS714 located in the position which does not impair the transposase function is blunted. A fragment of approximately 1.1 kb containing a chloramphenicol acetyltransferase gene which is cut out from pUC18-CM with Eco RI and Hind III is ligated with this restriction endonuclease Nhe I blunt site of pHIS714K2 to transform *Escherichia coli*, and the clone having inserted therein the chloramphenicol acetyltransferase gene fragment is selected. The desired plasmid pHTN7151 can be obtained from the resulting clone as shown in FIG. 7.

Figure 8:
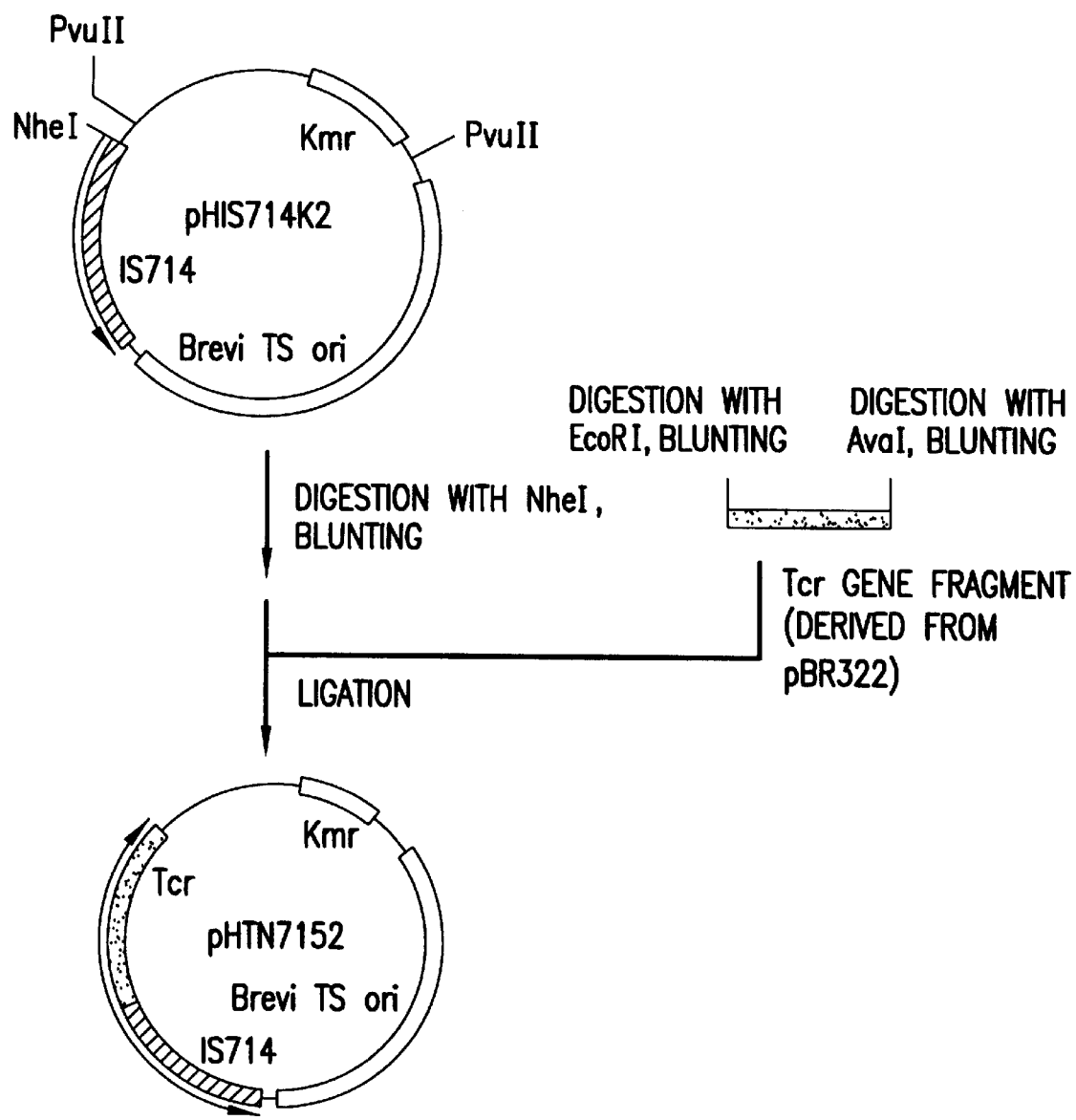
FIG. 8 is a view showing construction of the plasmid pHTN7152 containing the artificial transposon.

(3) Construction of an artificial transposon containing a tetracycline resistance gene A fragment of approximately 1.4 kb containing a tetracycline resistance gene can be obtained by cleaving plasmid vector pBR322 (made by Takara Shuzo) with restriction endonucleases Eco RI and Ava I. In the above-constructed pHIS714K2, the restriction endonuclease Nhe I site of IS714 located in the position which does not impair the transposase function is blunted. The above-formed DNA fragment is ligated with this restriction endonuclease Nhe I blunt site to transform *Escherichia coli*, and the clone having inserted therein the tetracycline resistance gene fragment is selected. Desired plasmid pHTN7152 can be obtained from the resulting clone as shown in FIG. 8.

(4) Insertion of an aspartokinase gene which is one of lysine biosynthesis genes into the artificial transposon containing the tetracycline resistance gene.

Since pHTN7152 constructed in FIG. 8 has no good restriction endonuclease site in which to insert an aspartokinase gene, pHTN7156 in which an insertion site is newly introduced is constructed as follows. A fragment of approximately 1.4 kb containing a tetracycline resistance gene can be obtained by cleaving plasmid vector pBR322 (made by Takara Shuzo) with restriction endonucleases Eco RI and Ava I. This fragment is ligated with a fragment obtained by cleaving plasmid vector pHY300PLK (made by Takara Shuzo) with restriction endonuclease Sma I to transform *Escherichia coli*, and the clone having inserted therein the tetracycline resistance gene fragment is selected. Plasmid pHY300-TC is obtained from the resulting clone.

Figure 9A:
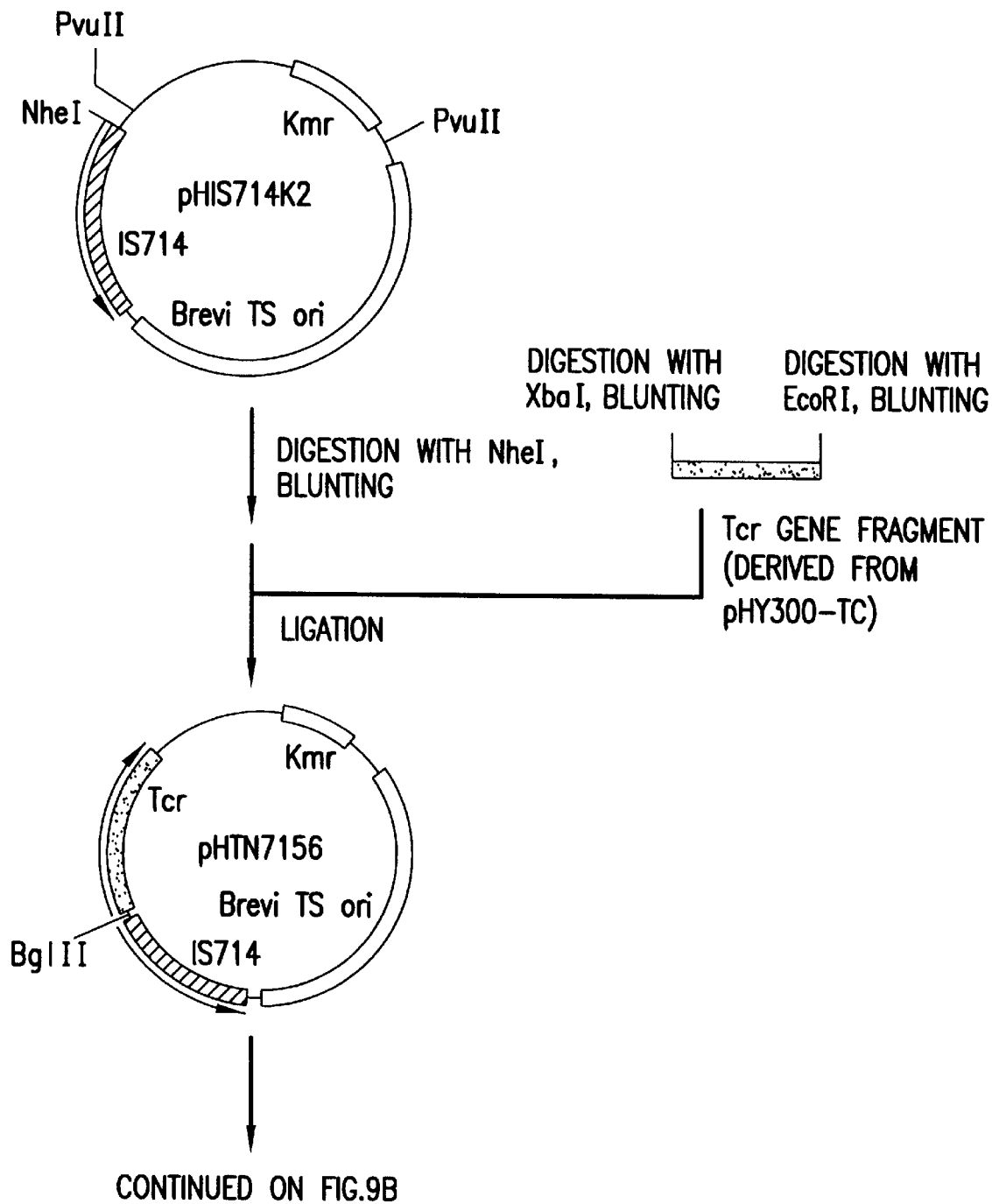
FIG. 9 is a view showing construction of the plasmid pHTN7156-C containing the artificial transposon.

Further, in the above-constructed pHIS714K2, the restriction endonuclease Nhe I site of IS714 located in the position which does not impair the transposase function is blunted. A fragment containing a tetracycline resistance gene which is obtained by cleaving pHY300-TC with restriction endonucleases Eco RI and Xba I is ligated with this restriction endonuclease Nhe I blunt site to transform *Escherichia coli*, and the clone having inserted therein the tetracycline resistance gene fragment is selected. Desired plasmid pHTN7156 is obtained from the resulting clone as shown in FIG. 9.

Subsequently, an aspartokinase gene which is one of lysine biosynthesis genes is inserted into plasmid pHTN7156 as follows.

Plasmid p399AK9B which contains an aspartokinase gene, which is derived from a lysine-producing mutant of *Brevibacterium lactofermentum*, a coryneform bacterium, and which is desensitized to concerted inhibition of lysine and threonine (refer to WO94/25605) is cleaved with restriction endonuclease Bam HI, and is self-ligated to construct pHSG399AK from which a replication origin that functions in the coryneform bacterium is removed. This pHSG399AK is cleaved with restriction endonucleases Eco RI and Sph I to obtain an aspartokinase gene fragment of approximately 1.7 kb. This fragment is inserted into the restriction endonuclease Bgl II blunt site of plasmid pHTN7156 having the artificial transposon containing the tetracycline resistance gene to construct plasmid pHTN7156-C as shown in FIG. 9.

(5) Construction of an artificial transposon containing a tetracycline resistance gene and no transposase in a transposon unit Plasmid pHIS714 is cleaved with restriction endonucleases Nhe I and Xba I to obtain a fragment containing a gene encoding a transposase. This DNA fragment is introduced into an Xba I site of plasmid vector pUC19 to construct plasmid TnpL/pUC19.

Further, TnpL/pUC19 is cleaved with restriction endonucleases Mro I and Xba I to delete a sequence including a termination codon of IS714 and a 3'-side inverted repeat (IR). A synthetic double-stranded DNA which is designed to reintroduce the terminal codon is inserted into the above-cleaved portion through ligation. In this manner, a transposase gene which is not held between an inverted repeat is obtained.

Figure 10A:
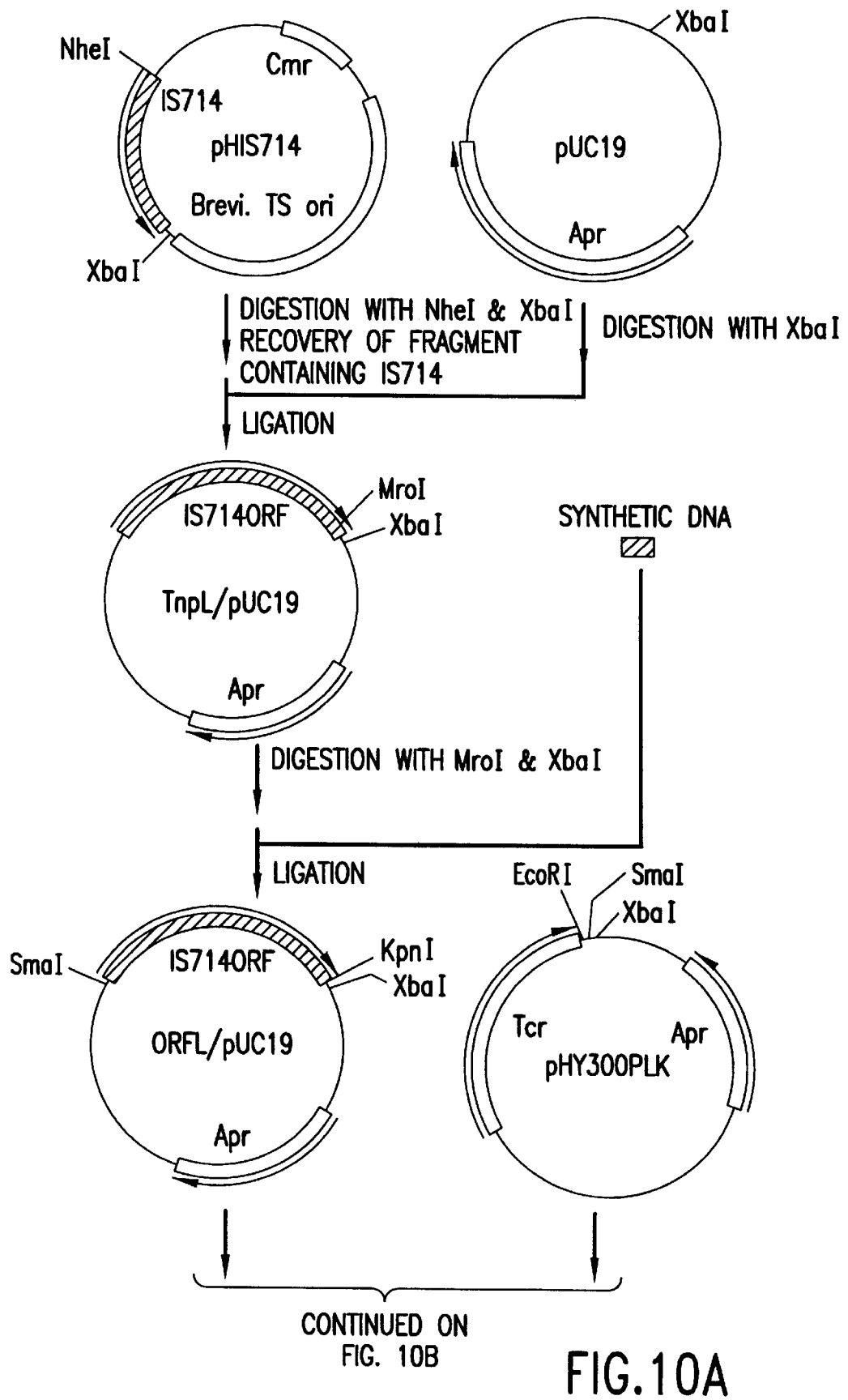
FIG. 10 is a view showing construction of the plasmid pORF1.

Subsequently, this ORFL/pUC19 is cleaved with restriction endonucleases Sma I and Xba I to obtain a gene fragment of approximately 1.5 kb containing the transposase. This transposase gene fragment is inserted into a portion of plasmid vector pHY300PLK obtained by removing a sequence between Sma I and Xba I sites thereof, and is then cut with restriction endonucleases Eco RI and Kpn I. The Eco RI and Kpn I fragment is end blunted. Meanwhile, plasmid vector pHSG398 is partially digested with restriction endonuclease Pvu II to delete a fragment containing a multi-cloning site and ligated to the above-obtained transposase gene fragment. Thus plasmid pORF1 can be constructed (FIG. 10).

On the other hand, the Nhe I-Xba I cleavage fragment of plasmid pHIS714 which contains a transposase gene is obtained, end-blunted, and transduced into the end-blunted Pst I site of plasmid vector pUC19 to construct plasmid Tnp (Pst)/pUC19.

The transposase gene of this Tnp(Pst)/pUC19 is subjected to the partial base substitution using a U. S. E. Mutagenesis Kit (made by Pharmacia Biotech). The base substituted is G which is the 288th base in the sequence of IS714. This base G is replaced with C. This base-substituted plasmid is designated as Tnp(Pst)M/pUC19. The structure of Tnp(Pst) M/pUC19 is shown in FIG. 11. indicates the introduced mutation.

The transposition of a transposable element is controlled by a variety of systems. Suitable controls include the followings (Mobile DNA, American Society for Microbiology, Washington D.C. (1989)).

1) An inhibitor gene or a repressor gene of a transposase is located next to a transposase gene inside a transposable element (e.g. Tn 3).
2) Two ORF exist in one frame. The one closer to the 3' terminal encodes. Translational frameshift between the two ORF takes place at a low frequency to make the two ORF translated throughout, which express a transposase (e.g. IS1).
3) In an ORF encoding a transposase exists another translational initiation codon (ATG, GTG) and translation starts from the codon to express an inhibitor (e.g. Tn5 (IS50)).

Meanwhile, in IS714 exists one ORF which corresponds to almost the entire length of IS714 and no other ORF is found. This indicates the possibility that IS714 has an ORF encoding a transposase like Tn5 and that an inhibitor is translated from another initiation codon in the ORF. Result of searching a promoter like sequence reveals a possibility that the sequence GTG from the 286 to the 288 is the initiation codon of an inhibitor. The mutation introduced on plasmid Tnp(Pst)M/pUC19 is designed not to start the translation of the inhibitor.

The sequence between restriction endonuclease Sma I and Nae I sites present in the transposase first half gene is deleted from pORF1. The transposase first half gene fragment obtained by cleaving Tnp(Pst)M/pUC19 with restriction endonucleases Sma I and Nae I is inserted into the above-deleted portion through ligation to construct pORF2.

The sequence between the Sma I and Xba I sites is deleted from pORF2, and the resulting fragment is end-blunted. A DNA fragment containing a tryptophan operon attenuator is obtained by cleaving pBSF2-SD7 with restriction endonucleases Nae I and Hind III, and is then end-blunted. The former fragment is ligated with the latter fragment. The thus-constructed plasmid is designated pORF3.

pORF3 is cleaved with restriction endonucleases Sal I and Bpu 1102I to delete the transposase first half gene fragment. The transposase first half gene fragment obtained by cleaving Tnp(Pst)/pUC19 with restriction endonucleases Sal I and Blu 1102I is inserted into the above-deleted portion by ligation to construct pORF4 as shown in FIG. 11.

TnpL/pUC19 is cleaved with Sac I, and is then digested with BAL 31 nuclease at 30° C. for 20 minutes to delete a sequence near the initiation codon of the transposase gene from the upstream side. After that, the transposase gene fragment is cut out using the Sph I site, and is ligated with pHSG398 which is cleaved with Sma I and Sph I. The thus-constructed plasmid is designated delTnp5/398.

Figure 12A:
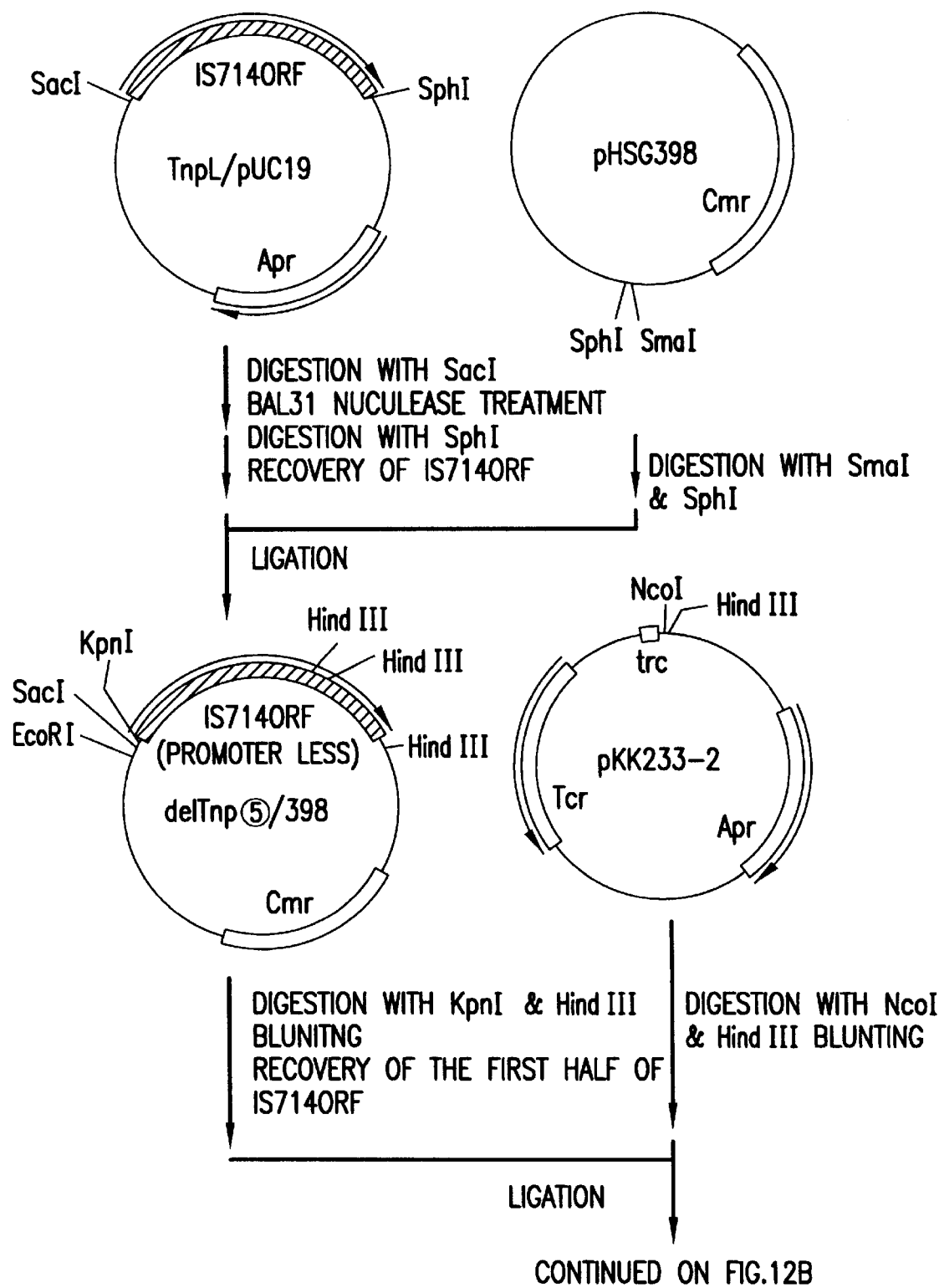
FIG. 12 is a view showing construction of the plasmid pORF7.

This delTnp5/398 is cleaved with restriction endonucleases Knp I and Hind III, and the resulting transposase first half gene fragment is end-blunted. Then, plasmid vector pKK233-2 (made by Pharmacia Biotech) is cleaved with Nco I and Hind III, and is end-blunted. The former fragment is ligated with the latter fragment to construct pTrc-ORF.

pTrc-ORF is cleaved with Ssp I and Bpu 1102I to form a fragment containing Trc promoter and the transposase first half gene. pORF3 is cleaved with Xba I, end-blunted, and further cleaved with Bpu 1102I to delete the transposase first half gene fragment. The above-formed fragment is ligated with this deleted pORF3 to construct pORF7 as shown in FIG. 12.

The transposase first half gene fragment obtained by cleaving delTnp5/39 with restriction endonucleases Kpn I and Hind III is cloned between the KpnI and Hind III sites of plasmid vector pUC18. The portion between the Bsm I and Nae I sites of this plasmid delTnp5/18 is deleted, and the fragment is ligated with the transposase first half gene fragment obtained by cleaving Tnp(Pst)M/pUC19 with restriction endonucleases Bsm I and Nae I to construct delTnp5M/18.

Figure 13A:
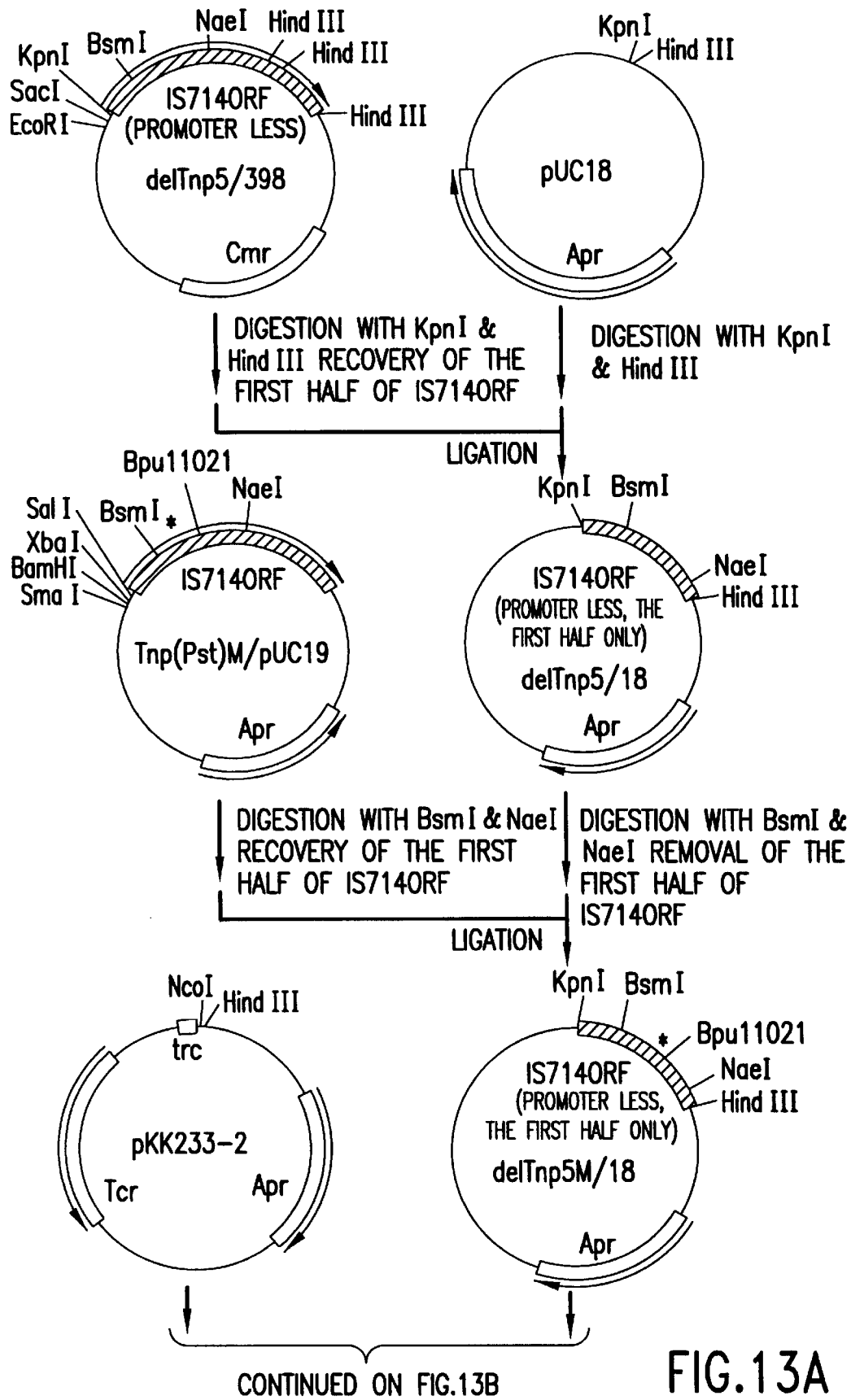
FIG. 13 is a view showing construction of the plasmid pORF8.

This delTnp5M/18 is cleaved with Kpn I and Hind III, and the resulting transposase first half gene fragment is end-blunted. pKK233-2 is cleaved with Nco I and Hind III, and the resulting fragment is end-blunted. These fragments are ligated with each other to construct pTrc-TnpM.

pORF8 is constructed from pTrc-TnpM and ORF3 by the same method of constructing pORF7 from pTrc-Tnp (FIG. 13). Plasmids for being introduced into a coryneform bacterium are constructed using the above-mentioned plasmids pORF3, pORF4, pORF7 and pORF8. The construction of pORF41 from pORF3 is described below.

First, pHIS714 is cleaved with Nhe I and Sac II to delete the major part of the transposase gene. A double-stranded synthetic DNA designed to introduce a cloning site is inserted into the above-deleted portion to construct pHTN7160.

pHTN7160 is cleaved with restriction endonuclease Kpn I, end-blunted, and then cleaved again with Bgl I to obtain a fragment containing inverted repeats (IR) on both sides of IS714 and a temperature-sensitive replication origin that functions within a coryneform bacterium.

pORF3 is cleaved with restriction endonuclease Ear I, end-blunted, and then cleaved again with Bgl I. The above-mentioned fragment of pHTN7160 is inserted therein to construct pORF41-pre.

Figure 14A:
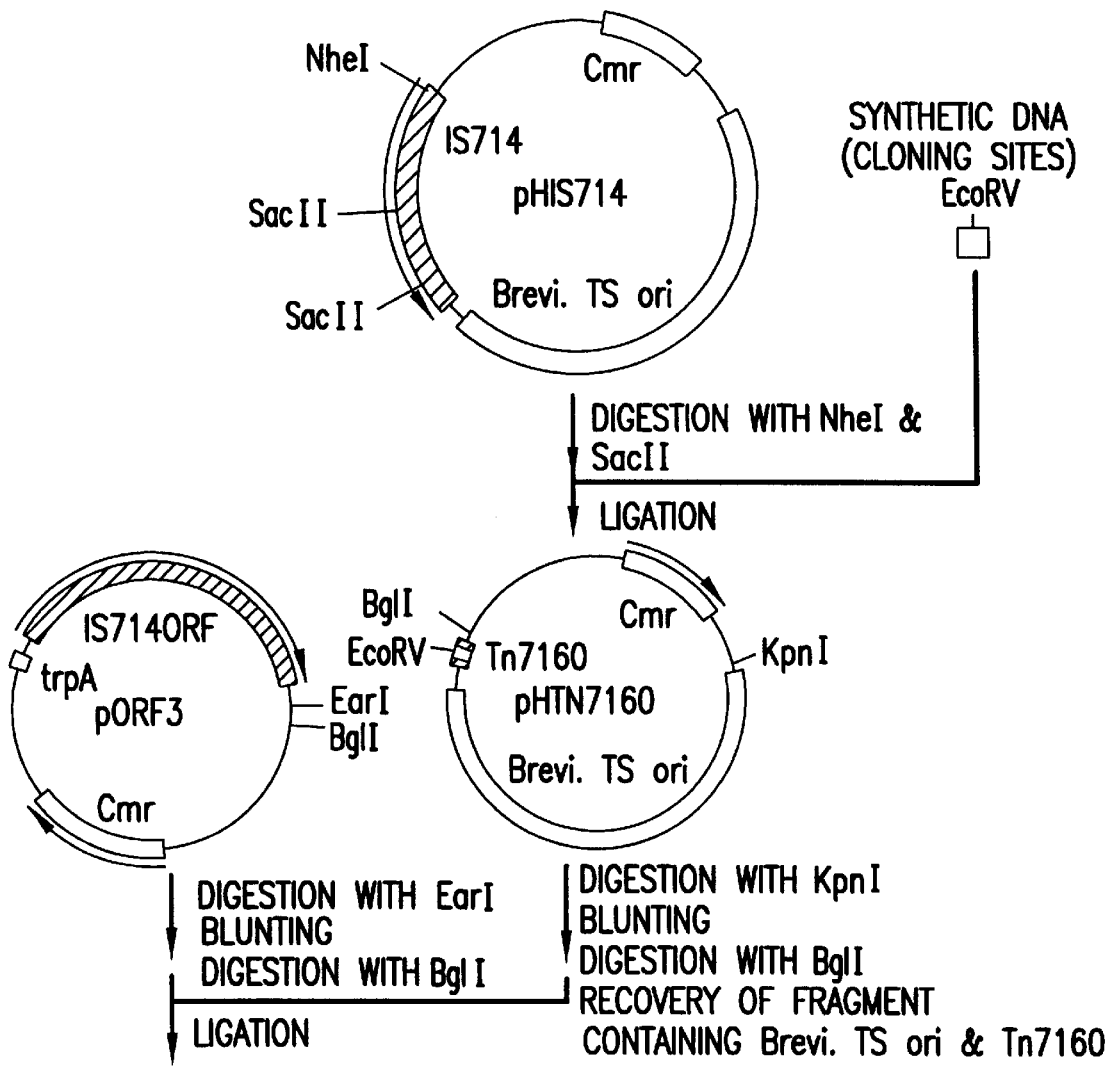
FIG. 14 is a view showing construction of the plasmid pORF41 containing the transposon unit.

Then, pORF41-pre is cleaved with Eco RV which is located between IRs at the both terminals of IS714. An Eco RI-Ava I fragment which contains a Tc resistance gene of pBR322 is end-blunted and ligated with the Eco RV-cleaved fragment to construct pORF41 as shown in FIG. 14.

The above-mentioned method is repeated to construct pORF31 from pORF4 through pORF31-pre, pORF71 from pORF7 through pORF71-pre, and pORF81 from pORF8 through pORF81-pre, respectively. pORF3 is cleaved with Xba I and Ear I, end-blunted, and self-ligated to construct pORFC0 containing no transposase gene (FIG. 15). pORFC2 is constructed from pORFC0 through pORFC2-pre in the same manner as in constructing pORF41 form pORF3. These finally constructed plasmids have the structural gene of the transposase, the Cm resistance gene, the replication origin that functions within E. coli, the temperature-sensitive replication origin that functions within a coryneform bacterium and the Tc resistance gene held between IRs of IS714, provided pORFC2 has no structural gene of the transposase.

Figure 16:
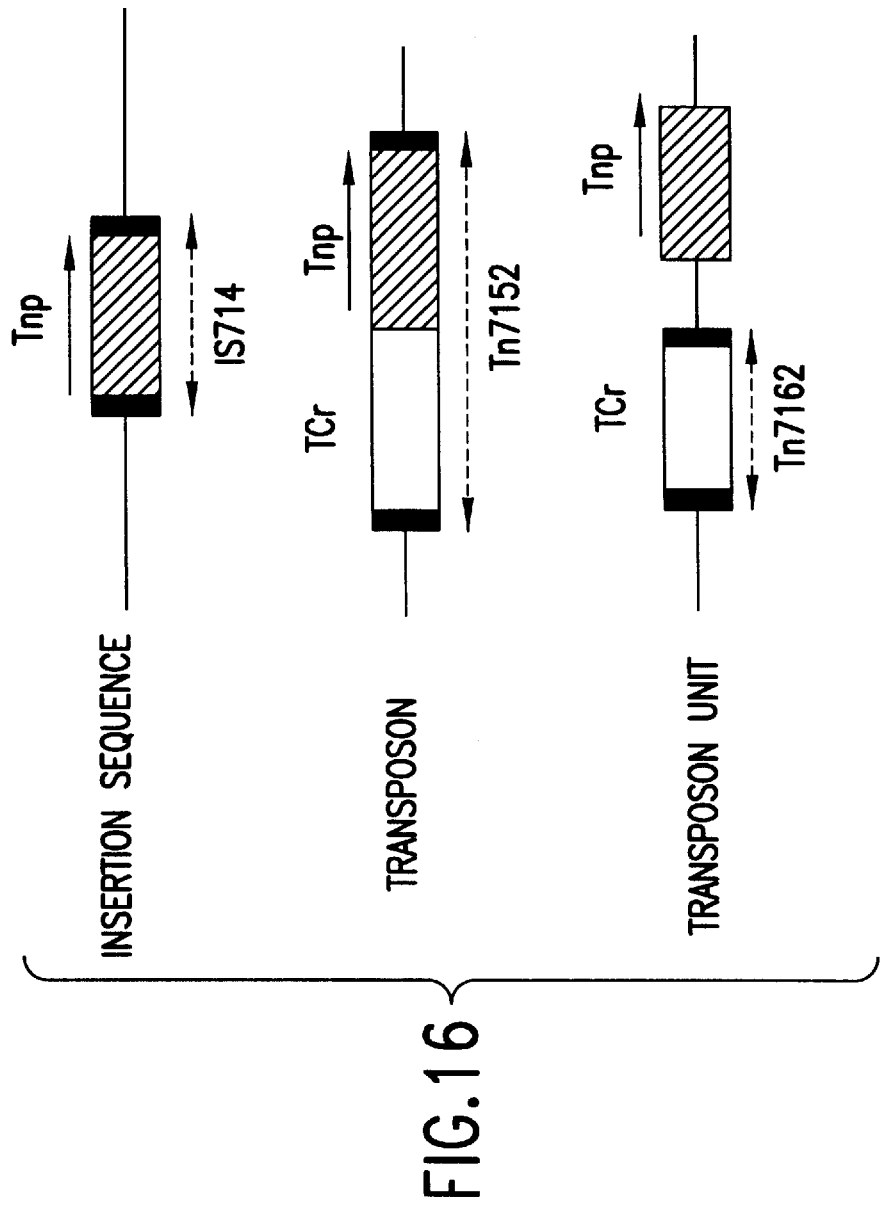
FIG. 16 shows the difference between an insertion sequence, an artificial transposon and a transposon unit. TCr means a tetracycline resistant gene, Tnp means a transposase gene and the black-box means an inverted repeat sequence (IR). The dot-underlined portion under the structure figures indicates a region to be transposed.

The unit containing IRs on both ends of IS714 and the Tc resistance gene is designated as transposon unit Tn7162. IS714 itself or the above described Tn7152 and the like have a structural gene of a transposase within a region which is able to transpose, while Tn7162 is characterized in the structure that it does not have a structural gene of a transposase within a region which is able to transpose. It is considered that Tn7162 is transposed by a transposon expressed from a transposon gene which is located outside the unit and is on the vector carrying Tn7162 (FIG. 16). Or it is considered that Tn7162 transposes by a transposase expressed from a transposase gene on a chromosome. Next the construction of a plasmid for coryneform bacteria which contains a transposase gene and no transposon unit is explained.

Figure 17:
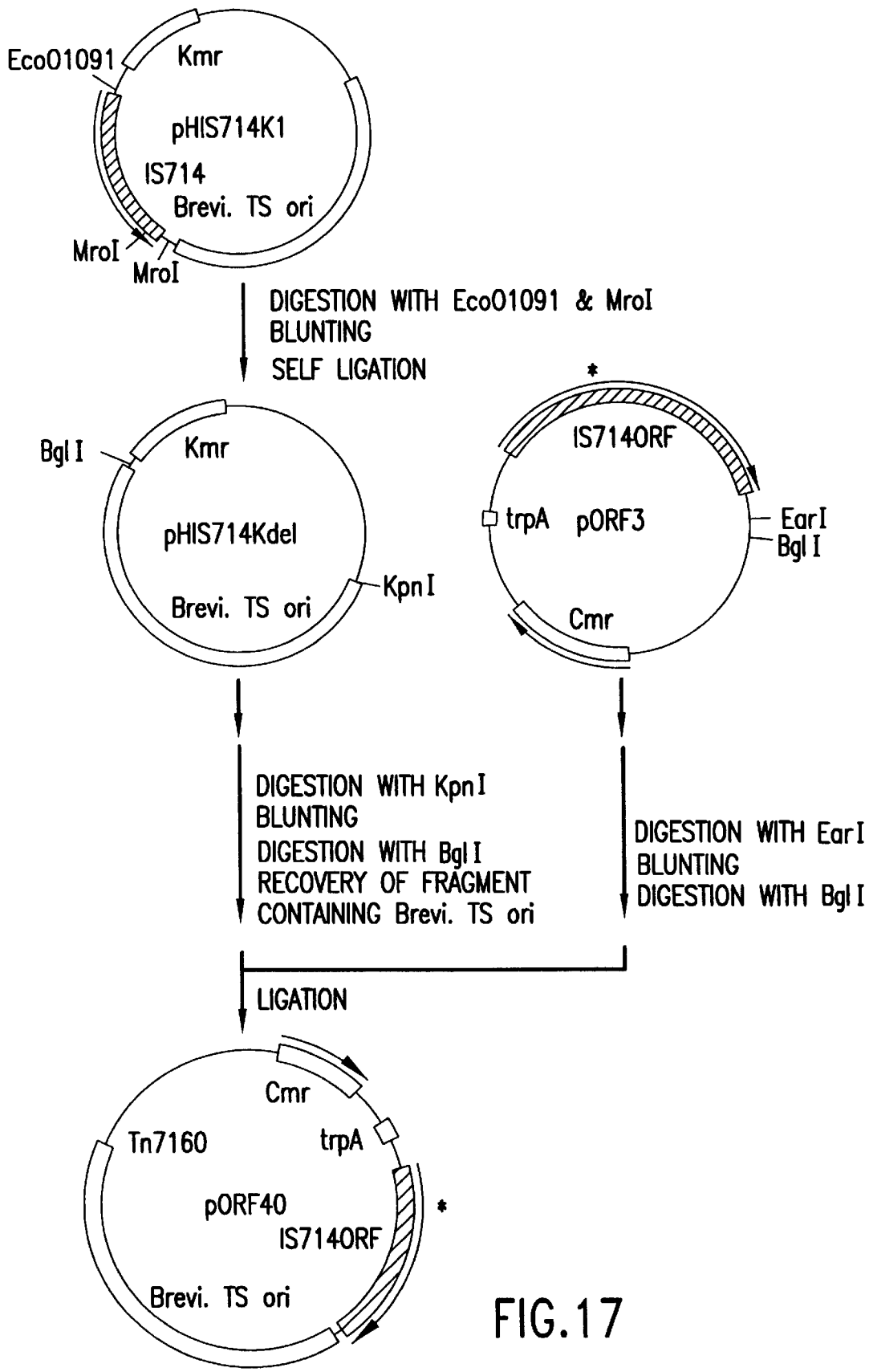
FIG. 17 is a view showing construction of the plasmid pORF40.

Plasmid pHIS714K1 is cleaved with EcoO 109I and Mro I to delete IS714, and is then self-ligated to construct pHIS714Kdel. Meanwhile, pORF3 is cleaved with restriction endonuclease Ear I, end-blunted, and cleaved again with Bgl I. pHIS714Kdel is cleaved with restriction endonuclease Kpn I, end-blunted, and then cleaved again with Bgl I to form a fragment which contains a temperature-sensitive replication origin functioning within coryneform bacteria. The thus-formed fragments are ligated with each other to construct pORF40 as shown in FIG. 17.

This method is repeated to construct pORF30 from pORF4, pORF70 from pORF 7, pORF80 from pORF 8 and pORFC1 from pORFC0 respectively.

With respect to insertion sequences of the coryneform bacteria such as IS719 and IS903 having the nucleotide sequences of SEQ ID NOS: 5 and 9 which are different from the above-mentioned IS714, artificial transposons can be constructed by inserting drug resistance genes such as a chloramphenicol resistance gene and a tetracycline resistance gene, and desired genes such as an aspartokinase gene in appropriate restriction endonuclease sites outside the regulatory gene region and the structural gene region of the transposase gene in the insertion sequence. When there is no appropriate restriction endonuclease site outside the regulatory gene region and the structural gene region of the transposase gene, an appropriate restriction endonuclease site may be prepared in advance in a region which does not inhibit the transposase function by modifying the insertion sequence by partial specific mutation of bases using polymerase chain reaction (PCR), or by gene insertion with a synthetic DNA oligonucleotide (adapter).

The thus-constructed artificial transposon is introduced into a host coryneform bacterium through an appropriate vector, for example, a plasmid. A plasmid in which to contain an artificial transposon is not particularly limited. A plasmid derived from coryneform bacteria is usually employed.

Suitable plasmids include pHM1519 (Agric. Biol. Chem., 48, 2901–2903 (1984)), pAM330 (Agric. Biol. Chem., 48, 2901–2903 (1984)), and drug resistance gene-containing plasmids obtained by improving the above-mentioned plasmids. In order to amplify the artificial transposon introduced in a chromosome at good efficiency, it is advisable to use the plasmid having the temperature-sensitive replication origin as mentioned in (1) (refer to Japanese Kokai No. 7,491/1993).

The plasmid containing the artificial transposon may be introduced into the coryneform bacterium by the protoplast method (Gene, 39, 281–286 (1985)) or the electroporation method (Bio/Technology, 7, 1067–1070 (1989)).

The artificial transposon may be introduced into a chromosome of a coryneform bacterium through a temperature-sensitive plasmid by transforming the coryneform bacterium with the plasmid constructed, incubating the transformant at 25° C. at which the plasmid can be replicated to amplify the artificial transposon-containing plasmid to from scores to hundreds of copies per cell and introduced into the chromosome, and then conducting incubation at 34° C. to remove extra plasmids. The gene amplification is conducted in the chromosome at good efficiency by this method. A normal plasmid can be used instead of the temperature-sensitive plasmid. However, it is difficult, in many cases, to remove extra plasmids after the introduction of the artificial transposon into the chromosome. Further, there is also a method in which an artificial transposon is introduced into a coryneform bacterium using a DNA fragment of an artificial transposon alone or a plasmid vector which cannot be replicated in coryneform bacteria (for example, a plasmid vector which is replicated in *Escherichia coli*) (Japanese Kokai No. 107,976/1995; and Mol. Gen. Genet., by Vertes A. A., Asai Y., Inui M., Kobayashi M., Kurusu Y. and Yukawa H., 245, 397–405 (1994)). However, in this method, the DNA fragment cannot be amplified within the host strain after the transformation, and the efficiency of transposition into the host chromosome is quite bad.

The strain in which the desired gene is introduced into the chromosome or the strain in which the desired gene is amplified in the chromosome is selected using the degree of drug resistance of the drug resistance gene which is introduced together with the desired gene. The drug resistance gene to be used includes a kanamycin resistance gene, a chloramphenicol resistance gene, a tetracycline resistance gene, an ampicillin resistance gene, a methotrexate resistance gene and the like. The drug resistance gene in which the degree of resistance is correlated with the number of copies of the drug resistance gene is most preferable. That is, it is possible to obtain the strain in which the desired gene is amplified in the chromosome from the clone which can be grown in the presence of the drug having a higher concentration. After the coryneform bacterium is transformed using the plasmid (for example, pHTN7156-C) containing the drug resistance gene such as the tetracycline resistance gene or the like and the desired gene such as the desensitized aspartokinase gene or the like and the artificial transposon is transposed into the host chromosome, the number of the transposition copies in the chromosome formed after the transposition can be evaluated by the following method.

The transformant is incubated overnight at 25° C. in a CM2G liquid medium containing a selected drug such as tetracycline (Tc) or the like at an appropriate concentration (from 1 to 20 $\mu$g/ml in the case of Tc), 10 g/liter of yeast extract, 10 g/liter of tryptone, 5 g/liter of glucose and 5 g/liter of NaCl. The culture is appropriately diluted with a 0.9% NaCl solution, and is spread on the CM2G agar medium containing the appropriate concentration of the drug in an amount of 100 $\mu$l. The resulting culture is incubated at 34° C. Several clones are selected randomly from many colonies formed. The chromosomal DNA is prepared, completely digested with various appropriate restriction endonucleases including Pvu II, and subjected to agarose gel electrophoresis. The fragments are blotted on a filter of nitrocellulose, nylon or polyvinylidene difluoride (PVDF). This filter is subjected to the southern hybridization using a $^{32}$P-labelled tetracycline resistance gene fragment as a probe to detect the number of bands which are hybridized with this probe.

The transformant in which the desired gene is amplified in the thus-obtained chromosome may be incubated using a method and conditions which are ordinarily employed. The culture medium for the incubation is an ordinary culture medium containing a carbon source, a nitrogen source, an inorganic ion and the like. It is advisable that organic micronutrients such as vitamins, amino acids and the like be added as required.

Suitable carbon sources include carbohydrates such as glucose and sucrose, organic acids such as acetic acid, and alcohols such as ethanol. Suitable nitrogen sources include ammonia gas, aqueous ammonia, and ammonium salts. Suitable inorganic ions include a magnesium ion, a phosphoric acid ion, a potassium ion, and an iron ion. These sources are used as required the sources can be determined/monitored by general knowledge in fermentation technology or through trial and error.

The incubation is conducted aerobically for from 1 to 7 days while controlling the pH to the range of from 5.0 to 8.5 and the temperature to the range of from 15° C. to 37° C. The gene is amplified using the artificial transposon, with the result that the efficiency of producing the desired useful substance is increased and the desired substance is produced and accumulated inside or outside the cultured strain. The desired substance can be collected from the culture by a known method.

Having generally described this invention, a further understanding can be obtained by reference to certain specific examples which are provided herein for purposes of illustration only and are not intended to be limiting unless otherwise specified.

EXAMPLES

Example 1
Construction of an artificial transposon containing a kanamycin resistance gene using IS714

Plasmid pEC701-IS14 having a sequence of IS714 which is an insertion sequence of a coryneform bacterium was cleaved with restriction endonucleases Pvu II and Eco RI to obtain a fragment of 1.6 kb containing IS714. *Brevibacterium lactofermentum* AJ12684 containing plasmid pEC701-IS14 deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under deposit No. FERM P-12863 on Mar. 10, 1992, and was converted to a deposit under the conditions of the Budapest Treaty on Mar. 9, 1993as Deposit No. BP-4232 was allotted thereto.

Meanwhile, temperature-sensitive plasmid pHSC4 was digested with a restriction endonuclease SalI and made blunt by the treatment with the Klenow fragment. The restriction endonuclease Sal I site of temperature-sensitive plasmid pHSC4 is located in the region which does not participate in the replication. Also a fragment containing IS714 was end-blunted by the treatment with the Klenow fragment. The resulting fragment was then inserted into the restriction endonuclease Sal I site through the ligation to produce plasmid pHIS714 as shown in FIG. 2. *Escherichia coli* AJ12571 containing plasmid pHSC4 was deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under FERM P-11763 on Oct. 11, 1990, and was converted to a deposit under the provisions of the Budapest Treaty on Aug. 26, 1991 as Deposit No. BP-3524. The above-obtained fragment of 1.6 kb containing IS714 was end-blunted by the treatment with the Klenow fragment, and was inserted into the Sma I site of this pHIS714 through the ligation to construct plasmids pHTN7141 and pHTN7142 as shown in FIG. 2. The analysis by the restriction endonuclease cleavage revealed that the two IS714 fragments were inserted in the same direction in plasmid pHTN7141 but in the opposite directions in plasmid pHTN7142.

Fragments each containing two IS714 sequences and the sequence of the temperature-sensitive replication origin in the coryneform bacterium of pHSC4 can be cut out by cleaving pHTN7141 and pHTN7142 with restriction endonuclease Pvu II. On the other hand, plasmid vector pHSG298 (made by Takara Shuzo) has also two restriction endonuclease Pvu II sites. Thus, a fragment of 2.3 kb containing a neomycin phosphotransferase gene (kanamycin resistance gene) can be obtained by cleaving pHSG298 with restriction endonuclease Pvu II.

pHTN7141 and pHSG298 were cleaved with restriction endonuclease Pvu II, and were then ligated with each other to transform *Brevibacterium lactofermentum* AJ12036. Plasmid pHTN7143 was obtained from the transformant strain which was resistant to 25 g/ml of kanamycin (Km) as shown in FIG. 3. *Brevibacterium lactofermentum* AJ12826 containing plasmid pHTN7143 was deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under the provisions of the Budapest Treaty on Mar. 9, 1993 as Deposit No. BP-4231.

Plasmid pHTN7144 was obtained from pHTN7142 and pHSG298 in the above-mentioned manner as shown in FIG. 4. pHTN7143 and pHTN7144 had a structure that a neomycin phosphotransferase gene was held between two IS714 sequences. Further, plasmids pHIS714K1 and pHIS714K2 were prepared from plasmid pHIS714 and pHSG298 as control plasmids as shown in FIG. 5. In pHIS714K1 and pHIS714K2, the insertion fragments each containing the neomycin phosphotransferase gene were located in opposite sites.

In order to minimize the artificial transposon, an artificial transposon was constructed in which a neomycin phosphotransferase gene was inserted into one IS714 sequence.

The restriction endonuclease Nhe I site is present in a position of IS714 which does not impair the transposase function. Therefore, plasmid pHIS714 was cleaved with restriction endonuclease Nhe I, and the ends thereof were blunted. Meanwhile, the neomycin phosphotransferase gene region was cut out from plasmid pUC4K (made by Pharmacia Biotech) with restriction endonuclease Pst I, and the ends thereof were blunted. These fragments were ligated with each other, and the resulting plasmid was designated pHTN7145 as shown in FIG. 6.

*Escherichia coli* AJ13128 containing plasmid pHTN7145 was deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under FERM P-15011 on Jun. 29, 1995, and was converted to a deposit under the provisions of the Budapest Treaty on May 16, 1996 as Deposit No. BP-5537.

Evaluation of transposition performance of artificial transposons

The transposition performance of the thus-obtained artificial transposons was evaluated as follows.

*Brevibacterium lactofermentum* AJ12036 was transformed with plasmid pAJ43 having the chloramphenicol acetyltransferase gene to produce *Brevibacterium lactofermentum* AJ 11882. *Brevibacterium lactofermentum* AJ11882 was transformed with plasmid pHTN7145 containing the artificial transposon so that plasmid pAJ43 and plasmid pHTN7145 were coexistent in this *Brevibacterium lactofermentum*. *Escherichia coli* AJ11882 containing pAJ43 was deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under FERM P-6517 on Apr. 28, 1982, and was coverted to a deposit under the provisions of the Budapest Treaty on May 22, 1982 as Deposit No. BP-136.

The above-obtained *Brevibacterium lactofermentum* containing pHTN7145 and pAJ43 coexistently was incubated overnight at 25° C. in a CM2G culture medium containing 25 μg/ml of kanamycin (Km), 5 μg/ml of chloramphenicol (Cm), 10 g/liter of yeast extract, 10 g/liter of tryptone, 5 g/liter of glucose and 5 μg/liter of NaCl while being shaken. The culture solution was then appropriately diluted, spread on a CM2G agar medium containing 25 μg/ml of Km and 5 μg/ml of Cm, and incubated at 34° C. Plasmids were extracted from 100 strains among the colonies formed, and the sizes thereof were examined through electrophoresis. Of these, three are different with respect to the molecular weights from both plasmids pHTN7145 and pAJ43. They were plasmids of which the molecular weight was the total of the molecular weights of pAJ43 and the artificial transposon.

When these plasmids were analyzed through the restriction endonuclease cleavage, it was found that the sequence in pHTN7145 was inserted into pAJ43. With respect to one of these plasmids, the nucleotide sequence in the vicinity of the portion inserted in pAJ43 and the insertion fragment was determined by the dideoxy method.

Consequently, it was identified that the sequences of both ends of the artificial transposon were present, and the target sequence GGTTTATT (Sequence No. 12) on pAJ43 which underwent the insertion was duplicated.

From these results, it was found that when the transposon structure was taken in which the gene that does not participate in the transposition performance (neomycin phosphotransferase gene) was inserted in one IS714 sequence, it was transposed like a transposon with this structure stored.
Evaluation of a transposition frequency of an artificial transposon Brevibacterium lactofermentum AJ12036 was transformed with pHTN714K1, a control plasmid, pHTN7143, pHTN7144 and pHTN7145 and the frequency of transposition of the artificial transposon into the host chromosome was evaluated. pHTN7143, pHTN7144 and pHTN7145 all contained the artificial transposon.

Each of the transformants was incubated overnight at 25° C. in the above-mentioned CM2G liquid medium containing 25 µg/ml of Km. Then, the culture was approximately diluted with a 0.9% NaCl solution, and was spread on CM2G agar medium containing 25 µg/ml of Km in an amount of 100 µl. The resulting substance was incubated at 34° C. and 25° C., and the frequency at which the Km resistance strain was appeared at each temperature was measured from the number of colonies. The number of colonies at 34° C. was divided by the number of colonies at 25° C. The resulting value was defined as the transposition frequency.

The results are shown in Table 1.

TABLE 1

| Transposable element or artificial transposon | Transposition frequency | Relative ratio |
|---|---|---|
| IS714 | $1.85 \times 10^{-3}$ | 1 |
| Tn7143 | $3.52 \times 10^{-3}$ | 1.9 |
| Tn7144 | $2.38 \times 10^{-3}$ | 1.3 |
| Tn7145 | $2.08 \times 10^{-2}$ | 11.2 |

From the above-mentioned results, it is found that artificial transposons Tn7143 (contained in pHTN7143) and Tn7144 (contained in pHTN7144) had the frequency of transposition into the host chromosome which was only 1 or 2 times as high as that of IS714 (contained in pHIS714K1) as a control plasmid, but that artificial transposon Tn7145 (contained in pHTN7145) was approximately 11 times and therefore it was a quite efficient artificial transposon.

Example 2
Construction of an artificial transposon containing a chloramphenicol resistance gene using IS714

Plasmid vector pHSG398 (made by Takara Shuzo) was cleaved with restriction endonuclease Acc II to obtain a fragment of approximately 1.1 kb containing a chloramphenicol acetyltransferase gene. This Acc II fragment was inserted into a Sma I site of pUC18 (made by Takara Shuzo), and cloned. That is, a desired clone was selected from Escherichia coli transformant which had been grown in an L-medium containing 25 µg/ml of Cm, 100 µg/ml of ampicillin (Ap), 10 g/liter of tryptone, 5 g/liter of yeast extract and 5 g/liter of NaCl. The plasmid was designated pUC18-CM.

Further, a fragment of approximately 1.1 kb which was cut out from pUC18-CM with Eco RI and Hind III and which contained a chloramphenicol acetyltransferase gene was end-blunted. In pHIS714K2 constructed in Example 1, the restriction endonuclease Nhe I site of IS714 located in the position which does not impair the transposase function was end-blunted by the treatment with the Klenow fragment. The above-mentioned fragment was ligated with this restriction endonuclease Nhe I site to transform Escherichia coli. Colonies which were grown on an L-agar-medium containing 25 µg/ml of Cm and 50 µg/ml of Km were picked up. A clone having inserted therein the chloramphenicol acetyltransferase gene fragment was selected. The plasmid contained in this clone was designated pHTN7151 as shown in FIG. 7.

Escherichia coil AJ13129 obtained by transforming Escherichia coil HB101 with plasmid pHTN7151 was listed as deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under FERM P-15012 on Jun. 29, 1995, and was transferred to the deposition based on the Budapest Treaty on May 16, 1996. Deposit No. BP-5538 is allotted thereto.
Evaluation of the number of copies in the chromosome formed by the transposition of the artificial transposon Brevibacterium lactofermentum AJ12036 was transformed with pHTN7151, and the number of copies of the artificial transposon in the chromosome which were formed by the transposition of the artificial transposon into the host chromosome was evaluated by the following method. The resulting transformant was incubated overnight at 25° C. in the above-mentioned CM2G liquid medium containing 3 µg/ml of Cm, appropriately diluted with a 0.9% NaCl solution, and spread on a CM2G agar medium containing 3 µg/ml of Cm in an amount of 100 µl. The resulting substance was incubated at 34° C. A kanamycin-sensitive clone was selected from colonies appeared. This clone was incubated overnight at 30° C. in the above-mentioned CM2G liquid medium containing 3 µg/ml of Cm, appropriately diluted with a 0.9% NaCl solution, and spread on the above-mentioned CM2G agar medium containing 6 µg/ml of Cm in an amount of 100 µl. The resulting substance was incubated at 30° C., and some clones were randomly selected from colonies formed. A chromosomal DNA was prepared from each of the clones, completely digested with restriction endonuclease Pvu II, subjected to agarose gel electrophoresis, and blotted on a polyvinylidene difluoride (PVDF) filter. This filter was subjected to the southern hybridization using a $^{32}$P-labelled chloramphenicol acetyltransferase gene fragment as a probe, and the number of bands hybridized with the probe was measured.

As a result, it was identified that in the three of the four clones randomly selected, two copies of the artificial transposon having the chloramphenicol resistance gene were transposed into the host chromosome.

Example 3
Construction of an artificial transposon containing a tetracycline resistance gene using IS714

Plasmid vector pBR322 (made by Takara Shuzo) was cleaved with restriction endonucleases Eco RI and Ava I to obtain a fragment of approximately 1.4 kb having a tetracycline resistance gene. Then, this Eco RI-Ava I-cleaved fragment was end-blunted by the treatment with the T4 DNA polymerase. In pHIS714K2 constructed in Example 1, the restriction endonuclease Nhe I site of IS714 located in the position which does not impair the transposase function was end-blunted by the treatment with the Klenow fragment. The above-mentioned fragment was ligated with this restriction endonuclease Nhe I site to transform *Escherichia coli*. Colonies grown in an L-agar-medium containing 25 µg/ml of Tc were obtained, and the clone having inserted therein the tetracycline resistance gene was selected. The plasmid contained in this clone was designated pHTN7152 as shown in FIG. 8.

*Escherichia coli* AJ13130 obtained by transforming *Escherichia coli* with plasmid pHTN7152 was listed as deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) under FERM P-15013 on Jun. 29, 1995, and was transferred to the deposition based on the Budapest Treaty on May 16, 1996. Deposit No. BP-5539 is allotted thereto.

Evaluation of the number of copies in the chromosome formed by the transposition of the artificial transposon

*Brevibacterium lactofermentum* AJ12036 was transformed using pHTN7152, and the number of copies in the chromosome which were formed by the transposition of the artificial transposon was evaluated as follows.

The transformant was incubated overnight at 25° C. in the above-mentioned CM2G liquid medium containing 1.5 µg/ml of Tc, then appropriately diluted with a 0.9% NaCl solution, and spread on the above-mentioned CM2G agar medium containing Tc in the range of from 1.5 µg/ml to 5 µg/ml. The resulting substance was incubated at 34° C. Some clones were randomly selected from the colonies formed. A chromosomal DNA was prepared from each of the colonies, completely digested with restriction endonuclease Pvu II, subjected to agarose gel electrophoresis, and blotted on a polyvinylidene difluoride (PVDF) filter. This filter was subjected to the southern hybridization using a $^{32}$P-labeled tetracycline resistance gene fragment as a probe, and the number of bands hybridized with the probe was measured.

Consequently, as shown in Table 2, two or three copies of the artificial transposon having the tetracycline resistance gene were detected at high frequency. Thus, it was identified that the desired multi-copying-type transformant could be obtained at high frequency using the tetracycline resistance gene as the selective drug resistance gene.

TABLE 2

| Tc concentration (µg/ml) | Number of test clones | Number of test clones | | |
|---|---|---|---|---|
| | | 1 copy | 2 copies | 3 copies |
| 1.5 | 6 | 4 | 2 | 0 |
| 2.0 | 4 | 4 | 0 | 0 |
| 3.0 | 4 | 3 | 1 | 0 |
| 4.0 | 6 | 2 | 3 | 1 |
| 5.0 | 6 | 5 | 1 | 0 |

*Brevibacterium lactofermentum* AJ13188 which is resistant to 4 µg/ml of Tc and is found to have 3 copies of the artificial transposon on the chromosome was listed as deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) based on the Budapest Treaty on May 14, 1996. Deposit No. BP-5536 is allotted thereto.

Example 4

Construction of an artificial transposon containing a tetracycline resistance gene and an aspartokinase gene using IS714

An aspartokinase gene which is one of lysine biosynthesis genes was inserted into an artificial transposon containing a tetracycline resistance gene in the following manner.

Plasmid vector pBR322 (made by Takara Shuzo) was cleaved with restriction endonucleases Eco RI and Ava I to obtain a DNA fragment of approximately 1.4 kb containing the tetracycline resistance gene. This Eco RI-Ava I-cleaved fragment was end-blunted by the treatment with the T4 DNA polymerase. The thus-obtained DNA fragment was ligated with a fragment obtained by cleaving plasmid vector pHY300PLK (made by Takara Shuzo) with restriction endonuclease Sma I to transform *Escherichia coli*. Colonies grown in an L-agar-medium containing 25 µg/ml of Tc were obtained, and the clone having inserted therein the tetracycline resistance gene fragment was selected. The plasmid of this clone was designated pHY300-TC.

Further, a fragment obtained by cleaving pHY300-TC with restriction endonucleases Eco RI and Xba I and containing the tetracycline resistance gene of pBR322 was end-blunted by the treatment with the Klenow fragment. In the above-constructed pHIS714K2, the restriction endonuclease Nhe I site of IS714 located in the position which does not impair the transposase function was end-blunted by the treatment with the Klenow fragment. The above-mentioned fragment was ligated with this restriction endonuclease Nhe I site to transform *Escherichia coli*. Colonies grown in the L-agar-medium containing 25 µg/ml of Tc were obtained. The clone having inserted therein the tetracycline resistance gene fragment was selected. The plasmid contained in this clone was designated pHTN7156 as shown in FIG. 9.

On the other hand, *Escherichia coli* AJ12691 (WO94/25605) having plasmid p399AK9B containing an aspartokinase gene which was derived from a lysine-producing mutant of *Brevibacterium lactofermentum* and which is desensitized to the concerted inhibition of lysine and threonine was listed as deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) on Apr. 10, 1992 under FERM P-12198, and was transferred to the deposition based on the Budapest Treaty on Feb. 10, 1995. Deposit No. FERM BP-4999 is allotted thereto.

This p399AK9B was cleaved with restriction endonuclease Bam HI, and was self-ligated to construct pHSC399AK from which the replication origin that functions in coryneform bacterium was removed. This pHSG399AK was cleaved with Eco RI and Sph I to obtain an aspartokinase gene fragment of approximately 1.7 kb. This fragment was end-blunted by the treatment with the T4 DNA polymerase. The restriction endonuclease Bgl II site of plasmid pHTN7156 which had the artificial transposon containing the tetracycline resistance gene was blunted by the treatment with the Klenow fragment. The above-formed fragment was then inserted into this restriction endonuclease Bgl II site. In this manner, plasmid pHTN7156-C was constructed as shown in FIG. 9.

*Escherichia coli* AJ13131 obtained by transforming *Escherichia coil* with plasmid pHTN7156-C was listed as deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) on Jun. 29, 1995. Deposit No. FERM P-15014 is allotted thereto. *Escherichia coli* AJ13131 was transferred to the deposit based on the Budapest Treaty on May 16, 1996. Deposit No. BP-5540 is allotted thereto.

Evaluation of the number of copies in a chromosome which are formed by transposition of an artificial transposon

*Brevibacterium lactofermentum* AJ12036 or *Brevibacterium lactofermentum* AJ3445 was transformed with pHTN7156-C. The number of copies of a transposon in a chromosome which were formed by transposition of an artificial transposon into a host chromosome was evaluated. The AJ12036 strain has a wild aspartokinase gene in the chromosome, while the AJ3445 strain exhibits S-2-amylethyl-L-cysteine resistance and has an aspartokinase gene which is desensitized to concerted inhibition of lysine and threonine.

*Brevibacterium lactofermentum* AJ12036 was deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) on Mar. 26, 1984. Deposit No. FERM P-7559 is allotted thereto.

*Brevibacterium lactofermentum* AJ12036 was transferred to the deposit based on the Budapest Treaty on Mar. 13, 1985. Deposit No. BP-734 is allotted thereto. *Brevibacterium lactofermentum* AJ3445 was deposited at the National Institute of Bioscience and Human Technology of the Agency of Industrial Science and Technology, Ministry of Industrial Trade and Industry (1-3, Higashi 1 Chome Tsukuba-shi Ibaraki-ken 305, Japan) on Mar. 2, 1973. Deposit No. FERM P-1944 is allotted thereto. *Brevibacterium lactofermentum* AJ12036 was transferred to the deposit based on the Budapest Treaty on May 17, 1996. Deposit No. BP-5541 is allotted thereto.

First, the transformant was incubated overnight at 25° C. in a CM2G medium containing 0.7 µg/ml of Tc, 10 g/liter of yeast extract, 10 g/liter of tryptone, 5 g/liter of glucose and 15 g/liter of NaCl. The culture was appropriately diluted with a 0.9-% NaCl solution, and was spread on the above-mentioned CM2G agar media containing from 1.5 µg/ml to 5 µg/ml of Tc in an amount of 100 µl. The resulting culture was incubated at 34° C. Some clones were selected randomly from among colonies formed, and were replicated in the CM2G agar medium containing 25 µg/ml of Km. Km-sensitive strains were then selected. Chromosomal DNAs of the Km-sensitive strains selected were produced, completely digested with restriction endonuclease Bgl II, subjected to agarose gel electrophoresis, and blotted on a polyvinylidene difluoride (PVDF) filter. This filter was subjected to the southern hybridization using a $^{32}$P-labelled aspartokinase gene fragment (of 440 bp from the Hind III site to the Eco RI site of the gene latter half) as a probe, and the number of bands hybridized with this probe was detected. As a result, it was found that when AJ12036 was used as a host, two copies of transposon Tn7156-C were transposed in the 4 of the 10 strains analyzed, and that when AJ3445 was used as a host, two copies of transposon Tn7156-C were transposed in the 8 of the 22 strains analyzed. This proved that plural copies of the useful gene can be transduced into the chromosome at high frequency by using a tetracycline resistance gene as the selective drug resistance gene.

Evaluation of an amount of lysine produced in a strain in which an aspartokinase gene was transposed using an artificial transposon The amount of lysine produced in the above-mentioned strain containing the transposon transposed therein was evaluated.

The strain containing the transposon was spread on the overall surface of a CM2G agar medium containing 0.7 µg/ml of Tc, and was incubated overnight at 34° C. The cells in an amount which was ⅙ of the original amount were inoculated in 20 ml of a lysine-productive medium containing 100 g/liter of glucose, 55 g/liter of ammonium sulfate, 50 ml/liter of Mamenou (Ajinomoto Co., Inc.), 1 g/liter of potassium dihydrogen phosphate, 1 g/liter of magnesium sulfate, 2 mg/liter of vitamin B1, 0.5 mg/liter of biotin, 5 mg/liter of nicotinic acid amide, 2 mg/liter of iron sulfate and 2 mg/liter of manganese sulfate (this medium was adjusted to a pH of 7.5, and then sterilized in an autoclave at 115° C. for 15 minutes, after which 50 g/liter of calcium carbonate were added thereto). The culture solution was incubated in a Sakaguchi flask at 30° C. for 72 hours. The content of lysine formed in the culture solution was analyzed, and the amount of lysine produced in the artificial transposon-containing strain was evaluated. Consequently, as shown in Tables 3 and 4, when AJ12036 and AJ3445 were used as parent strains, the increase in the amount of lysine produced was observed in the transposition of Tn7156-C as compared to the transposon-free strain. Further, the more the number of transposition copies (1 copy and 2 copies) of the transposon, the more the amount of lysine produced.

This proved that the amount of the amino acid produced in the strain could be increased by transducing copies of the useful gene using the tetracycline resistance gene as a selective drug resistance gene.

TABLE 3

Amount of lysin produced in a strain containing a transponson transposed therein using AJ12036 as a parent strain

| Strain | Number of transposition copies of Tn7156-C | Amount of lysine produced (g/liter) |
| --- | --- | --- |
| AJ12306 | 0 | 0.0 |
| Tn7156-Cint-Y1 | 1 | 12.8 |
| Tn7156-Cint-Y2 | 2 | 18.8 |

TABLE 4

Amount of lysin produced in a strain containing a transponson transposed therein using AJ3445 as a parent strain

| Strain | Number of transposition copies of Tn7156-C | Amount of lysine produced (g/liter) |
| --- | --- | --- |
| AJ3445 | 0 | 18.7 |
| Tn7156-Cint-06 | 1 | 21.3 |
| Tn7156-Cint-019 | 2 | 25.2 |

Example 5

Construction of shuttle vector pVK7

There is pAM330 which is a cryptic plasmid present in *Brevibacterium lactofermentum*, as described in Japanese Patent Publication No. 11,280/1989 and USP 4,788,762. This pAM330 is produced from *Brevibacterium lactofermentum* ATCC13869, and it can be used as a replication origin of a shuttle vector which is amplifiable in Brevibacterium.

Figure 18:
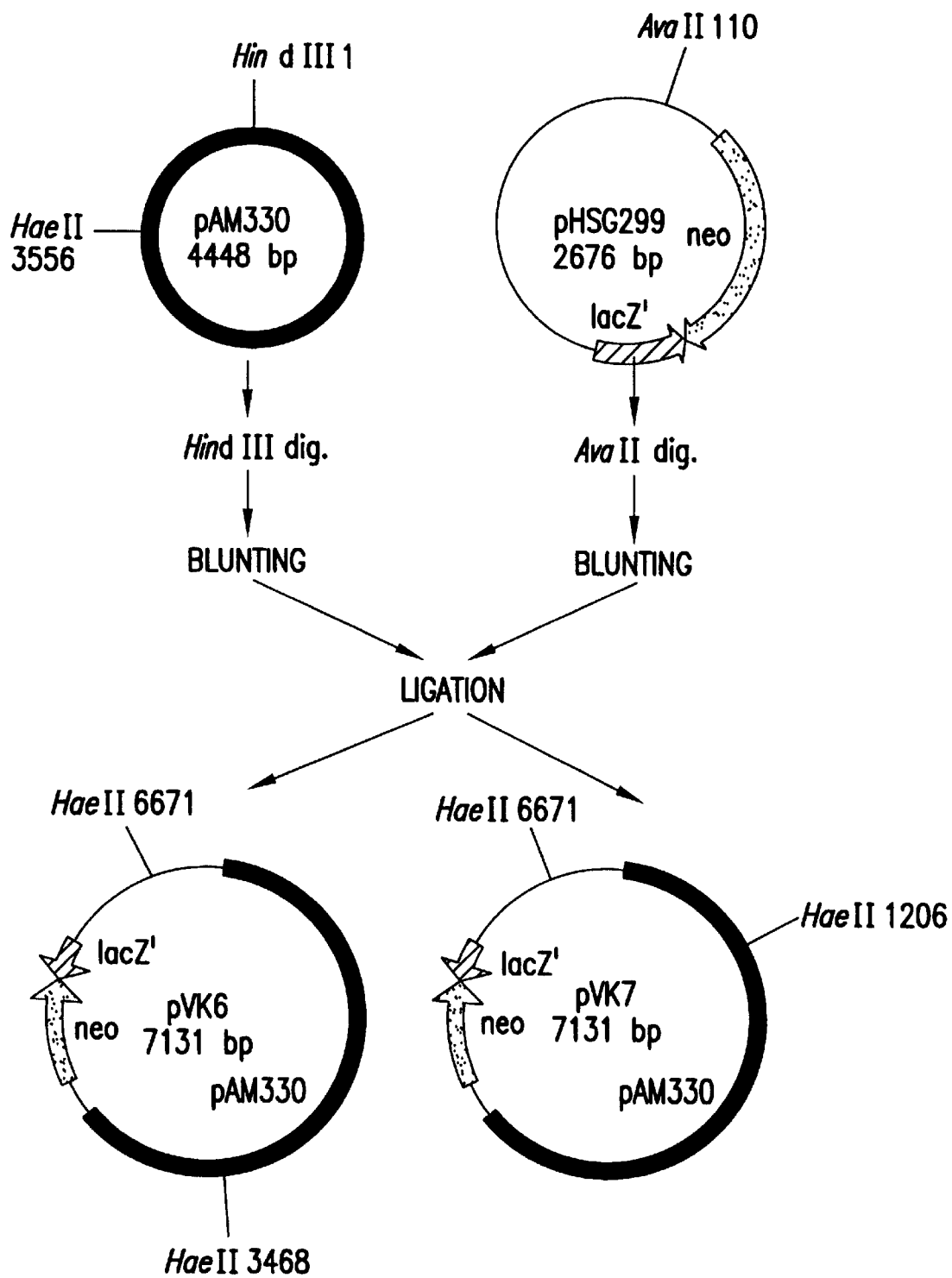
FIG. 18 is a view showing construction of the plasmid pVK7.

A novel shuttle vector was constructed by combining pHSG299 (made by Takara Shuzo) which is a multi-purpose vector for *E. coli* with pAM330.

pAM330 was cleaved with restriction endonuclease Hind III at one site, and the cleaved surface was end-blunted with a T4 DNA polymerase. Further, pHSG299 was cleaved with restriction endonuclease Ava II at one site, and the cleaved surface was end-blunted with a T4 DNA polymerase. The resulting fragments were ligated with each other to obtain a plasmid which was a combination of pAM330 and pHSG299. The construction of pVK7 is schematically shown in FIG. 18. pVK7 is replicable in *E. coli* and Brevibacterium, and imparts kanamycin resistance to a host. This vector has Pst I, Sal I, Bam HI, Kpn I, Sac I and Eco RI cloning sites each of which allows cleavage at one site and is derived from multiple cloning sites of pHSG299.

Construction of shuttle vector pVC7

Figure 19:
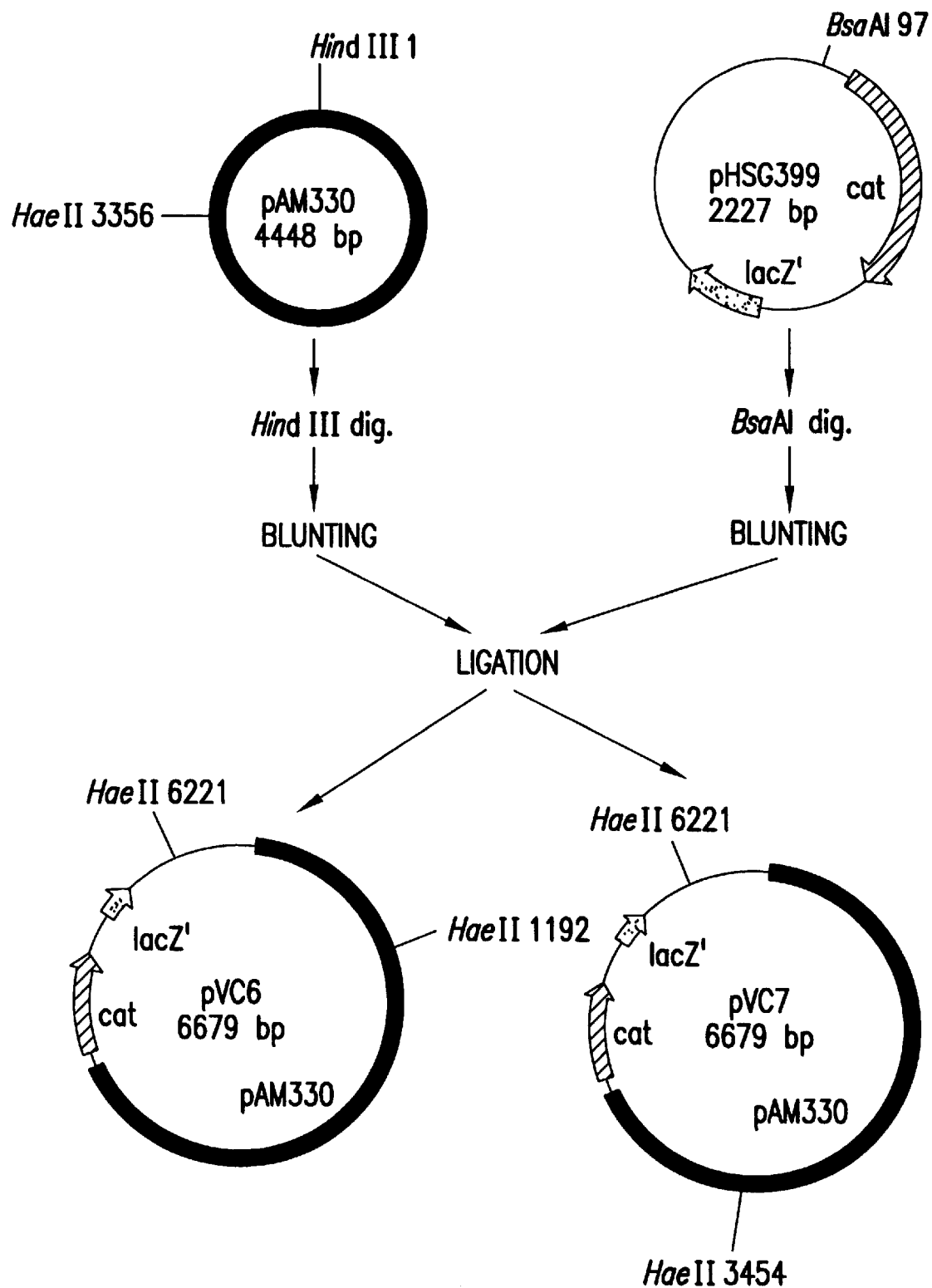
FIG. 19 is a view showing construction of the plasmid pVC7.

Novel shuttle vector pVC7 was constructed, like pVK7, by combining pHSG399 (made by Takara Shuzo) which is a multi-purpose vector for *E. coli* with pAM330.

pAM330 was cleaved with restriction endonuclease Hind III at one site, and the cleaved surface was end-blunted with a T4 DNA polymerase. Further, pHSG399 was cleaved with restriction endonuclease Bsa I at one site and end-blunted with a T4 DNA polymerase. The resulting fragments were ligated with each other to obtain a plasmid which was a combination of pAM330 and pHSG399. The construction of pVC7 was schematically shown in FIG. 19. pVC7 is replicable in *E. coli* and Brevibacterium, and imparts kanamycin resistance to a host. This vector has Pst I, Sal I, Bam HI, Kpn I, Sac I, Eco RI, Sma I and Hind III cloning sites each of which allow cleavage at one site, among multiple cloning sites of pHSG399.

Production of a plasmid containing dapA. dapB and lysA (1) Preparation of lysA and construction of plasmid containing lysA A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing argS, lysA, and a promoter of an operon containing them was amplified from the chromosomal DNA in accordance with PCR. As for DNA primers used for amplification, synthetic DNA's of 23-mers having nucleotide sequences depicted in SEQ ID NOs: 13 and 14, respectively, were used in order to amplify a region of about 3.6 kb coding for arginyl-tRNA synthase and DDC on the basis of a sequence known for *Corynebacterium glutamicum* (see Molecular Microbiology, 4(11), 1819–1830 (1990); Molecular and General Genetics, 212, 112–119 (1988)). Synthesis of DNA and PCR were performed by the conventional method. That is, DNA was synthesized in accordance with an ordinary method by using DNA synthesizer model 380B produced by Applied Biosystems and using the phosphoamidite method (see Tetrahedron Letters (1981), 22, 1859). The gene was amplified by PCR by using DNA Thermal Cycler Model PJ2000 produced by Takara Shuzo, and using Taq DNA polymerase in accordance with a method designated by the supplier. The sequence of the amplified DNA fragment is shown in SEQ ID NO: 15. The amino acid sequences encoded by the DNA of SEQ ID NO: 15 are listed as SEQ ID NO: 29 and 30.

pHSG399 was used as a cloning vector for the amplified gene fragment of 3,579 bp. pHSG399 was digested with a restriction enzyme SmaI, which was ligated with the DNA fragment containing amplified lysA. A plasmid obtained as described above, which had lysA originating from ATCC 13869, was designated as p399LYSA.

Figure 20:
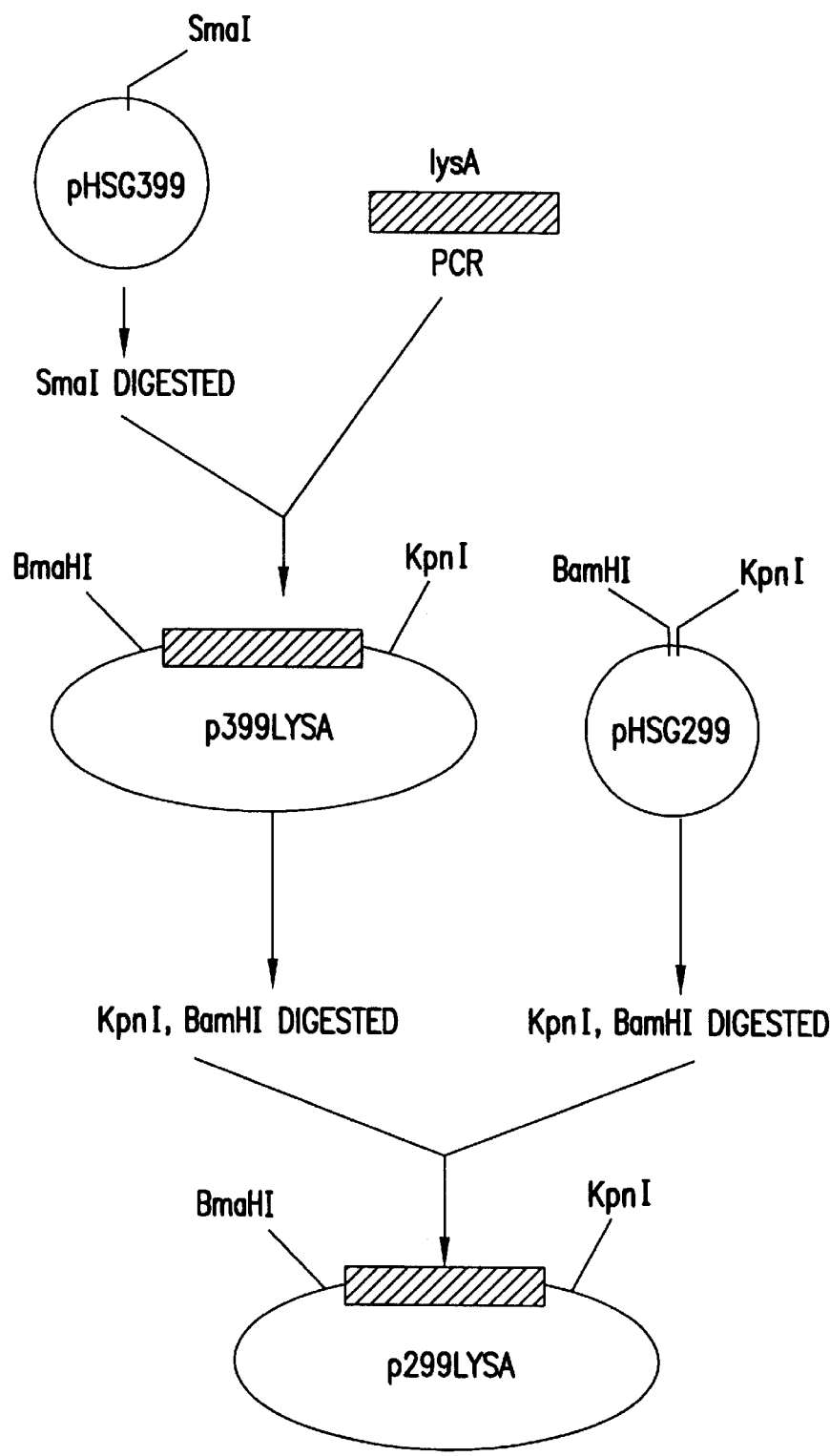
FIG. 20 is a view showing construction of the plasmids p399LYSA and p299LYSA.
Figure 21:
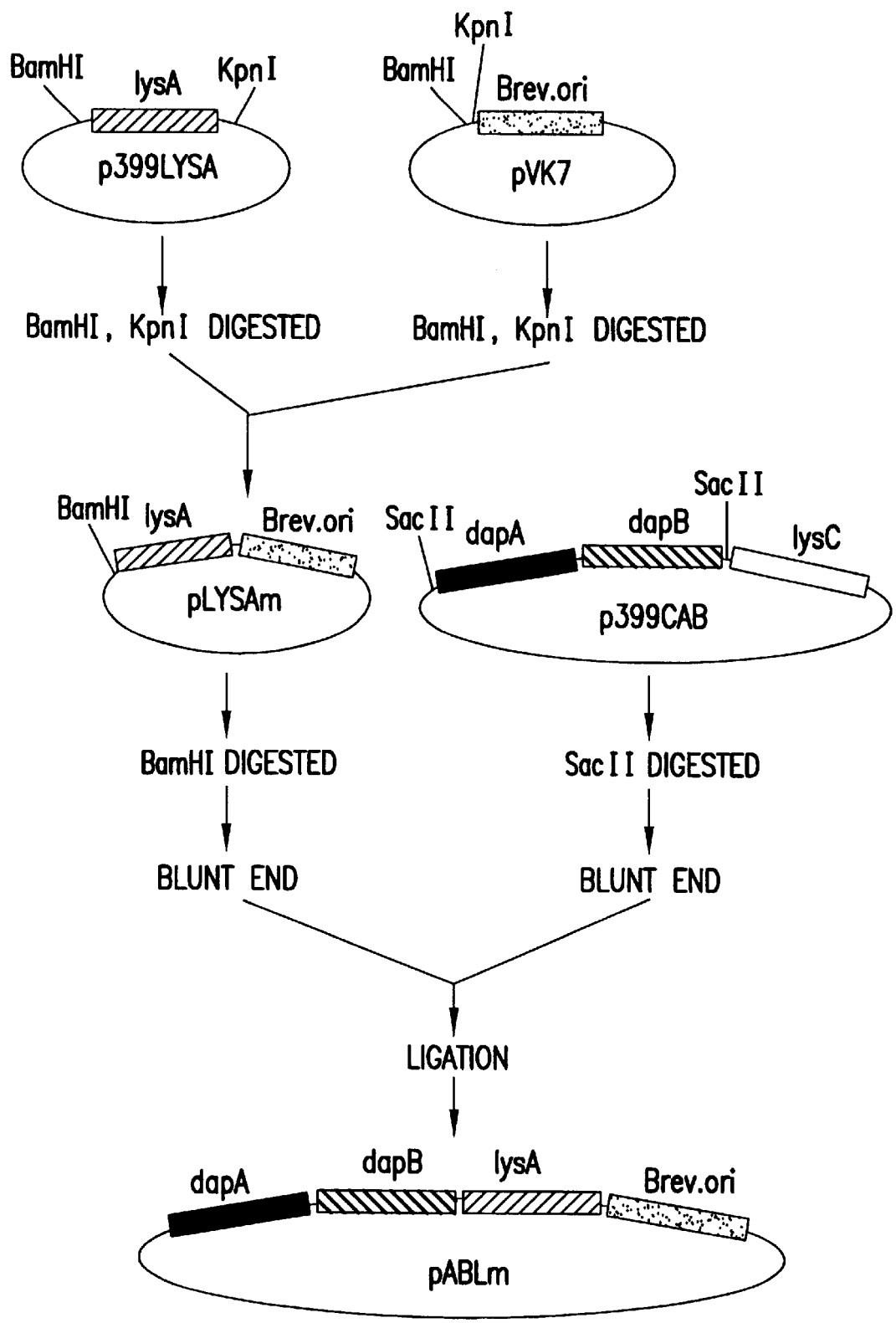
FIG. 21 is a view showing construction of the plasmid pABLm.

A DNA fragment containing lysA was extracted by digesting p399LYSA with KpnI and BamHI. This DNA fragment was ligated with pHSG299 having been digested with KpnI and BamHI. An obtained plasmid was designated as p299LYSA. The process of construction of p299LYSA is shown in FIG. 20.

p399LYSA was cleaved with restriction endonucleases Kpn I and Bam HI to extract a lysA fragment. This fragment was ligated with pVK7 cleaved with Kpn I and Bam HI. The thus-produced plasmid is designated pLYSAm (FIG. 21).

(2) Preparation of dapA and construction of plasmid containing dapA

Figure 22:
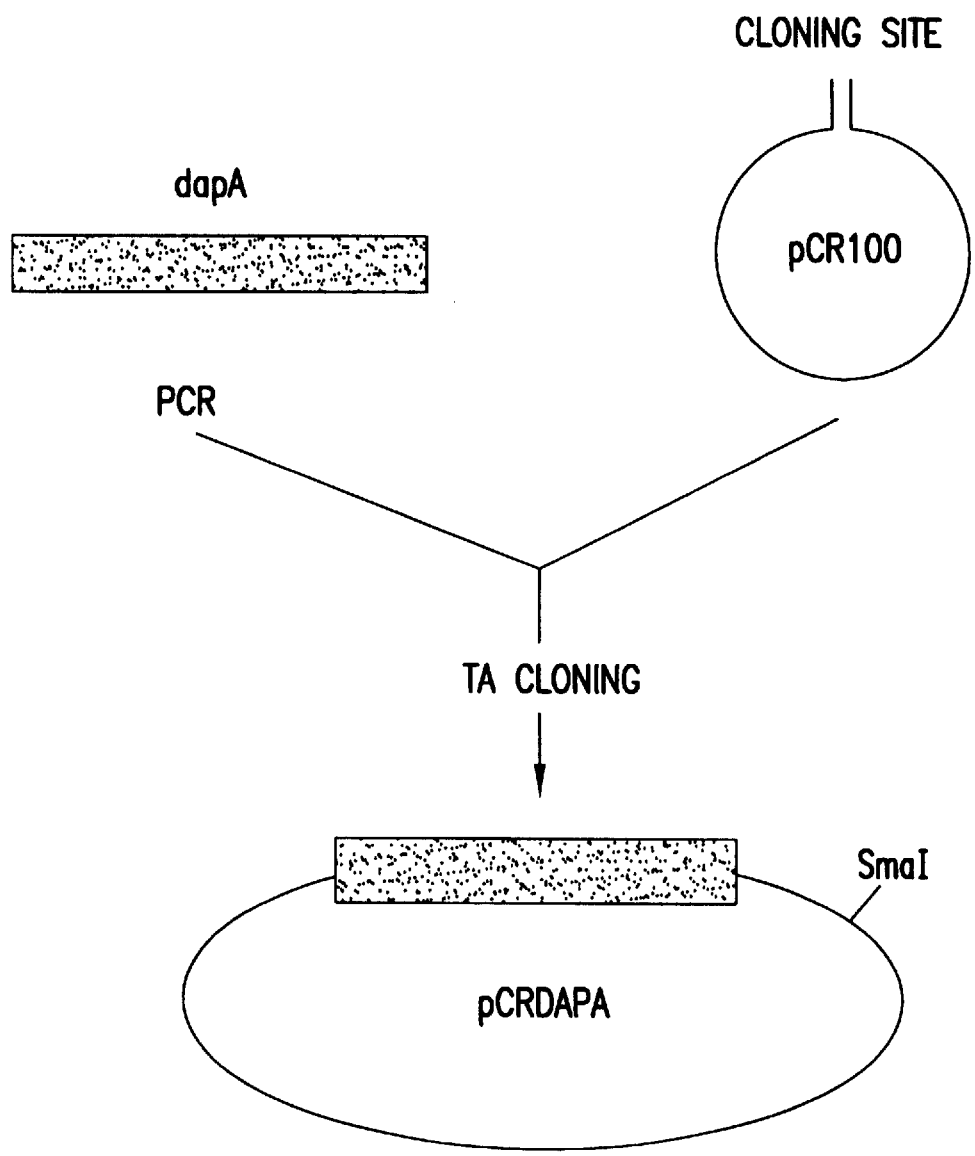
FIG. 22 is a view showing construction of the plasmid pCRDAPA.

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapA was amplified from the chromosomal DNA in accordance with PCR. As for DNA primers used for amplification, DNA's of 20-mers having nucleotide sequences shown in SEQ ID NOs: 16 and 17, respectively, were synthesized in order to amplify a region of about 1.5 kb coding for DDPS on the basis of a sequence known for *Corynebacterium glutamicum* (see Nucleic Acids Research, 18(21), 6421 (1990); EMBL accession No. X53993). Synthesis of DNA and PCR were performed by the conventional method. The sequence of the amplified DNA fragment is shown in the SEQ ID NO: 18. The amino acid sequences encoded by DNA of SEQ ID NO:18 are listed as SEQ ID NO:31. pCR1000 (produced by Invitrogen, see Bio/Technology, 9, 657–663 (1991)) was used as a cloning vector for the amplified gene fragment of 1,411 bp, which was ligated with the amplified dapA fragment. Ligation of DNA was performed by using DNA ligation kit in accordance with a designated method. Thus a plasmid was constructed, in which the dapA fragment of 1,411 bp amplified from chromosome of *Brevibacterium lactofermentum* was inserted into pCR1000. The plasmid obtained as described above, which had dapA originating from ATCC 13869, was designated as pCRDAPA (FIG. 22).

A transformant strain AJ13106 obtained by introducing pCRDAPA into an *E. coli* strain has been internationally deposited since May 26, 1995 under a deposition number of FERM BP-5113 in National Institute of Bioscience and Human Technology of Agency of Industrial Science and Technology of Ministry of Trade and Industry (postal code: 305, 1-3, Higashi 1-chome, Tsukuba-shi, Ibaraki-ken, Japan) based on the Budapest Treaty.

Figure 23:
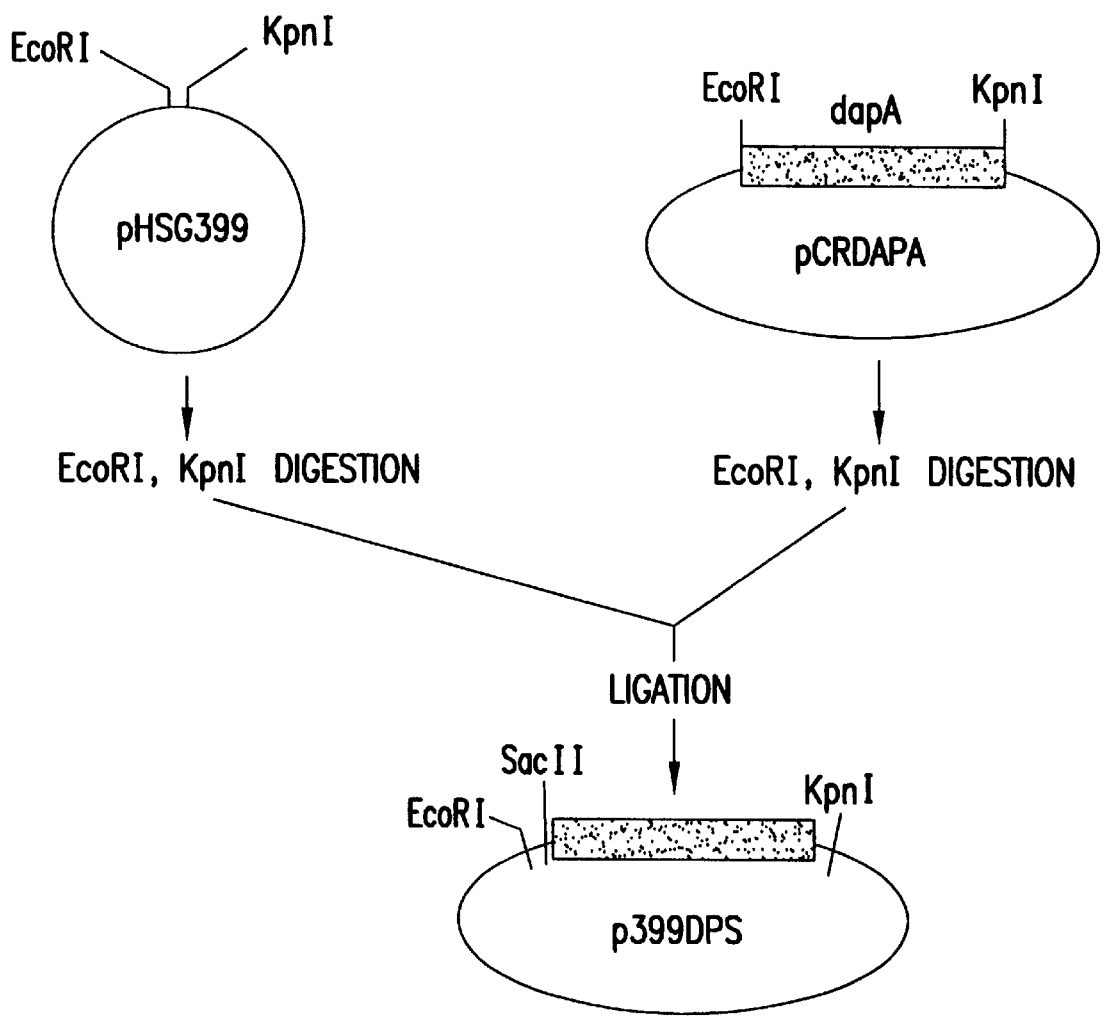
FIG. 23 is a view showing construction of the plasmid p399DPS.

Plasmid pCRDAPA containing dapA was digested with Kpn I and Eco RI and isolate the DNA fragment containing dapA. The fragment was ligated with pHSG399 digested with KpnI and EcoRI to obtain p399DPS (FIG. 23).

(3) Preparation of wild type and mutant lysC's and preparation of plasmids containing them A strain of *Brevibacterium lactofermentum* ATCC 13869, and an L-lysine-producing mutant strain AJ3445 obtained from the ATCC 13869 strain by a mutation treatment were used as chromosomal DNA donors. The AJ3445 strain had been subjected to mutation so that lysC was changed to involve substantial desensitization from concerted inhibition by lysine and threonine (Journal of Biochemistry, 68, 701–710 (1970)).

A DNA fragment containing lysC was amplified from chromosomal DNA in accordance with the PCR method (polymerase chain reaction; see White et al., Trends Genet., 5, 185 (1989)). As for DNA primers used for amplification, single strand DNA's of 23-mer and 21-mer having nucleotide sequences shown in SEQ ID NOs: 19 and 20 were synthesized in order to amplify a region of about 1,643 bp coding for lysC on the basis of a sequence known for

Figure 24:
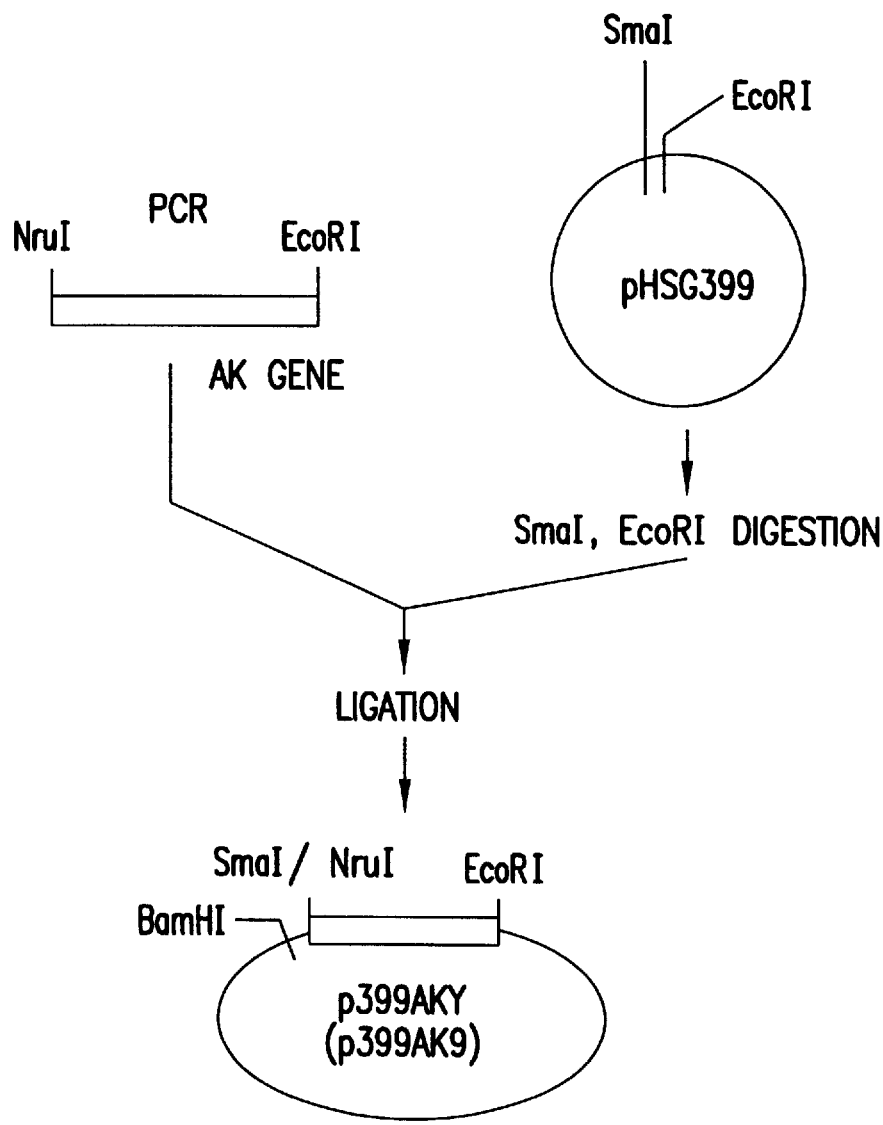
FIG. 24 is a view showing construction of the plasmid p399AK9.

*Corynebacterium glutamicum* (see Molecular Microbiology (1991), 5(5), 119714 1204; and Mol. Gen. Genet. (1990), 224, 317–324). The synthesis of DNA and the amplification of DNA were carried out by the conventional method. The sequence of the amplified DNA is shown in the sequence number 21. The amplified gene fragment of 1,643 kb was confirmed by agarose gel electrophoresis. After that, the fragment excised from the gel was purified in accordance with an ordinary method, and it was digested with restriction enzymes NruI and EcoRI.

pHSG399 was used as a cloning vector for the gene fragment. pHSG399 was digested with restriction enzymes SmaI and EcoRI, and it was ligated with the amplified lysC fragment. DNA was ligated by using DNA ligation kit in accordance with a designated method. Thus plasmids were prepared, in which the lysC fragments amplified from chromosomes of *Brevibacterium lactofermentum* were ligated with pHSG399 respectively. A plasmid comprising lysC from ATCC 13869 (wild type strain) was designated as p399AKY, and a plasmid comprising lysC from AJ3445 (L-lysine-producing bacterium) was designated as p399AK9 (FIG. 24).

(4) Preparation of dapB and construction of plasmid containing dapB

Figure 25:
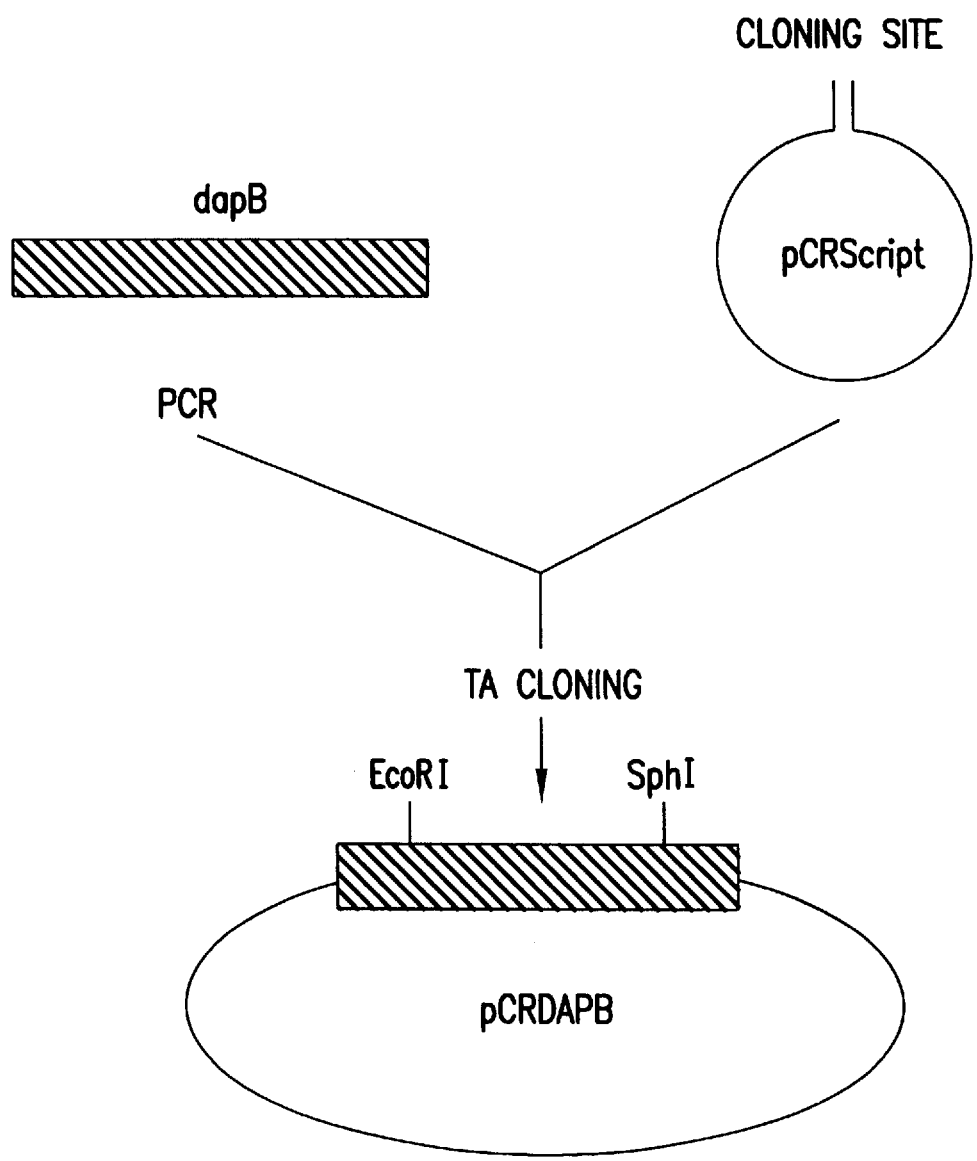
FIG. 25 is a view showing construction of the plasmid pCRDAPB.

A wild type strain of *Brevibacterium lactofermentum* ATCC 13869 was used as a chromosomal DNA donor. Chromosomal DNA was prepared from the ATCC 13869 strain in accordance with an ordinary method. A DNA fragment containing dapB was amplified from the chromosomal DNA in accordance with PCR. As for DNA primers used for amplification, DNA's of 23-mers having nucleotide sequences depicted in SEQ ID NOs: 22 and 23, respectively, were synthesized in order to amplify a region of about 2.0 kb coding for DDPR on the basis of a sequence known for *Brevibacterium lactofermentum* (see Journal of Bacteriology, 157(9), 2743–2749 (1993)). Synthesis of DNA and PCR were performed by the conventional method. The sequence of the amplified DNA is shown in the SEQ ID NO: 24. The amino acid sequence encoded by the DNA of SEQ ID:24 is listed as SEQ ID NO:32. pCR-Script (produced by Invitrogen) was used as a cloning vector for the amplified gene fragment of 2,001 bp, which was ligated with the amplified dapB fragment. Thus a plasmid was constructed, in which the dapB fragment of 2,001 bp amplified from chromosome of *Brevibacterium lactofermentum* was inserted into pCR-Script. The plasmid obtained as described above, which had dapB originating from ATCC 13869, was designated as pCRDAPB (FIG. 25).

A transformant strain AJ13107 obtained by introducing pCRDAPB into *E. coli* strain has been internationally deposited since May 26, 1995 under a deposition number of FERM BP-5114 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan) based on the Budapest Treaty.

(5) Construction of Plasmid Comprising Combination of Mutant lysC, dapA, and dapB p399DPS was cleaved with EcoRI and SphI to form blunt ends followed by extraction of a dapA gene fragment. This fragment was ligated with the p399AK9 having been digested with SalI and blunt-ended to construct a plasmid p399CA in which mutant lysC and dapA co-existed.

Figure 26A:
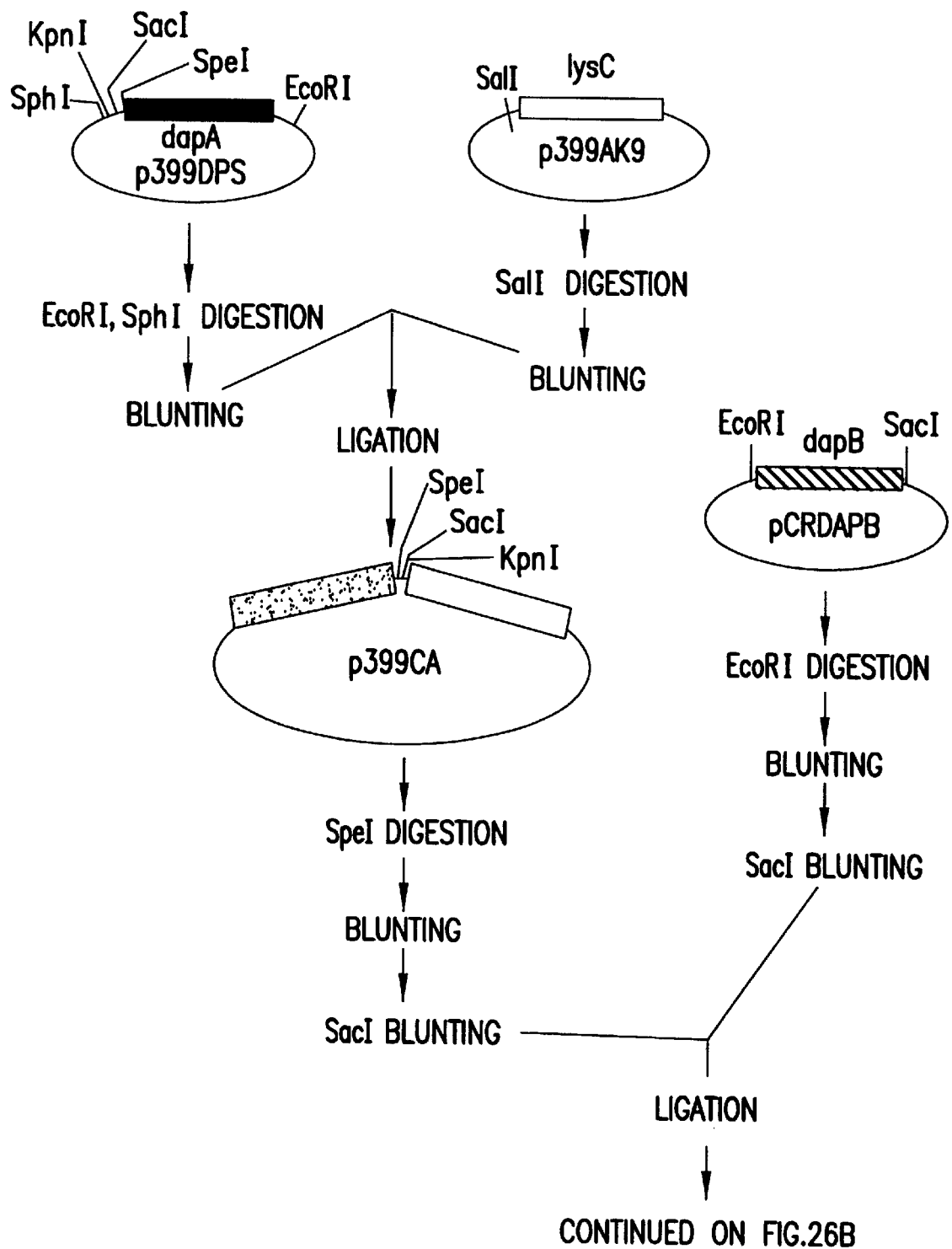
FIG. 26 is a view showing construction of the plasmid p399CAB and pCAB.

The plasmid pCRDAPB comprising dapB was digested with EcoRI and blunt-ended, followed by digestion with SacI to extract a DNA fragment of 2.0 kb comprising dapB. The plasmid p399CA comprising dapA and mutant lysC was digested with SpeI and blunt-ended, which was thereafter digested with SacI and ligated with the above-extracted 2.0 kb dapB fragment to obtain a plasmid comprising mutant lysC, dapA, and dapB. This plasmid was designated as p399CAB (FIG. 26).

Subsequently, p399CAB was cleaved with Sac II, and the cleaved fragment was end-blunted. Then, a fragment containing dap A and dapB was extracted therefrom. Meanwhile, pLYSAm was cleaved with Bam HI, and the cleaved fragment was end-blunted. These fragments were ligated with one another to produce a plasmid which contained dapA, dapB and lysA and which could be self-proliferated in coryneform bacteria. This plasmid is designated pABLm. The construction of pABLm is schematically shown in FIG. 21.

Transduction of the plasmid containing dapA, dapB and lysA into *Brevibacterium lactofermentum* Tn7156-Cint-Y2

The above-produced plasmid pABLm containing dapA, dapB and lysA was introduced into *Brevibacterium lactofermentum* Tn7156-Cint-Y2 by the electric pulse method (Japanese Laid-Open Patent Application (Kokai) no. 207, 791/1990 by Sugimoto et al.). The transformant was selected by the drug resistance marker and the kanamycin resistance gene of the plasmid and the tetracycline resistance gene amplified in the chromosome. Thus, the selection of the transformant was conducted in a complete culture medium containing 25 g/ml of kanamycin and 1.5 $\mu$g/ml of tetracycline. This transformant is designated Tn7156-Cint-Y2/pABLm.

Transduction of the Plasmid containing lysC, dapA, dapB and lysA into *Brevibacterium lactofermentum* wild strain A DNA fragment (hereinafter referred to as "Brevi.-ori") having an ability to make a plasmid autonomously replicable in bacteria belonging to the genus Corynebacterium was introduced into p399CAB.

Brevi.-ori was prepared from a plasmid vector pHK4 containing Brevi.-ori and autonomously replicable in cells of both *Escherichia coil* and bacteria belonging to the genus Corynebacterium. pHK4 was digested with restriction enzymes BamHI, and cleaved edges were blunt-ended. Blunt end formation was performed by using DNA Blunting kit in accordance with a designated method. After the blunt end formation, a phosphorylated Kpn I linker was ligated to make modification so that the DNA fragment corresponding to the Brevi.-ori portion might be excised from pHK4 by digestion with only Kpn I. This plasmid was digested with Kpn I, and the generated Brevi.-ori DNA fragment was ligated with p399CAB having been also digested with Kpn I to prepare plasmids containing the lysC, dapA and dapB genes and autonomously replicable in bacteria belonging to the genus Corynebacterium. The plasmid was designated as pCAB. The schematic flow of constructing pCAB is shown in FIG. 26.

pHK4 was constructed by digesting pHC4 with KpnI and BamHI, extracting a Brevi.-ori fragment, and ligating it with pHSG298 having been also digested with KpnI and BamHI (see Japanese Patent Laid-open No. 5-7491). pHK4 gives kanamycin resistance to a host. *Escherichia coli* harboring pHK4 was designated as *Escherichia coli* AJ13136, and deposited on Aug. 1, 1995 under a deposition number of FERN BP-5186 in National Institute of Bioscience and Human Technology of Agency of Industrial Science and Technology of Ministry of International Trade and Industry (postal code: 305, 1-3, Higashi 1-chome, Tsukuba-shi, Ibaraki-ken, Japan).

Figure 27:
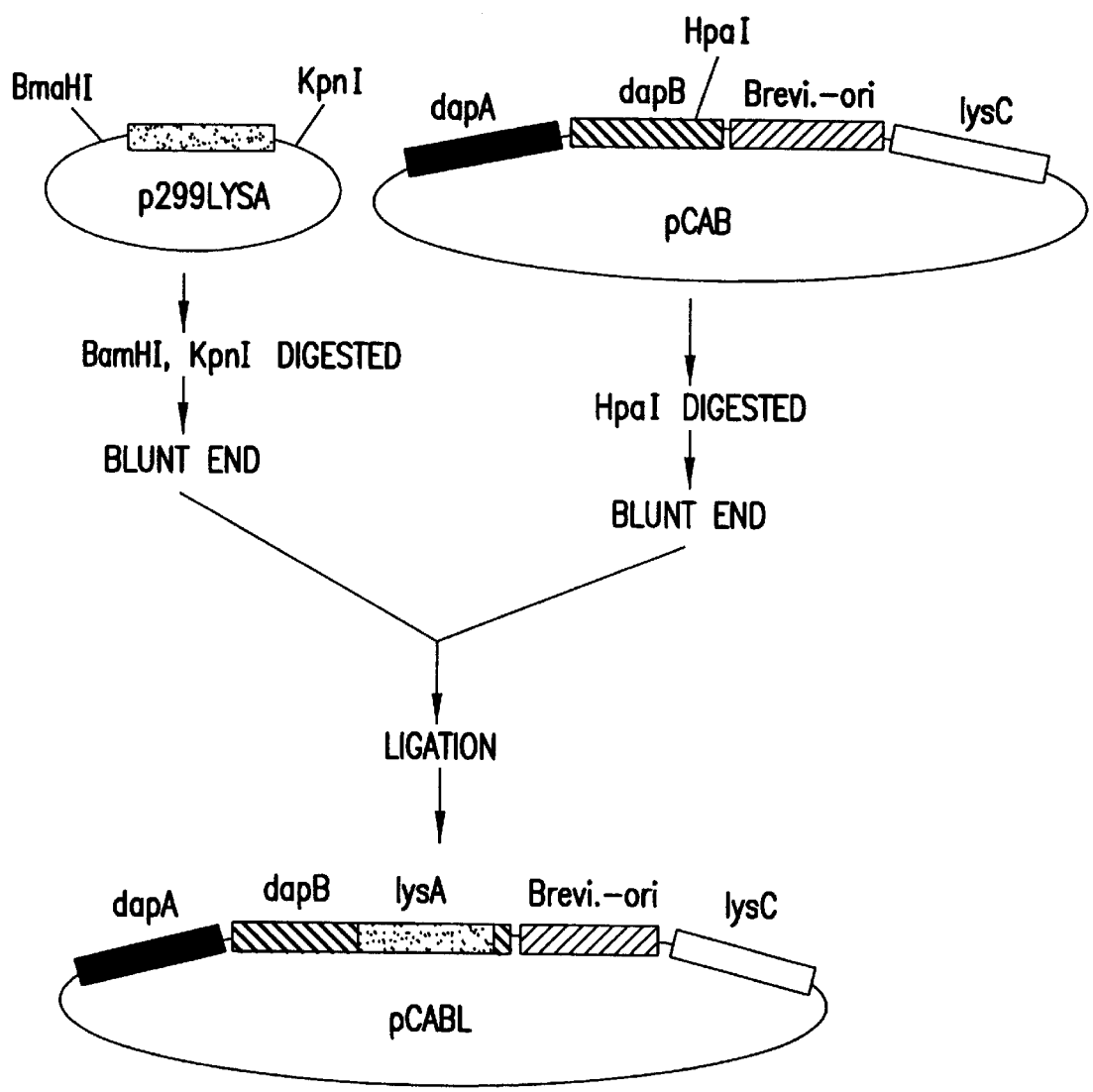
FIG. 27 is a view showing construction of the plasmid pCABL.

The plasmid p299LYSA comprising lysA was digested with KpnI and BamHI and blunt-ended, and then a lysA gene fragment was extracted. This fragment was ligated with pCAB having been digested with HpaI to construct a plasmid comprising a combination of mutant lysC, dapA, dapB, and lysA autonomously replicable in coryneform bacteria. The constructed plasmid was designated as pCABL. The process of construction of pCABL is shown in FIG. 27. It is noted that the lysA gene fragment is inserted into a HpaI site in a DNA fragment containing the dapB gene in pCABL, however, the HpaI site is located upstream from a promoter for the dapB gene (nucleotide numbers 611 to 616 in SEQ ID NO: 24), and the dapB gene is not decoupled.

The above-produced plasmid pCABL containing lysC, dapA, dapB and lysA was introduced into *Brevibacterium lactofermentum* wild strain AJ12036, and the selection of the transformant was conducted in a complete culture medium containing 5 μg/ml of chloramphenicol. This transformant is designated AJ12036/pCABL.

Evaluation of incubation of the above-constructed strain

Transformants AJ12036/pCABL and Tn7156-Cint-Y2/pABLm of *Brevibacterium lactofermentum* wild strain AJ12036 were incubated in an L-lysine-productive culture medium, and the amount of L-lysine produced therein was evaluated. The composition of the L-lysine-productive culture medium was as follows.

L-lysine-productive culture medium:

The following ingredients (in amounts per liter) except calcium carbonate were dissolved, and the solution was adjusted to a pH of 8.0 with KOH. The resulting solution was sterilized at 115° C. for 15 minutes, and 50 g of calcium carbonate which had been separately dry-sterilized were added thereto.

glucose 100 g $(NH_4)_2SO_4$ 55 g $KH_2PO_4$ 1 g $MgSO_4$ $7H_2O$ 1 g biotin 500 μg Thiamine 2000 μg $FeSO_4$ $7H_2O$ 0.01 g $MnSO_4$ $7H_2O$ 0.01 g nicotinamide 5 mg protein hydrolyzate (Mamenou) 30 ml calcium carbonate 50 g The parent strain and the transformant were inoculated in the culture medium having the above-mentioned composition, and were incubated at 31.5° C. while being shaken reciprocally. The amount of L-lysine produced after 72 hours of the incubation, the growth ($OD_{562}$) and the stability given when the incubation was completed are shown in Table 5. The growth was evaluated by diluting the solution to 101 times and measuring OD at 562 nm. Further, with respect to the stability, the culture solution in the completion of the incubation was grown in a complete culture medium after the dilution, and the colonies formed were put on a drug-containing plate, and the stability was indicated as growth rate of the colonies formed on the drug-containing plate.

TABLE 5

| Strain/plasmid | Growth | Amount of L-lysine produced (g/liter) | Stability (%) |
|---|---|---|---|
| AJ12036 | 0.700 | 0.0 | — |
| AJ12036/pCABL | 0.590 | 28.1 | 90 |
| Tn7156-Cint-Y2/pABLm | 0.608 | 28.5 | 100 |

As shown in Table 5, the amount of lysine produced was improved when using the strain in which lysC was increased in the plasmid as well as when using the strain in which lysC was increased in the chromosome. Further, the stability of AJ123036/pCABL was 90%, while that of AJ12036::C/ABLm was 100%.

Example 6

Construction of plasmid pHTN7150

Since the above-constructed artificial transposon Tn7145 carrying a kanamycin resistance gene did not have a suitable site for a dihydrodipicolinic acid synthase to be inserted, a new plasmid pHTN7150 into which a new insert site was introduced was constructed as follows.

A kanamycin resistance gene was cut out from plasmid vector pUC4K (available from Pharmacia Biotech) with a restriction enzyme Pst I and blunt-ended. The fragment containing the kanamycin resistance gene was inserted into the Sma I site of pHY300PLK (produced by Takara Shuzo) to construct pHY300-KM. Then pHY300-KM was digested with restriction enzymes Eco RI and Xba I to cut out a fragment containing a kanamycin resistance gene. This fragment was blunt-ended and inserted into the blunt-ended Nhe I site of IS714 on the plasmid pHIS714 to construct plasmid pHTN7150. The artificial transposon Tn7150 on pHTN7150 has a kanamycin resistance gene as a marker gene and a Bgl II site which can be used as a gene cloning site.

Combination of pHTN7150 and dapA gene of *Brevibacterium lactofermentum*

A gene encoding a dihydrodipicolinic acid synthase which is a lysine biosynthetase gene was inserted into artificial transposon pHTN7150 containing a kanamycin resistance gene in the following manner.

Figure 28:
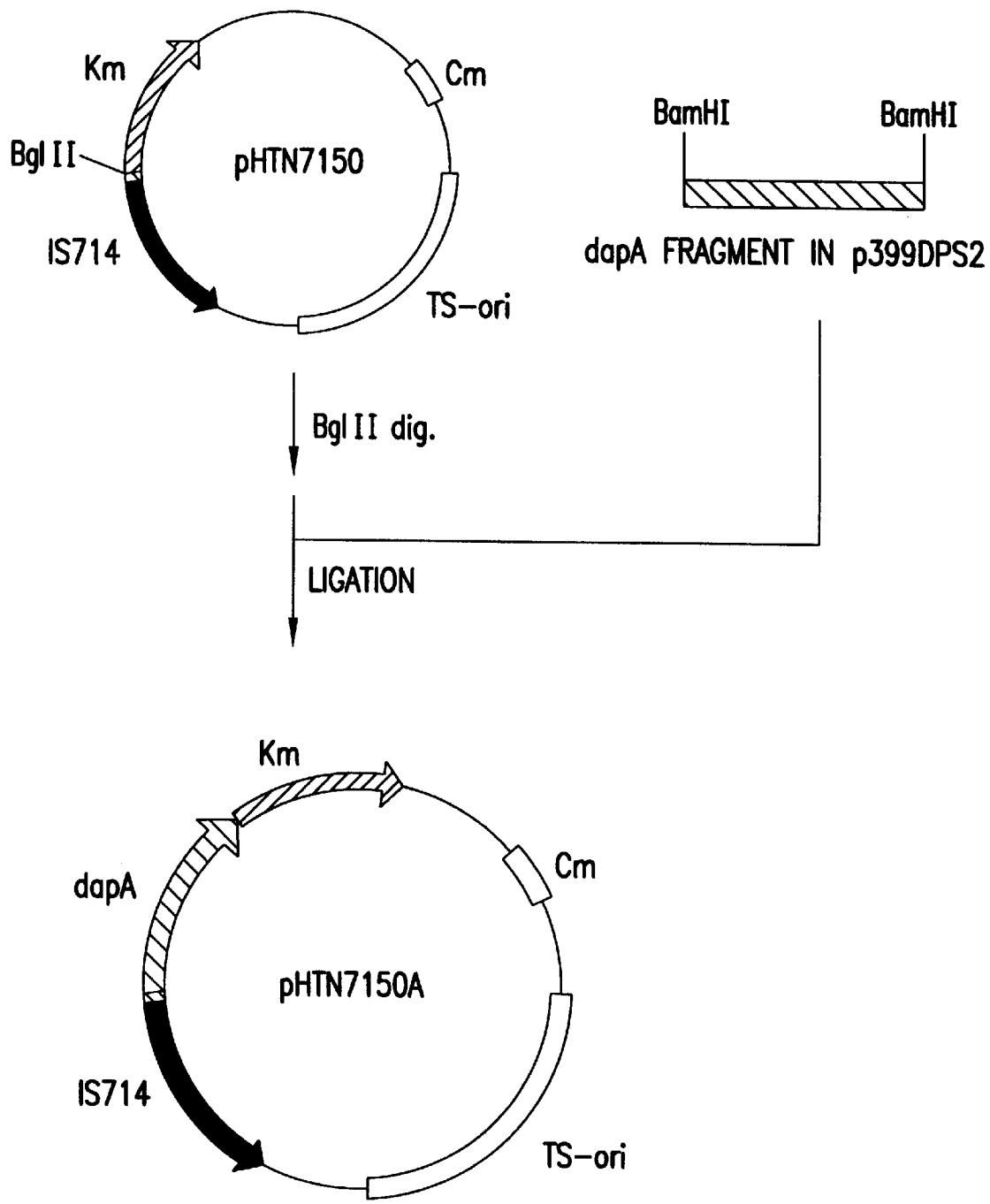
FIG. 28 is a view showing construction of the plasmid pHTN7150A.

After plasmid p399DPS containing dapA was cleaved with Eco RI, the resulting fragment was then end-blunted through the treatment with a T4 DNA polymerase, and a phosphorylated Bam HI linker (made by Takara Shuzo) was bound therewith to modify the fragment such that the dapA gene could be cut out with Bam HI alone. This plasmid is designated p399DPS2. A dapA fragment of 1.4 kb formed by cleaving this plasmid with Bam HI was combined with pHTN7150 cleaved with Bgl II that gives the same cohesive end as Bam HI. The thus-constructed plasmid is designated pHTN7150A. The construction of pHTN7150A is schematically shown in FIG. 28.

Transposition of the artificial transposon TN7150A into a chromosome of *Brevibacterium lactofermentum*

A strain formed by transposing the artificial transposon TN7150A containing dapA into *Brevibacterium lactofermentum* AJ12036 strain was obtained using pHTN7150A in the following manner.

The AJ12036 strain was transformed with pHTN7150A. The resulting transformant was incubated overnight at 25° C. in a CM2S liquid medium containing 25 μg/ml of kanamycin, 10 g/liter of yeast extract, 10 g/liter of tryptone, 5 g/liter of sucrose and 15 g/liter of NaCl. The culture was diluted approximately with a 0.9-% NaCl solution. The dilute was spread on the above-mentioned CM2S agar medium containing 25 μg/ml, and was incubated at 34° C. Chloramphenicol-sensitive strains were selected from among colonies formed, and some of these strains were randomly selected. Chromosomal DNAs were prepared therefrom, and subjected to the southern hybridization using the dapA fragment as a probe to identify the transposition of the artificial transposon. The above-obtained strain having transposed therein the artificial transposon is designated AJ12036::A.

Construction of pCBLmc and production of a strain

A plasmid containing variant lysC, dapB and lysA was constructed using pVC7, a shuttle vector of pAM330 and pHSG399 in the following manner. After pCRDAPB containing dapB was treated with Sac I, the resulting fragment was end-blunted through the treatment with a T4 DNA polymerase to construct a plasmid combined with a phosphorylated Pst I linker (made by Takara Shuzo). The thus-obtained plasmid is designated pCRDAPB2. This plasmid was cleaved with Bam HI and Pst I, and the resulting dapB fragment of 2.0 kb was inserted into pVC7 cleaved with Bam HI and Pst I. This plasmid is designated pBmc. pAK9 containing lysC was cleaved with Bam HI and Eco RI, and the resulting lysC fragment of 1.6 kb was connected to pBmC cleaved also with Bam HI and Eco RI to construct a plasmid containing dapB and lysC. This plasmid is designated pBCmc.

Figure 29A:
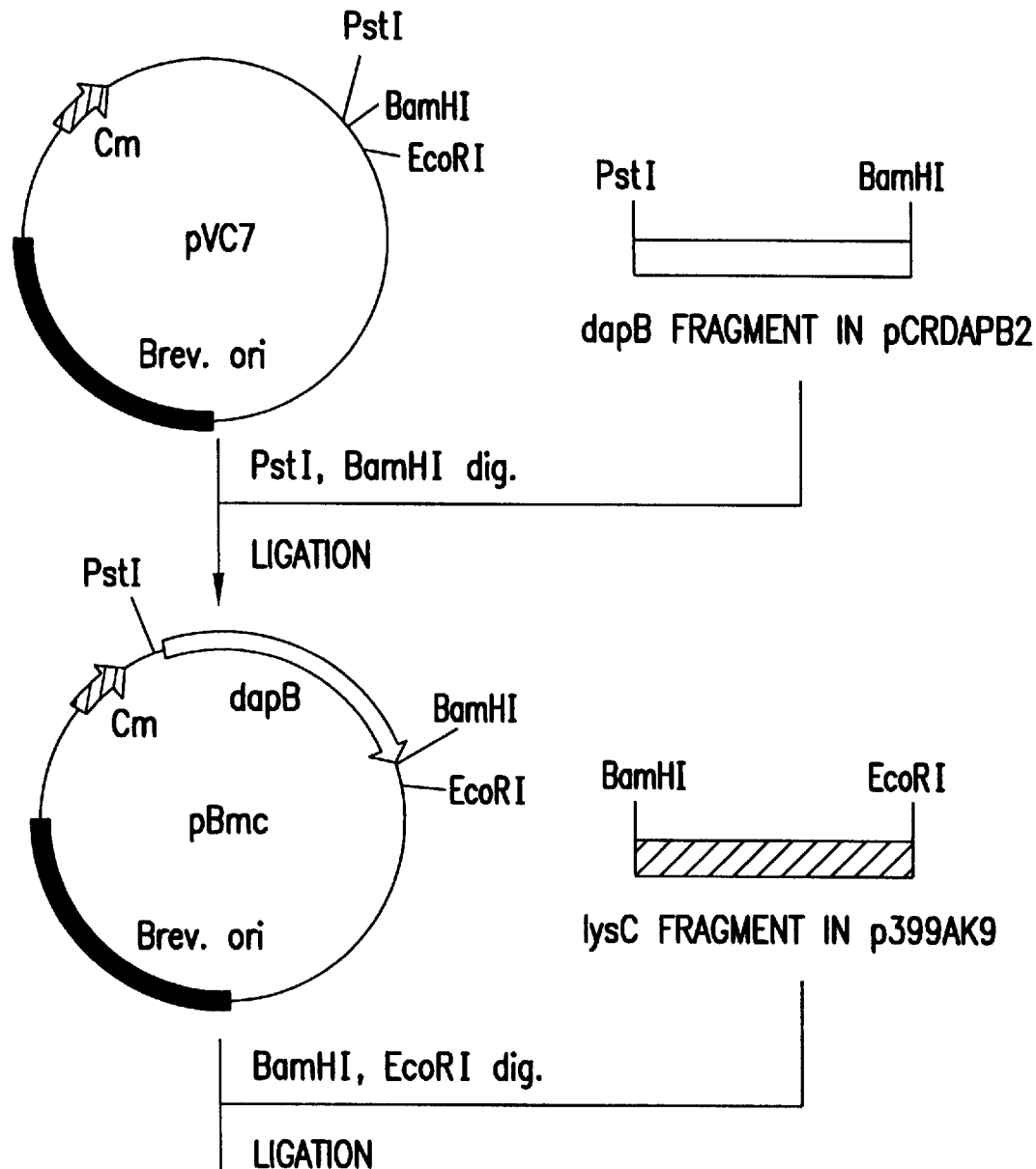
FIG. 29 is a view showing construction of the plasmid pCBLmc.

After p399LYSA containing lysA was cleaved with Eco RI, the resulting fragment was end-blunted through the treatment with a T4 DNA polymerase, and was combined with a phosphorylated Kpn I linker to modify it such that lysA was cleaved with Kpn I. This plasmid is designated p399LYSA2. p399LYSA2 was cleaved with KpnI. The resulting lysA fragment of 3.6 kb was ligated with pBCmc having been digested with Eco RI, end-blunted through the treatment with a T4 DNA polymerase, and combined with the phosphorylated Kpn I linker. The thus-obtained plasmid is designated pCBLmc. This plasmid was self-replicable in *E. coli* and coryneform bacteria, imparted chloramphenicol resistance to a host, and contained mutant lysC, dapB and lysA. The construction of pCBLmc is schematically shown in FIG. 29.

The above-constructed pCBLm was introduced into the AJ12036::A strain in which the artificial transposon Tn7150A had been transposed into the chromosome by the electric pulse method (Japanese Laid-Open Patent Application (Kokai) No. 207,791/1990 by Sugimoto et al.). The selection of the transformants was conducted in the above-mentioned CM2S medium containing 5 μg/ml of chloramphenicol and 25 μg/ml of kanamycin. The thus-constructed stain is designated AJ12036::A/pCBLmc.

Evaluation of incubation of the strains constructed

The parent strain and the transformants AJ12036/pCABL and AJ12036::A/pCBLmc were incubated in a L-lysine-productive culture medium, and the amount of lysine produced was evaluated. The results are shown in Table 6.

TABLE 6

| Strain/plasmid | Growth | Amount of L-lysine produced (g/liter) | Stability (%) |
| --- | --- | --- | --- |
| AJ12036 | 0.700 | 0.0 | — |
| AJ12036/pCABL | 0.590 | 28.1 | 90 |
| AJ12036::A/pABLm | 0.595 | 28.7 | 100 |

As is apparent from Table 6, the amount of lysine produced was improved in the strain in which dapA was increased in the chromosome as was seen in the strain in which lysC was increased in the plasmid. Further, the stability of AJ12036/pCABL was 90%, while that of AJ12036::A/pCBLm was 100%.

Example 7

Construction of an artificial transposon containing no transposase in a transposon unit and construction of a transposase expression plasmid using an *E. coli* Trc promoter or the like Plasmid pHIS714 was cleaved with restriction endonucleases Nhe I and Xba I to obtain a fragment containing a gene encoding a transposase from which a 5'-side inverted repeat (IR) of IS714 was deleted. This DNA fragment was introduced into an Xba I site of plasmid vector pUC19 to construct plasmid TnpL/pUC19.

Further, TnpL/pUC19 was cleaved with restriction endonucleases Mro I and Xba I to delete a sequence including a termination codon of IS714 and a 3'-side inverted repeat (IR). A synthetic double-stranded DNA having the following sequence was inserted into the above-cleaved portion through ligation.

5'-CCGGACAGCTCACCCACAAAATCAATGCACTC-TAAAAAGGTACCT-3' (SEQ ID NO: 25)

3'-TGTCGAGTGGGTGTTTTAGTTACGTGAGATTT-TTCCATGGAGATC-5' (SEQ ID NO: 26)

In this manner, plasmid ORFL/pUC19 was constructed in which IR present in the transposase 3'-side of TnpL/pUC19 was deleted.

Subsequently, this ORFL/pUC19 was cleaved with restriction endonucleases Sma I and Xba I to obtain a gene fragment of approximately 1.5 kb containing the transposase. This transposase gene fragment was inserted into a portion of plasmid vector pHY300PLK (made by Takara Shuzo) obtained by removing a sequence between Sma I and Xba I sites thereof, and was then cut out with restriction endonucleases Eco RI and Kpn I. This Eco RI-Kpn I transposase gene fragment was end-blunted with a T4 DNA polymerase. Meanwhile, plasmid vector pHSG398 (made by Takara Shuzo) was partially digested with restriction endonuclease Pvu II to delete a fragment of approximately 0.3 kb containing a multicloning site. The above-obtained transposase gene fragment was inserted into the digested portion of plasmid vector pHSG398 to construct plasmid pORF1 as shown in FIG. 10.

On the other hand, the Nhe I-Xba I cleavage fragment of plasmid pHIS714 which had been obtained earlier was end-blunted, and introduced into the end-blunted Pst I site of plasmid vector pUC19 to construct plasmid Tnp (Pst)/pUC19.

The transposase gene of this Tnp(Pst)/pUC19 was subjected to the partial base substitution using a U. S. E. Mutagenesis Kit (made by Pharmacia Biotech). The base substituted was G which was the 288th base in the sequence of IS714. This base G was replaced with C.

This was a change from GTG to GTC, and it was not a change of an amino-acid level. This base-substituted plasmid is designated Tnp(Pst)M/pUC19.

The sequence between restriction endonuclease Sma I and Nae I sites present in the transposase first half gene was deleted from pORF1. The transposase first half gene fragment (including the change GTG GTC) obtained by cleaving Tnp(Pst)M/pUC19 with restriction endonucleases Sma I and Nae I was inserted into the above-deleted portion through ligation to construct pORF2.

The sequence between the Sma I and Xba I sites was deleted from pORF2, and the resulting fragment was end-blunted. A DNA fragment containing a tryptophan operon attenuator was obtained by cleaving pBSF2-SD7 with restriction endonucleases Nae I and Hind III, and was then end-blunted. The former fragment was ligated with the latter fragment. The thus-constructed plasmid is designated pORF3.

E. coli HB101 transformed with plasmid pBSF2-SD7 (AJ12448) was listed as deposited at the National Institute of Bioscience and Human Technology of the Agency of Industrial Science and Technology, Ministry of International Trade and Industry, (1-3, Higashi 1 Chome Tsukuba-shi Ibaraki-ken 305, Japan) under deposit No. FERM P-10758 on Jun. 1, 1989. The strain was transferred to the deposit based on the Budapest Treaty on Feb. 19, 1992. Deposit No. BP-3753 is allotted thereto.

pORF3 was cleaved with restriction endonucleases Sal I and Bpu 1102I to delete the transposase first half gene fragment. The transposase first half gene fragment obtained by cleaving Tnp(Pst)/pUC19 with restriction endonucleases Sal I and Blu ll02I was inserted into the above-deleted portion by ligation to construct pORF4 as shown in FIG. 11.

TnpL/pUC19 was cleaved with Sac I, and was then digested with BAL 31 nuclease at 30° C. for 20 minutes to delete a sequence near the initiation codon of the transposase gene from the upstream side. After the ends which underwent the deletion were blunted, the transposase gene fragment was cut out using the Sph I site, and was inserted into a site of pHSG398 which was cleaved with Sma I and Sph I. The thus-constructed plasmid is designated delTnp5/398.

This delTnp5/398 was cleaved with restriction endonucleases Knp I and Hind III, and the resulting transposase first half gene fragment was end-blunted. Then, plasmid vector pKK233-2 (made by Pharmacia Biotech) was cleaved with Nco I and Hind III, and was end-blunted. The former fragment was ligated with the latter fragment though ligation to construct pTrc-ORF. pTrc-ORF was cleaved with Ssp I and Bpu 1102I to form a fragment containing Trc promoter and the transposase first half gene. pORF3 was cleaved with Xba I, end-blunted, and further cleaved with Bpu 1102I to delete the transposase first half gene fragment. The above-formed fragment was inserted into this deleted portion of pORF3 to construct pORF7 as shown in FIG. 12.

The transposase first half gene fragment obtained by cleaving delTnp5/398 with restriction endonucleases Kpn I and Hind III was cloned between the KpnI and Hind III sites of plasmid vector pUC18.

The portion between the Bsm I and Nae I sites of this plasmid was deleted, and the fragment was ligated with the transposase first half gene fragment (G C substitution type) obtained by cleaving Tnp(Pst)M/pUC19 with restriction endonucleases Bsm I and Nae I to construct delTnp5M/18.

This delTnp5M/18 was cleaved with Kpn I and Hind III, and the resulting transposase first half gene fragment was end-blunted. pKK233-2 was cleaved with Nco I and Hind III, and the resulting fragment was end-blunted. These fragments were ligated with each other to construct pTrc-TnpM. pORF8 was constructed from pTrc-TnpM by the method of constructing pORF7 from pTrc-Tnp (FIG. 13). Construction of a plasmid for introduction of a coryneform bacterium containing an artificial transposon unit and a transposase expression system outside this unit Plasmids were constructed using the above-mentioned plasmids pORF3, pORF4, pORF7 and pORF8. The construction of pORF41 from pORF3 is described below.

First, pHIS714 was cleaved with Nhe I and Sac II to delete the major part of the transposase gene. A double-stranded synthetic DNA having the following sequence was inserted into the above-deleted portion to construct pHTN7160.

5'-CTAGCTCGAGATATCAGATCTACTAGTCGAC-CGC-3' (SEQ ID NO: 27)
3'-GAGCTCTATAGTCTAGATGATCAGCTGG-5' (SEQ ID NO: 28)

pHTN7160 was cleaved with restriction endonuclerase Kpn I, end-blunted, and then cleaved again with Bgl I to obtain a fragment containing inverted repeats (IR) on both sides of IS714 and a temperature-sensitive replication origin that functions within a coryneform bacterium.

pORF3 was cleaved with restriction endonuclease Ear I, end-blunted, and then cleaved again with Bgl I. The above-mentioned fragment of pHTN7160 was inserted therein to construct pORF41-pre.

Then, pORF41-pre was cleaved with Eco RV. An Eco RI-Ava I fragment which contained the Tc resistance gene of pBR322 and was end-blunted was inserted into the Eco RV-cleaved fragment to construct pORF41 as shown in FIG. 14.

The above-mentioned method was repeated to construct pORF31 from pORF4 through pORF31-pre, pORF71 from pORF7 through pORF71-pre, and pORF81 from pORF8 through pORF81-pre, respectively.

Figure 15:
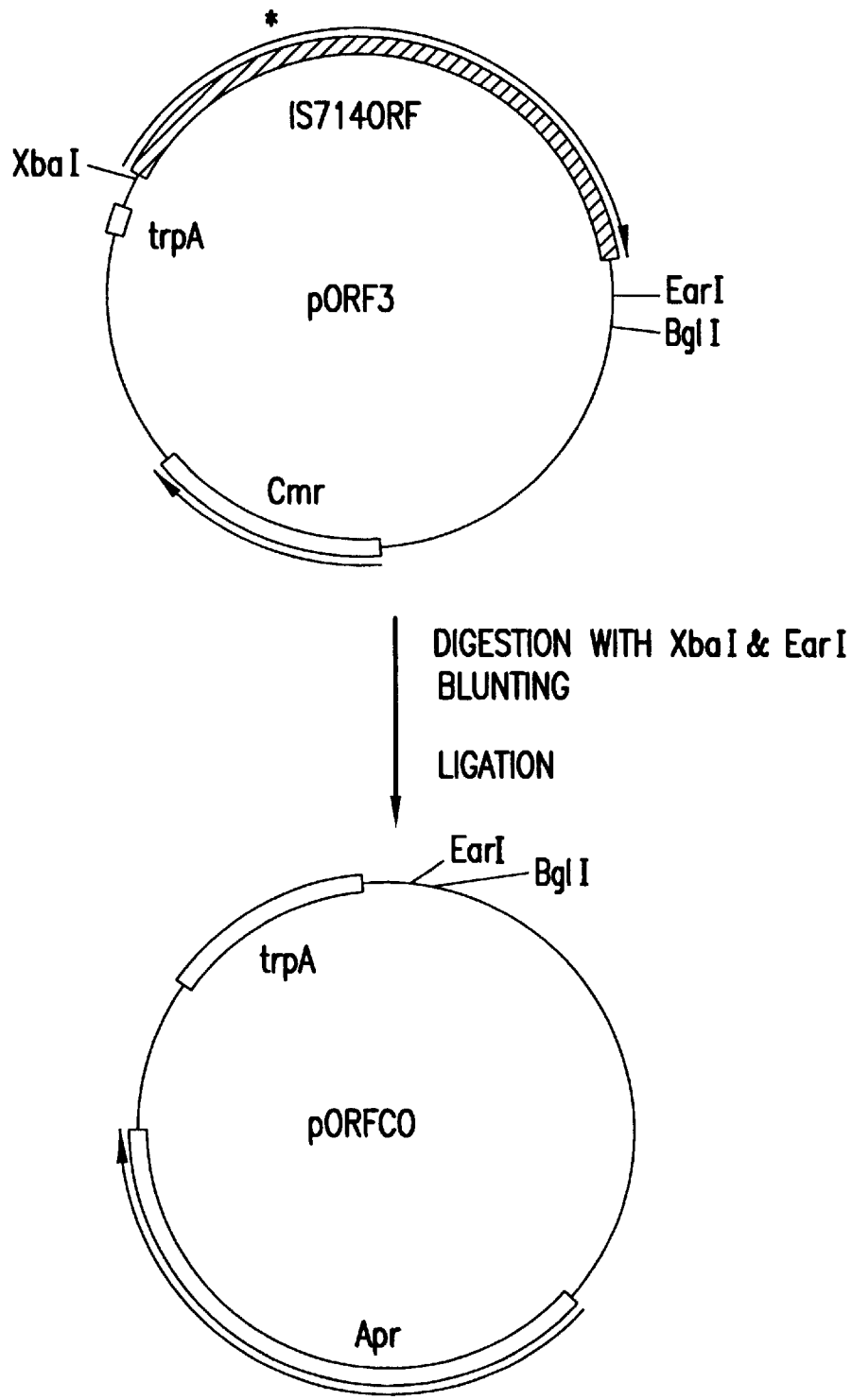
FIG. 15 is a view showing construction of the plasmid pORFC0.

E. coli AJ13208 harboring plasmid pORF81 was listed as deposited at the National Institute of Bioscience and Human Technology of the Agency of Industrial Science and Technology, Ministry of International Trade and Industry, (1-3, Higashi 1 Chome Tsukuba-shi Ibaraki-ken 305, Japan) based on the Budapest Treaty on Jun. 3, 1996. Deposit No. BP-5557 is allotted thereto.

pORF3 was cleaved with Xba I and Ear I, end-blunted, and self-ligated to construct pORFC0 containing no transposase gene (FIG. 15).

pORFC2 composed only of a transposon unit (containing no transposase gene) was constructed from pORFC0 through pORFC2-pre in the same manner as in constructing pORF41 form pORF3.

These finally constructed plasmids had the structural gene of the transposase, the Cm resistance gene, the replication origin that functions within E. coli, the temperature-sensitive replication origin that functions within a coryneform bacterium and the Tc resistance gene held between IRs of IS714, provided pORFC2 had no structural gene of the transposase.

The unit containing IRs on both ends of IS714 and the Tc resistance gene is designated transposon unit Tn7162. Evaluation of the number of copies of the transposon unit having the Tc resistance gene in the chromosome which was formed by transposition of the transposon unit The test of transposition was conducted using pORF31, pORF41, pORF81 and pORFC2 of the above-constructed plasmids. The unit considered to be transposed was transposon unit Tn7162.

Brevibacterium lactofermentum AJ12036 was transformed with each of the above-mentioned plasmids, and the number of copies of transposon unit Tn7162 in the host chromosome which were formed by the transposition of transposon unit Tn7162 into the host chromosome was evaluated. That is, the transformant was incubated overnight at 25° C. in the above-mentioned CM2G liquid medium containing 5 μg/ml of Cm, and was appropriately diluted with a 0.9-% NaCl solution. The dilute was spread on the above-mentioned CM2G agar medium containing from 1.5 μg/ml to 4 μg/ml of Tc in an amount of 100 μl, and was incubated at 34° C. Cm-sensitive clones were selected from among the colonies formed, and were incubated at 34° C. Some of the clones were randomly selected from among the colonies formed. Chromosomal DNAs were produced therefrom, completely digested with restriction endonuclease Pvu II, subjected to agarose gel electrophoresis, and blotted on a nitrocellulose (or nylon or PVDF) filter. This filter was subjected to the southern hybridization using, as a probe, a Tc resistance gene fragment labelled with 32-P or with an ECL direct labelling system (made by Amersham), and the number of bands hybridized with the probe was detected.

Consequently, it was found, as shown in Table 7, that a large number of copies of transposon unit Tn7162 having the Tc resistance marker gene were transposed at some frequency.

This proved that the expression-type transposase gene functioned either outside the transposon unit in the plasmid (pORF31, 41 and 81) or in the transposase inherently present in the chromosome (pORFC2).

TABLE 7

| Plasmid | Selective Tc concentration (μg/ml) | Number of copies of Tc resistance gene |
|---|---|---|
| pORFC2 | 1.5 | >8 |
|  | 2.0 | >12 |
| pORF31 | 2.0 | >7 |
| pORF41 | 1.5 | >11 |
| pORF81 | 1.5 | 3 |
|  |  | 4 |
|  |  | 10 |
|  |  | 11 |
|  | 2.0 | 3 |
|  |  | 4 |
|  |  | 4 |
|  | 4.0 | 5 |

Example 8
Construction of a plasmid for coryneform bacteria containing a transposase expression system alone and transposition of a transposon unit on a chromosome
Construction of a plasmid for coryneform bacteria containing a transposase expression system alone Plasmid pHIS714K1 was cleaved with EcoO 109I and Mro I to delete IS714, and was then self-ligated to construct pHIS714Kdel. Meanwhile, pORF3 was cleaved with restriction endonuclease Ear I, end-blunted, and cleaved again with Bgl I. pHIS714Kdel was cleaved with restriction endonuclease Kpn I, end-blunted, and then cleaved again with Bgl I to form a fragment which contained a temperature-sensitive replication origin and which functioned within coryneform bacteria. The thus-formed fragments are ligated with each other to construct pORF40 as shown in FIG. 17.

This method was repeated to construct pORF30 from pORF4, pORF70 from pORF 7, pORF80 from pORF 8 and pORFC1 from pORFC0 respectively.

Evaluation of the number of copies of the transposon unit having the Tc resistance gene in the chromosome which were formed by transposition of the transposon unit The test of transposition was conducted using pORF80 and pORFC1 of the above-constructed plasmids. The unit considered to be transposed was transposon unit Tn7162.

In Example 7, it was demonstrated that *Brevibacterium lactofermentum* AJ12036 was transformed with the plasmid containing transposon unit Tn7162, and a large number of copies of Tn7162 were transposed into the host chromosome. It was tested through the southern hybridization analysis of the chromosomal DNA whether Tn7162 in the chromosome was further transposed or replicated when the above-constructed plasmids pORF80 and pORFC1 were further transduced into one copy of the chromosome transposition strain obtained here as a host to increase the transposase activity. Then, the number of copies was evaluated.

That is, the transformant was incubated overnight at 25° C. in the above-mentioned CM2G liquid medium containing 5 μg/ml of Cm, and then appropriately diluted with a 0.9-% NaCl solution. The dilute was spread on the above-mentioned CM2G agar medium containing from 6 μg/ml to 20 μg/ml of Tc in an amount of 100 l, and was incubated at 34° C. Cm-sensitive clones were selected from among colonies formed.

Some clones were randomly selected from among these Cm-sensitive clones. Chromosomal DNAs were prepared therefrom, completely digested with restriction endonuclease Pvu II, subjected to agarose gel electrophoresis, and blotted on a nitrocellulose (or nylon or PVDF) filter. This filter was subjected to the southern hybridization using, as a probe, a Tc resistance gene fragment labelled with $^{32}$-p or with an ECL direct labelling system (made by Amersham), and the number of bands hybridized with this probe was detected.

As a result, a large number of copies of transposon unit Tn7162 having the Tc resistance marker gene were transposed and replicated at some frequency.

Having now fully described the invention, it will be apparent to one of ordinary skill in the art that many changes and modifications can be made thereto without departing from the spirit or scope of the invention as set forth herein.

The application is based on Japanese application No. 166541/1995, filed on Jun. 30, 1995. The full text of that Japanese application is incorporated herein by reference.

What is claimed as new and is desired to be secured by Letter Patent of the United States is:

1. A method of producing a transformed coryneform bacterium containing multiple copies of a desired gene comprising the steps of:

(1) constructing an artificial transposon containing:
 (a) the desired gene;
 (b) a drug resistance gene; and
 (c) an insertion sequence comprising a pair of inverted repeats, wherein the desired gene and the drug resistance gene are located between the pair of inverted repeats; and (2) contacting a starting coryneform bacterium with the artificial transposon, thereby:
 (a) causing the artificial transposon to be transposed into the genetic material of the starting coryneform bacterium, (b) causing multiple copies of the desired gene and the drug resistance gene to be inserted into the genetic material of the starting coryneform bacterium; and (c) producing the transformed coryneform bacterium.

2. The method of claim 1, wherein the artificial transposon further contains a transposase gene located between the pair of inverted repeats.

3. The method of claim 2, wherein the insertion sequence and the transposase gene are derived from a coryneform bacterium.

4. The method of claim 1, wherein the insertion sequence comprises the nucleotide sequence of SEQ ID NO:1, SEQ ID NO:5, or SEQ ID NO:9.

5. The method of claim 1, wherein the drug resistance gene is a chloramphenicol resistance gene or a tetracycline resistance gene.

6. The method of claim 1, wherein the desired gene encodes an enzyme which participates in the synthesis of an amino acid.

7. The method of claim 6, wherein the enzyme is an aspartokinase or a dihydropicolinic acid synthetase.

8. The method of claim 1, wherein the genetic material is a chromosome.

9. A transformed coryneform bacterium containing multiple copies of a desired gene, wherein the transformed coryneform bacterium is produced by the method of claim 1.

10. A transformed coryneform bacterium containing multiple copies of a desired gene, wherein the transformed bacterium is produced by the method of claim 6.

11. A method for obtaining an amino acid comprising the steps of:

(1) incubating the transformed corynebacterium of claim 10 in a culture medium, thereby causing the transformed corynebacterium to produce (a) the enzyme which participates in the synthesis of the amino acid, and (b) the amino acid; and (2) recovering the amino acid from the culture medium, thereby obtaining the amino acid.

12. The method of claim 11, wherein the enzyme is an aspartokinase or a dihydropicolinic acid synthetase.

* * * * *

UNITED STATES PATENT AND TRADEMARK OFFICE
CERTIFICATE OF CORRECTION

PATENT NO. : 5,804,414

DATED : September 8, 1998

Page 1 of 2

INVENTOR(S): Mika MORIYA et al.

Figure 9B:
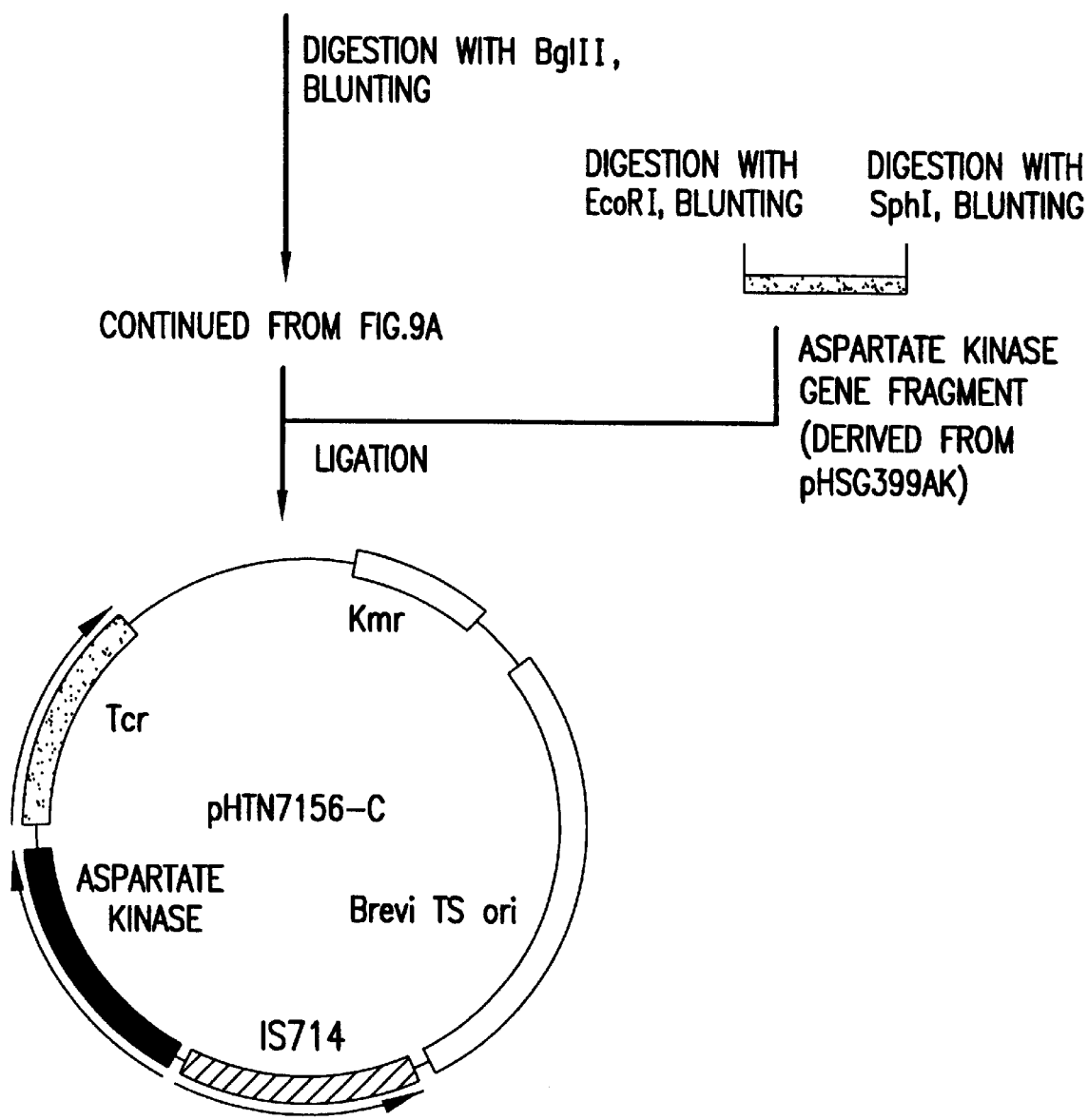
Figure 10B:
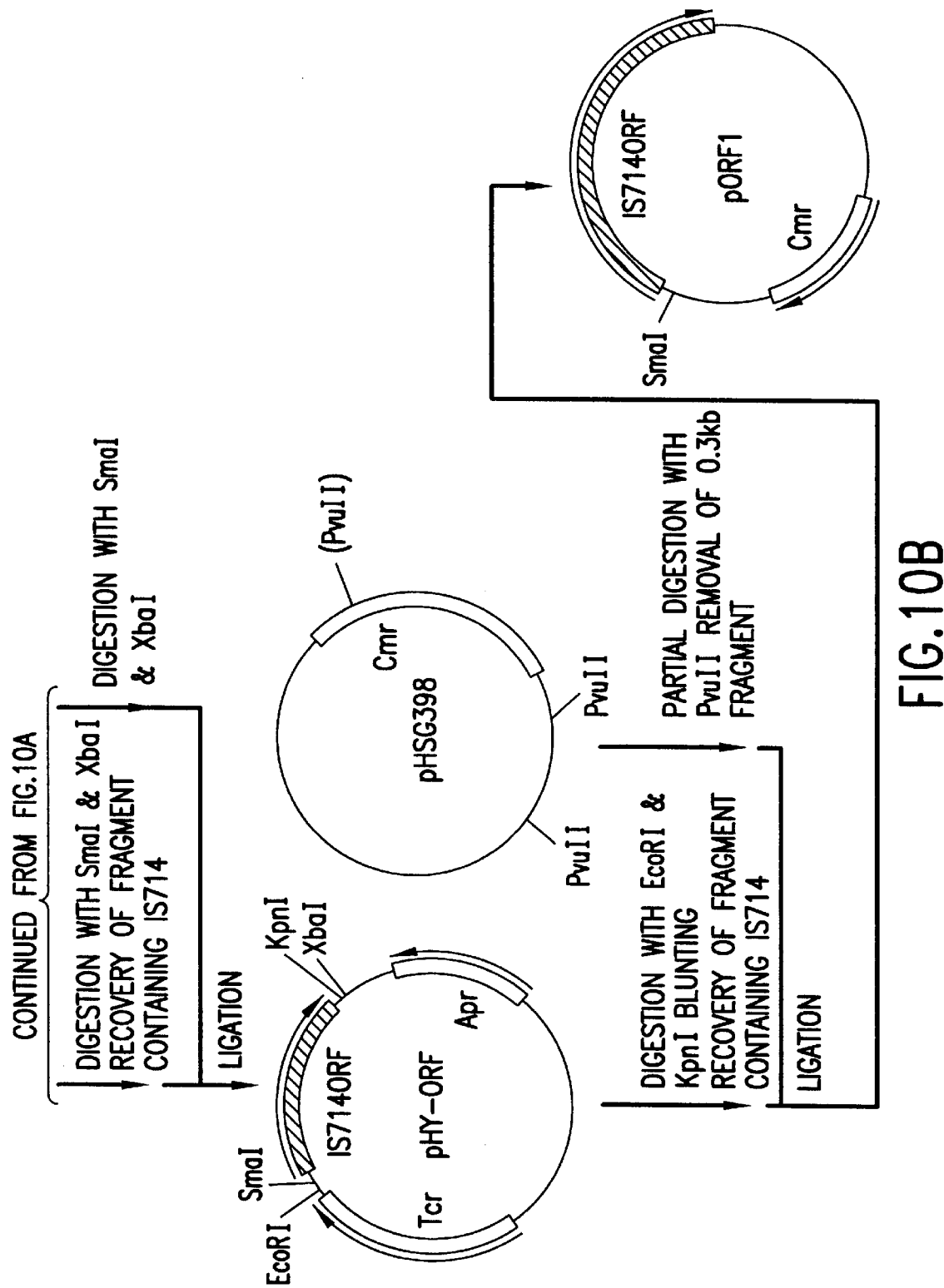
Figure 11A:
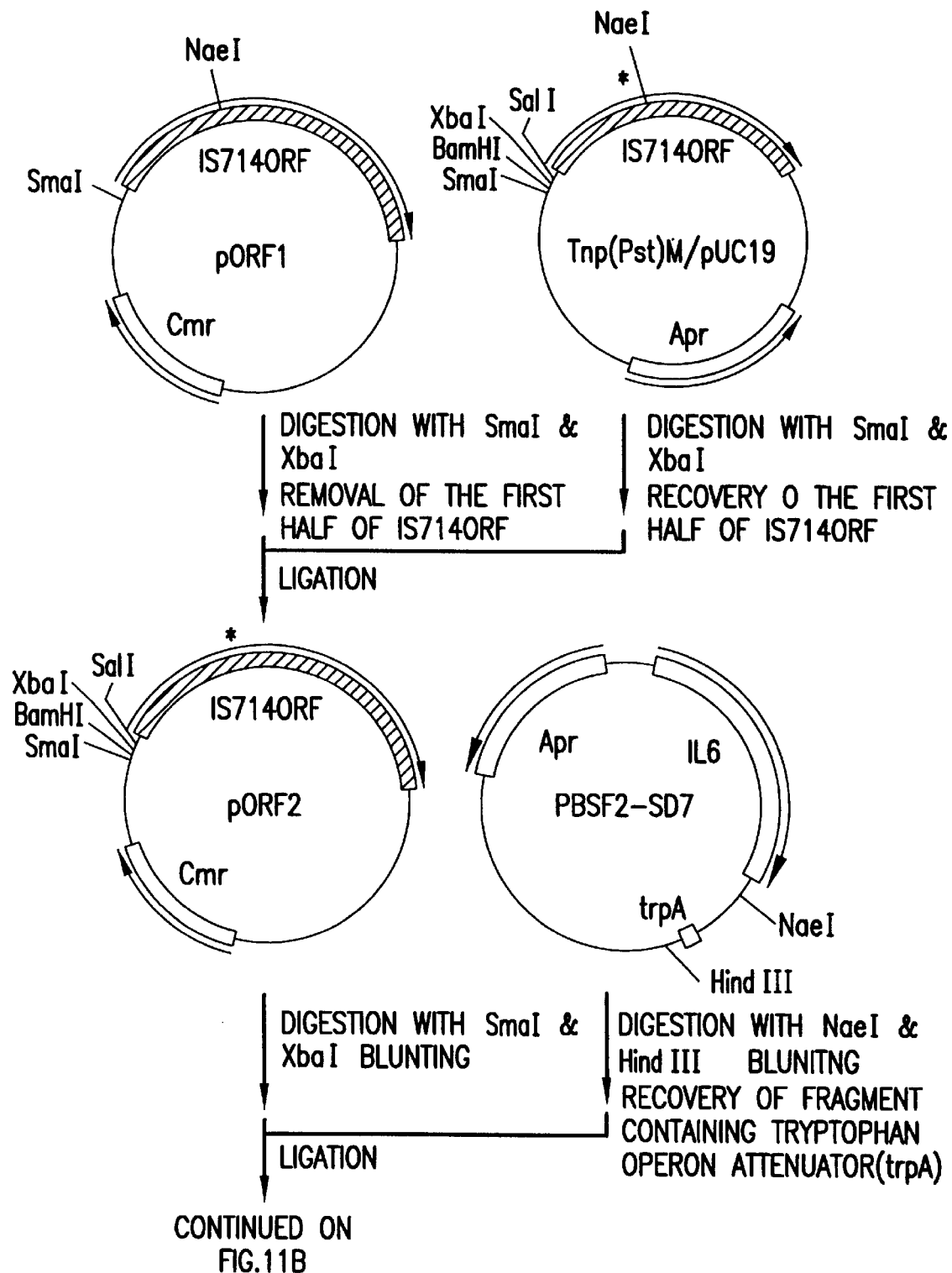
FIG. 11 is a view showing construction of the plasmids pORF3 and pORF4.
Figure 11B:
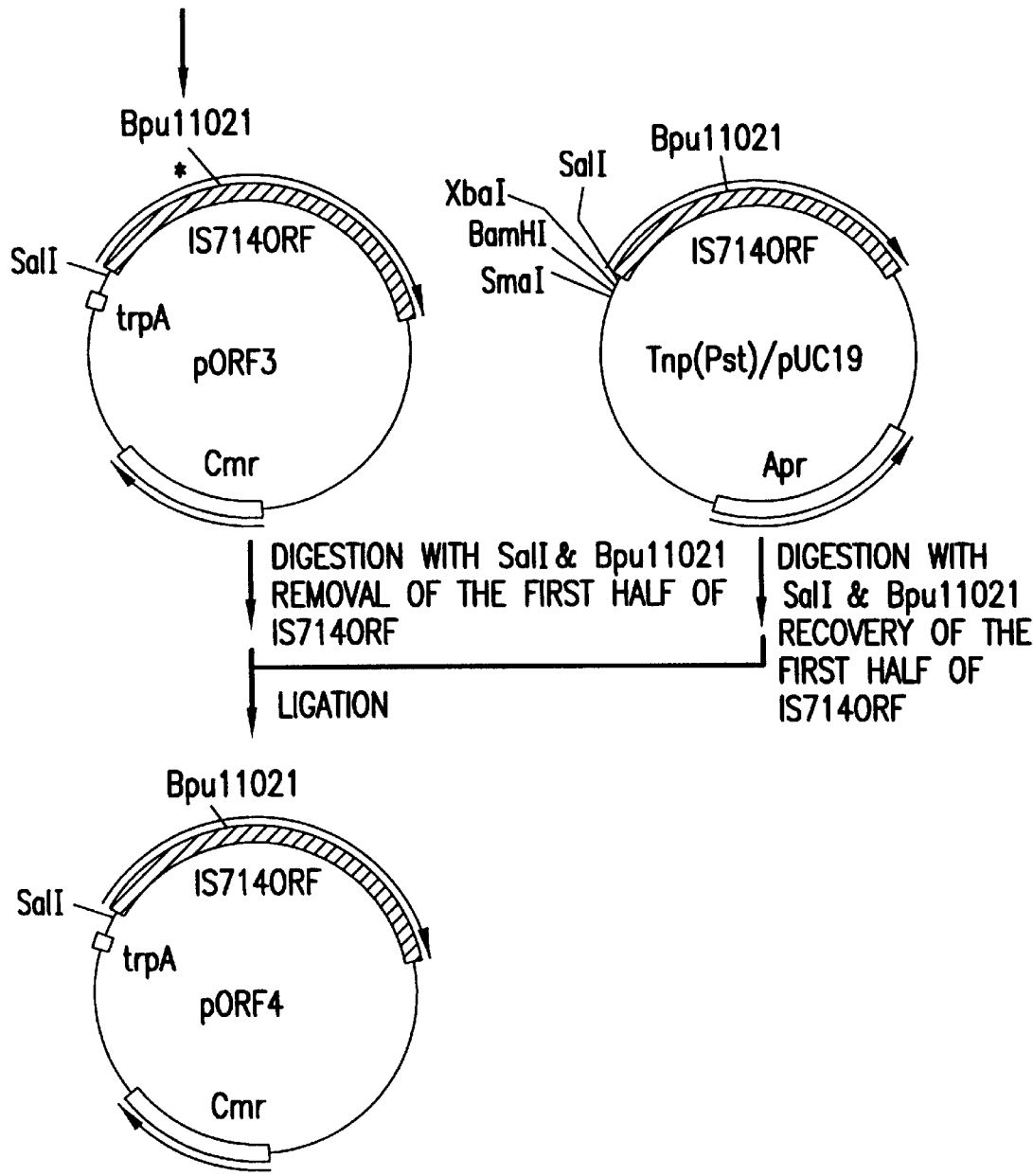
Figure 12B:
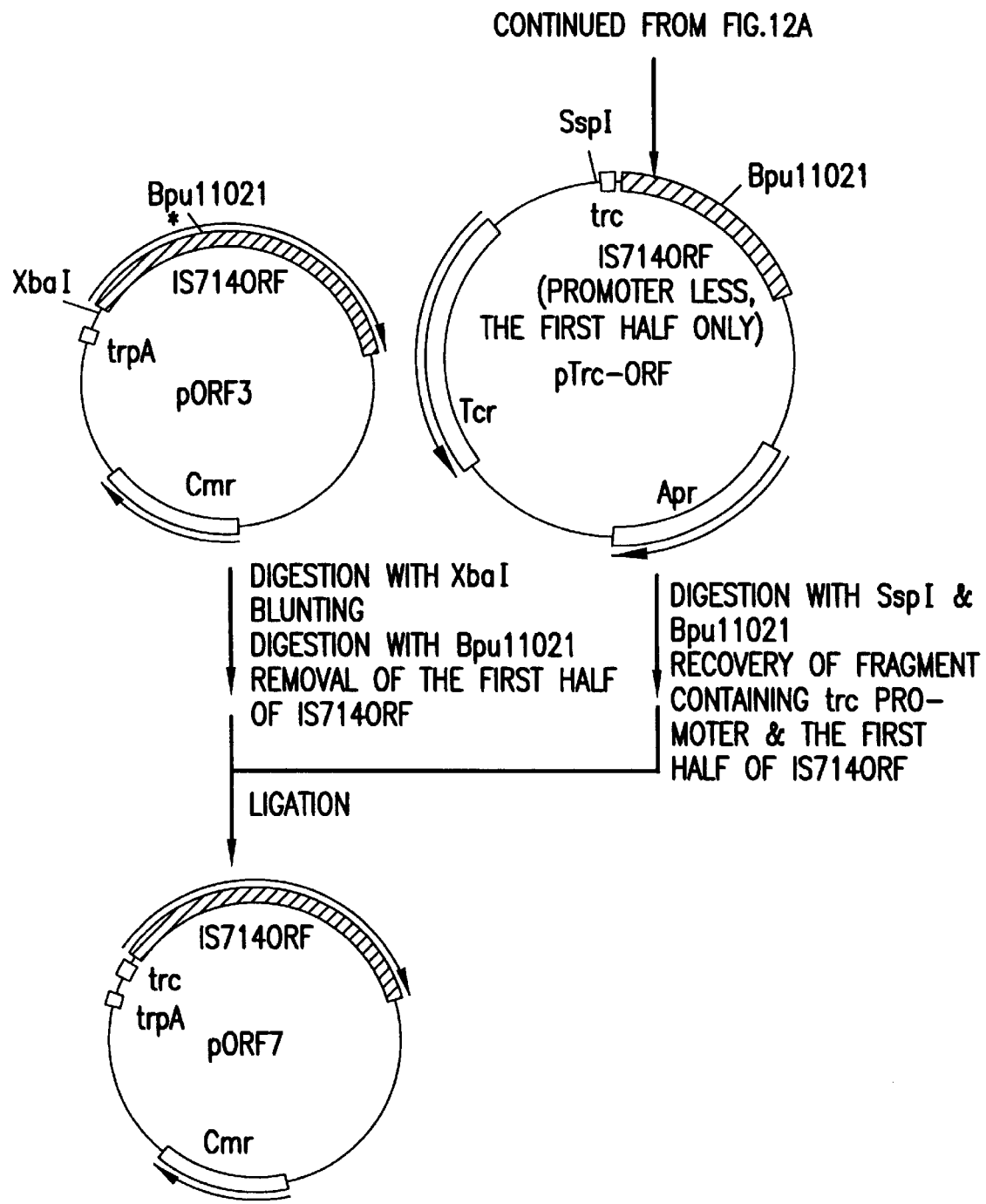
Figure 13B:
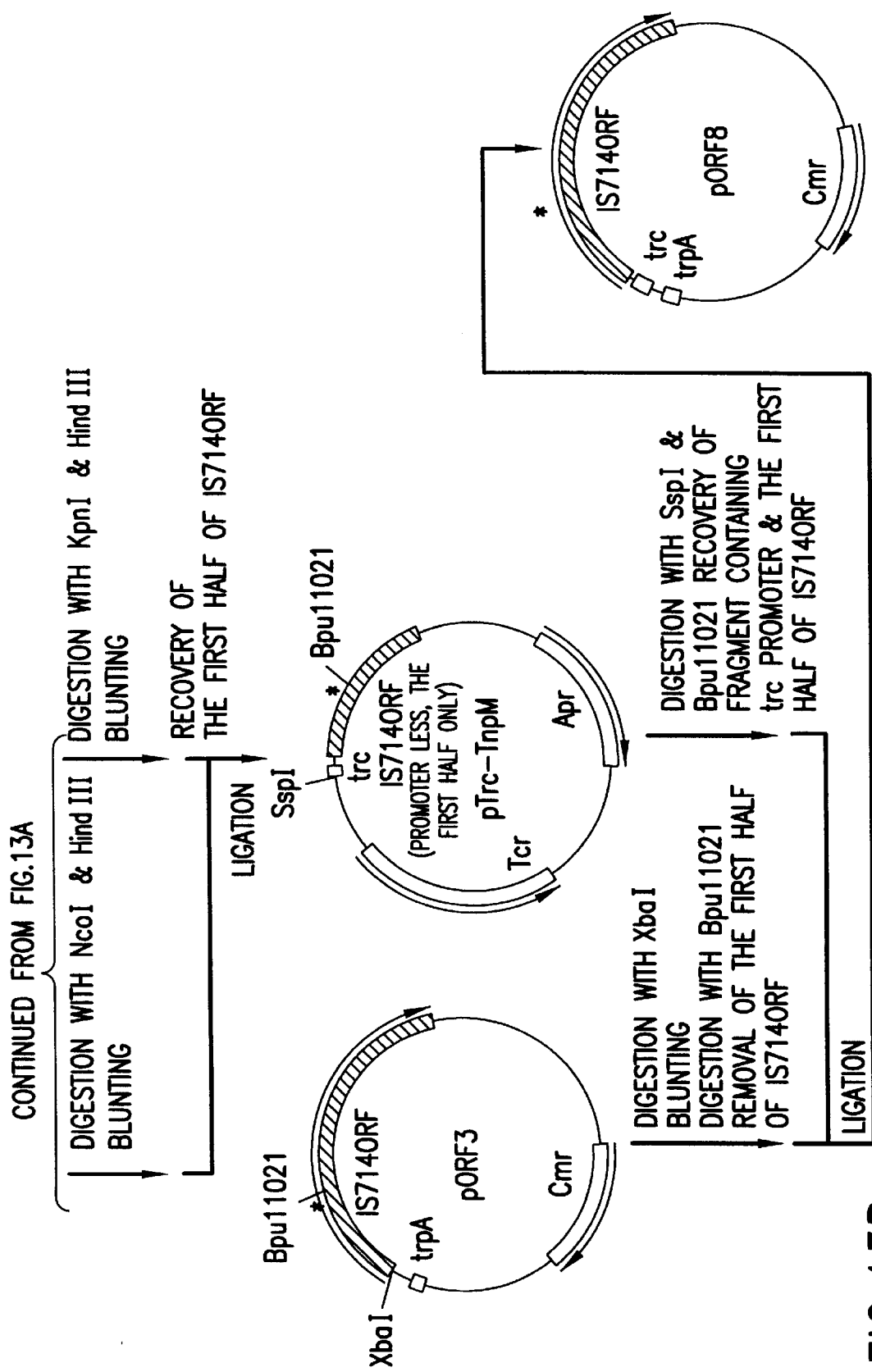
Figure 14B:
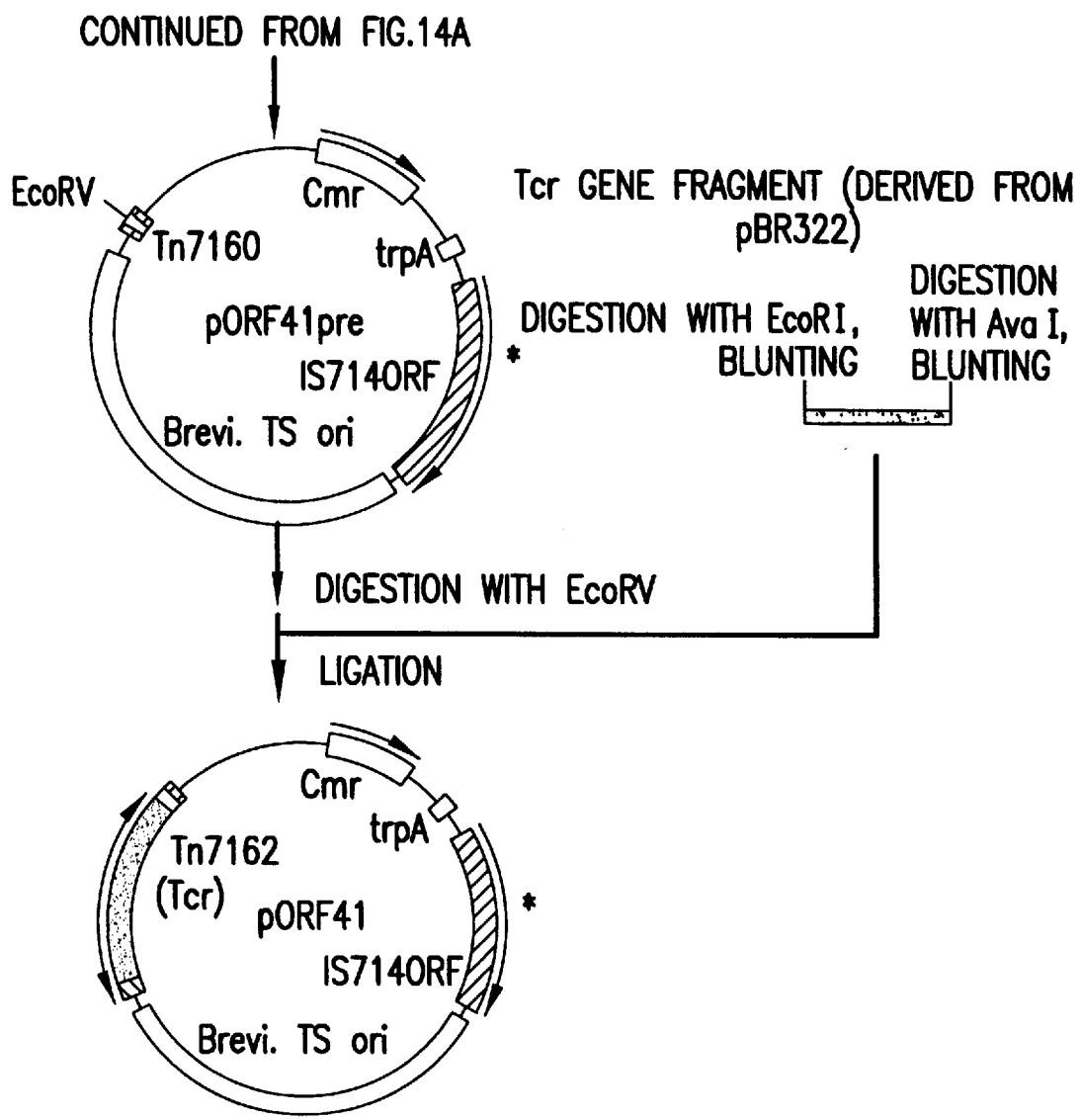

It is certified that an error appears in the above-identified patent and that said Letters Patent is hereby corrected as shown below:

Column 3, line 47, "9 is" should read --9A and FIG. 9B are--;
 line 49, "10 is" should read --10A and FIG. 10B are--;
 line 51, "11 is" should read --11A and FIG. 11B are--;
 line 53, "12 is" should read --12A and FIG. 12B are--;
 line 55, "13 is" should read --13A and FIG. 13B are--; and
 line 57, "14 is" should read --14A and FIG. 14B are--.

Figure 26B:
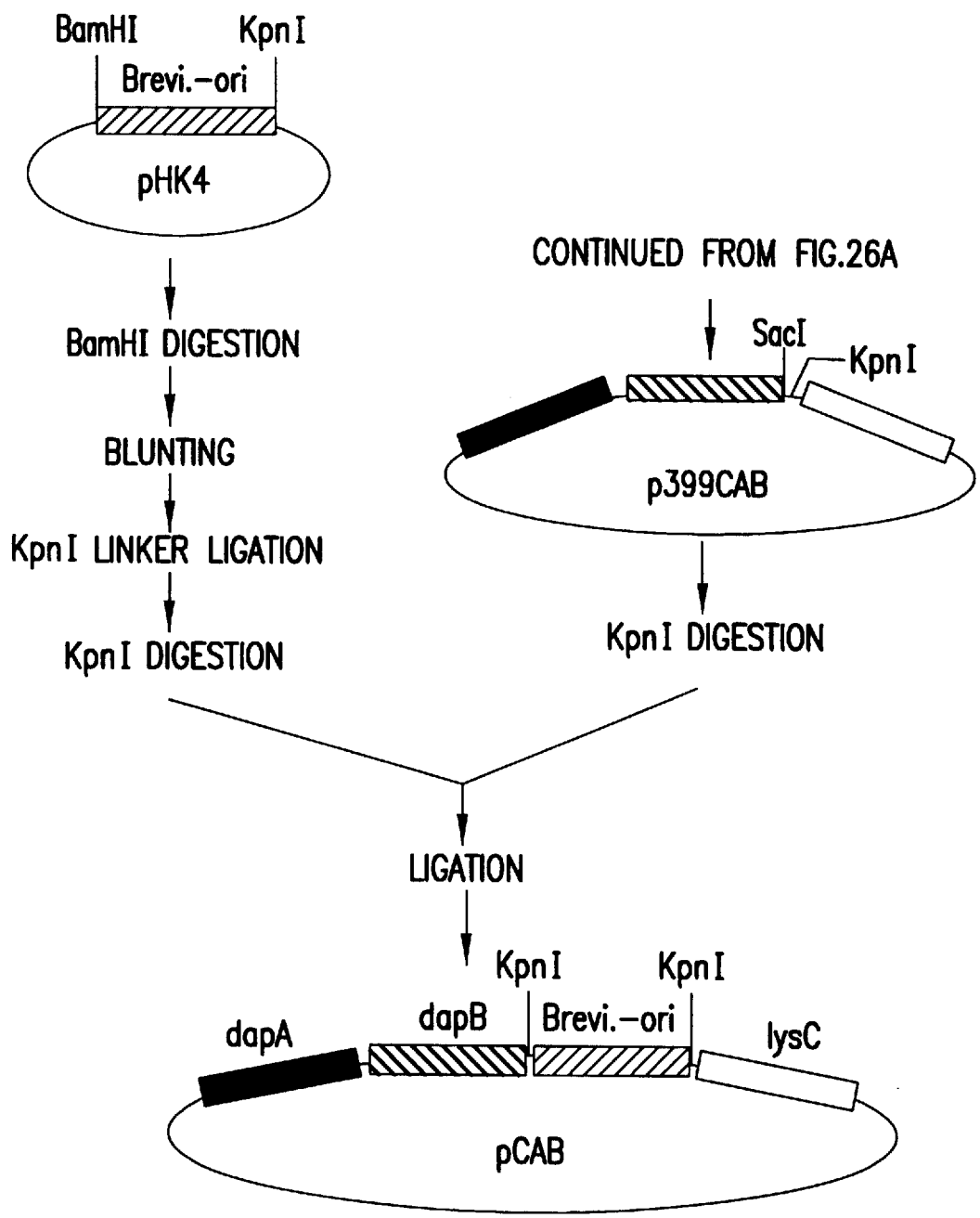
Figure 29B:
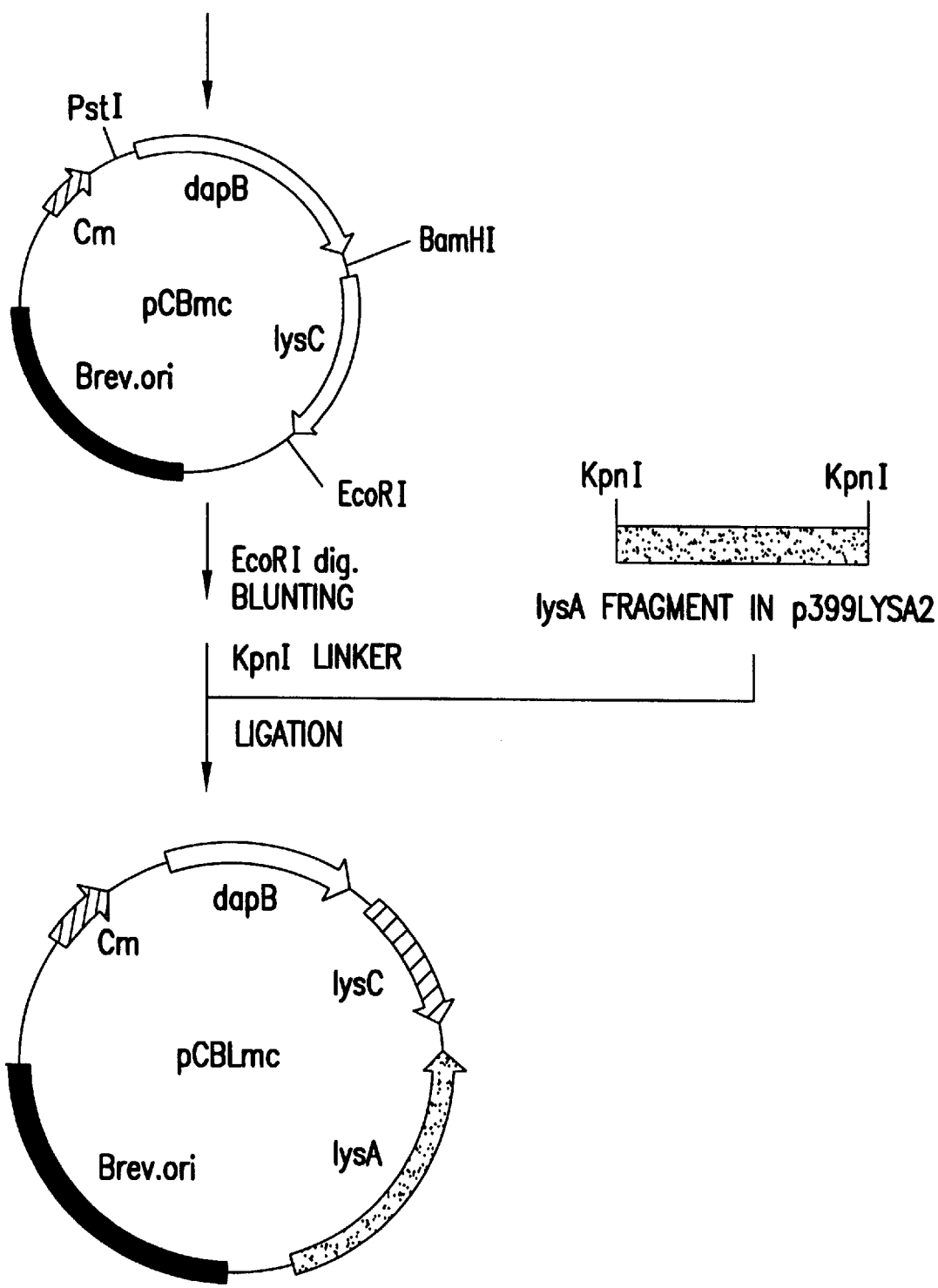
Figure 30:
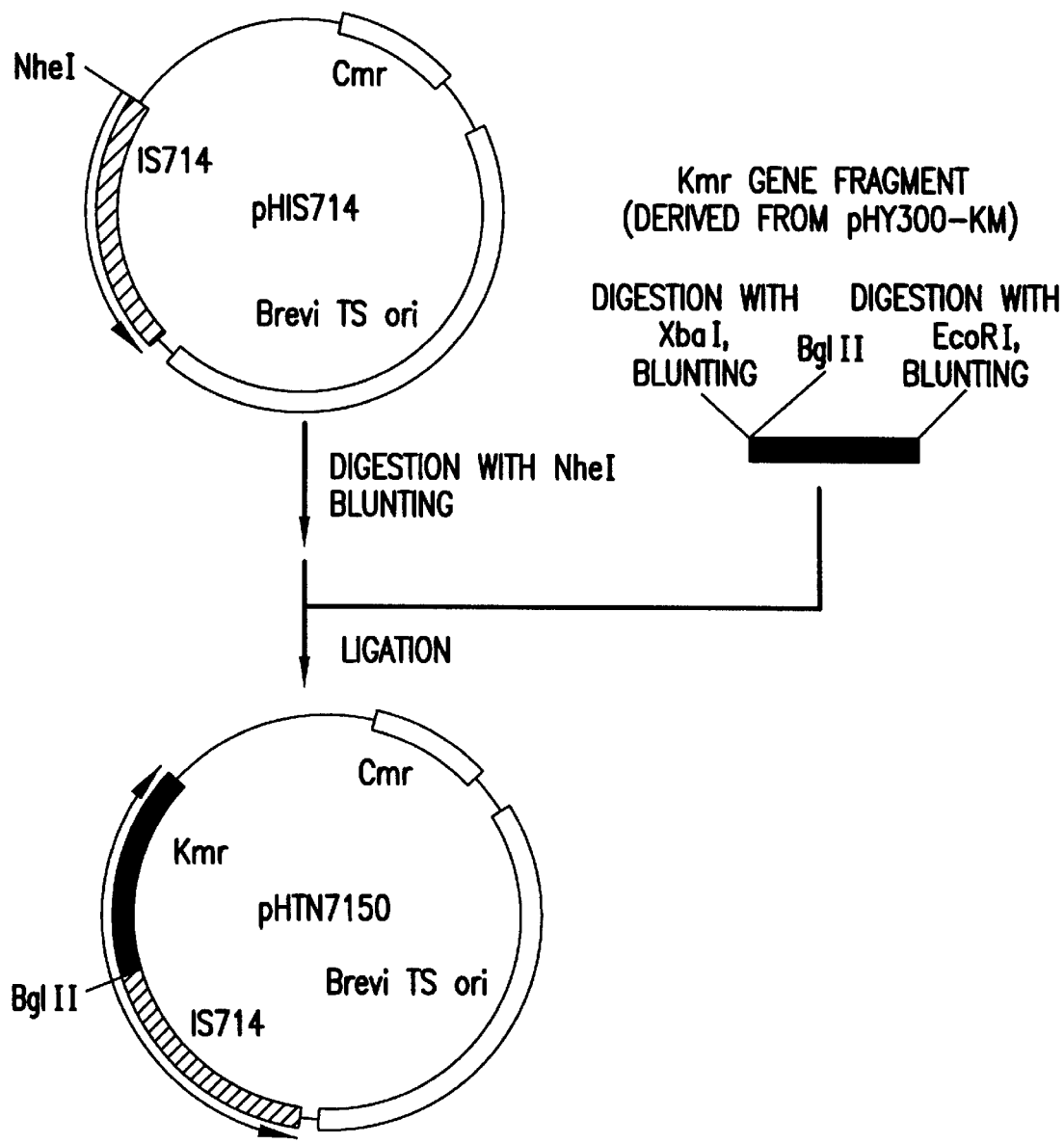
FIG. 30 is a view showing construction of the plasmid pHTN7150.

Column 4, line 19, "26 is" should read --26A and FIG. 26B are--; and
 line 25, "29 is" should read --29A and FIG. 29B are--.

Column 10, line 5, "9." should read --9A and FIG. 9B.--;
 line 21, "9." should read --9A and FIG. 9B.--;
 line 50, "10)." should read --10A and FIG. 10B).--; and
 lines 62 and 63, "M/pUC19 is shown in FIG. 11. indicates the introduced mutation." should read --M/pUC19 is shown in FIG. 11A and FIG. 11B. * indicates the introduced mutation.--

Column 11, line 41, "11." should read --11A and FIG. 11B.--; and
 line 61, "12." should read --12A and FIG. 12B.--.

Column 12, line 10, "13)." should read --13A and FIG. 13B).--; and
 line 33, "14." should read --14A and FIG. 14B.--.

UNITED STATES PATENT AND TRADEMARK OFFICE
CERTIFICATE OF CORRECTION

PATENT NO. : 5,804,414

DATED : September 8, 1998

INVENTOR(S): Mika MORIYA et al.

It is certified that an error appears in the above-identified patent and that said Letters Patent is hereby corrected as shown below:

Column 20, line 37, "9." should read --9A and FIG. 9B.--; and
line 64, "9." should read --9A and FIG. 9B.--.

Column 26, line 5, "26)." should read --26A and FIG. 26B).--.
line 53, "26." should read --26A and FIG. 26B.--.

Column 29, line 41, "29." should read --29A and FIG. 29B.--.

Column 30, line 44, "10." should read --10A and FIG. 10B.--.

Column 31, line 20, "11." should read --11A and FIG. 11B.--;
line 41, "12." should read --12A and FIG. 12B.--; and
line 57, "13)." should read --13A and FIG. 13B).--.

Column 32, line 17, "14." should read --14A and FIG. 14B.--.

Signed and Sealed this

Seventeenth Day of April, 2001

Attest:

NICHOLAS P. GODICI

Attesting Officer    Acting Director of the United States Patent and Trademark Office

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 1453 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Brevibacterium lactofermentum
    ( B ) STRAIN: AJ12036

( i x ) FEATURE:
    ( A ) NAME/KEY: repeat_region
    ( B ) LOCATION: 1..5

( i x ) FEATURE:
    ( A ) NAME/KEY: repeat_region
    ( B ) LOCATION: 1439..1453

( i x ) FEATURE:
    ( A ) NAME/KEY: -35_signal
    ( B ) LOCATION: 71..76

( i x ) FEATURE:
    ( A ) NAME/KEY: -10_signal
    ( B ) LOCATION: 92..97

( i x ) FEATURE:
    ( A ) NAME/KEY: CDS
    ( B ) LOCATION: 130..1440

( x i ) SEQUENCE DESCRIPTION: SEQ ID NO:1:

```
GGCCCTTCCG  GTTTTGGGGT  ACATCACAGA  ACCTGGGCTA  GCGGTGTAGA  CCCGAAAATA           60

AACGAGCCTT  TTGTCAGGGT  TAAGGTTTAG  GTATCTAAGC  TAACCAAACA  CCAACAAAAG          120

GCTCTACCC  ATG  AAG  TCT  ACC  GGC  AAC  ATC  ATC  GCT  GAC  ACC  ATC  TGC      168
           Met  Lys  Ser  Thr  Gly  Asn  Ile  Ile  Ala  Asp  Thr  Ile  Cys
             1              5                        10

CGC  ACT  GCG  GAA  CTA  GGA  CTC  ACC  ATC  ACC  GGC  GCT  TCC  GAT  GCA  GGT  216
Arg  Thr  Ala  Glu  Leu  Gly  Leu  Thr  Ile  Thr  Gly  Ala  Ser  Asp  Ala  Gly
     15                  20                       25

GAT  TAC  ACC  CTG  ATC  GAA  GCA  GAC  GCA  CTC  GAC  TAT  ACC  TCC  ACC  TGC  264
Asp  Tyr  Thr  Leu  Ile  Glu  Ala  Asp  Ala  Leu  Asp  Tyr  Thr  Ser  Thr  Cys
 30                  35                        40                        45

CCA  GAA  TGC  TTC  CAA  CCT  GGG  GTG  TTT  CGT  CAT  CAC  ACC  CAC  CGG  ATG  312
Pro  Glu  Cys  Phe  Gln  Pro  Gly  Val  Phe  Arg  His  His  Thr  His  Arg  Met
                50                       55                        60

CTC  ATT  GAT  TTA  CCC  ATC  GTC  GGG  TTT  CCC  ACC  AAA  CTG  TTT  ATC  CGT  360
Leu  Ile  Asp  Leu  Pro  Ile  Val  Gly  Phe  Pro  Thr  Lys  Leu  Phe  Ile  Arg
              65                       70                        75

CTA  CCT  CGC  TAC  CGC  TGC  ACC  AAC  CCG  ACA  TGT  AAG  CAA  AAG  TAT  TTC  408
Leu  Pro  Arg  Tyr  Arg  Cys  Thr  Asn  Pro  Thr  Cys  Lys  Gln  Lys  Tyr  Phe
          80                       85                        90

CAA  GCA  GAA  CTA  AGC  TGC  GCT  GAC  CAC  GGT  AAA  AAG  GTC  ACC  CAC  CGG  456
Gln  Ala  Glu  Leu  Ser  Cys  Ala  Asp  His  Gly  Lys  Lys  Val  Thr  His  Arg
      95                      100                       105

GTC  ACC  CGC  TGG  ATT  TTG  CAA  CGC  CTT  GCT  ATT  GAC  CGG  ATG  AGT  GTT  504
Val  Thr  Arg  Trp  Ile  Leu  Gln  Arg  Leu  Ala  Ile  Asp  Arg  Met  Ser  Val
110                      115                       120                      125

CAC  GCA  ACT  GCG  AAA  GCA  CTT  GGG  CTA  GGG  TGG  GAT  TTA  ACC  TGC  CAA  552
His  Ala  Thr  Ala  Lys  Ala  Leu  Gly  Leu  Gly  Trp  Asp  Leu  Thr  Cys  Gln
                     130                       135                      140

CTA  GCC  CTC  GAT  ATG  TGC  CGT  GAG  CTG  GTC  TAT  AAC  GAT  CCT  CAC  CAT  600
Leu  Ala  Leu  Asp  Met  Cys  Arg  Glu  Leu  Val  Tyr  Asn  Asp  Pro  His  His
                145                      150                       155

CTT  GAT  GGA  GTG  TAT  GTC  ATT  GGG  GTG  GAT  GAG  CAT  AAG  TGG  TCA  CAT  648
Leu  Asp  Gly  Val  Tyr  Val  Ile  Gly  Val  Asp  Glu  His  Lys  Trp  Ser  His
           160                       165                      170

AAT  AGG  GCT  AAG  CAT  GGT  GAT  GGG  TTT  GTC  ACC  GTG  ATT  GTC  GAT  ATG  696
Asn  Arg  Ala  Lys  His  Gly  Asp  Gly  Phe  Val  Thr  Val  Ile  Val  Asp  Met
```

```
                        175                             180                             185
ACC  GGG  CAT  CGG  TAT  GAC  TCA  CGG  TGT  CCT  GCC  CGG  TTA  TTA  GAT  GTC           744
Thr  Gly  His  Arg  Tyr  Asp  Ser  Arg  Cys  Pro  Ala  Arg  Leu  Leu  Asp  Val
190                 195                      200                           205

GTC  CCA  GGT  CGT  AGT  GCT  GAT  GCT  TTA  CGG  TCC  TGG  CTT  GGC  TCC  CGC           792
Val  Pro  Gly  Arg  Ser  Ala  Asp  Ala  Leu  Arg  Ser  Trp  Leu  Gly  Ser  Arg
                         210                      215                      220

GGT  GAA  CAG  TTC  CGC  AAT  CAG  ATA  CGG  ATC  GTG  TCC  ATG  GAT  GGA  TTC           840
Gly  Glu  Gln  Phe  Arg  Asn  Gln  Ile  Arg  Ile  Val  Ser  Met  Asp  Gly  Phe
               225                      230                      235

CAA  GGC  TAC  GCC  ACA  GCA  AGT  AAA  GAA  CTC  ATT  CCT  TCT  GCT  CGT  CGC           888
Gln  Gly  Tyr  Ala  Thr  Ala  Ser  Lys  Glu  Leu  Ile  Pro  Ser  Ala  Arg  Arg
          240                      245                      250

GTG  ATG  GAT  CCA  TTC  CAT  GTT  GTG  CGG  CTT  GCT  GGT  GAC  AAG  CTC  ACC           936
Val  Met  Asp  Pro  Phe  His  Val  Val  Arg  Leu  Ala  Gly  Asp  Lys  Leu  Thr
     255                      260                      265

GCC  TGC  CGG  CAA  CGC  CTC  CAG  CGG  GAG  AAA  TAC  CAG  CGT  CGT  GGT  TTA           984
Ala  Cys  Arg  Gln  Arg  Leu  Gln  Arg  Glu  Lys  Tyr  Gln  Arg  Arg  Gly  Leu
270                           275                      280                 285

AGC  CAG  GAT  CCG  TTG  TAT  AAA  AAC  CGG  AAG  ACC  TTG  TTG  ACC  ACG  CAC          1032
Ser  Gln  Asp  Pro  Leu  Tyr  Lys  Asn  Arg  Lys  Thr  Leu  Leu  Thr  Thr  His
                    290                      295                      300

AAG  TGG  TTG  AGT  CCT  CGT  CAG  CAA  GAA  AGC  TTG  GAG  CAG  TTG  TGG  GCG          1080
Lys  Trp  Leu  Ser  Pro  Arg  Gln  Gln  Glu  Ser  Leu  Glu  Gln  Leu  Trp  Ala
               305                      310                      315

TAT  GAC  AAA  GAC  TAC  GGG  GTG  TTA  AAG  CTT  GCG  TGG  CTT  GCG  TAT  CAG          1128
Tyr  Asp  Lys  Asp  Tyr  Gly  Val  Leu  Lys  Leu  Ala  Trp  Leu  Ala  Tyr  Gln
          320                      325                      330

GCG  ATT  ATT  GAT  TGT  TAT  CAG  ATG  GGT  AAT  AAG  CGT  GAA  GCG  AAG  AAG          1176
Ala  Ile  Ile  Asp  Cys  Tyr  Gln  Met  Gly  Asn  Lys  Arg  Glu  Ala  Lys  Lys
     335                      340                      345

AAA  ATG  CGG  ACC  ATT  ATT  GAT  CAG  CTT  CGG  GTG  TTG  AAG  GGG  CCG  AAT          1224
Lys  Met  Arg  Thr  Ile  Ile  Asp  Gln  Leu  Arg  Val  Leu  Lys  Gly  Pro  Asn
350                           355                      360                 365

AAG  GAA  CTC  GCG  CAG  TTG  GGT  CGT  AGT  TTG  TTT  AAA  CGA  CTT  GGT  GAT          1272
Lys  Glu  Leu  Ala  Gln  Leu  Gly  Arg  Ser  Leu  Phe  Lys  Arg  Leu  Gly  Asp
                    370                      375                      380

GTG  TTG  GCG  TAT  TTC  GAC  GTA  GGA  GTC  TCC  AAC  GGA  CCA  GTC  GAA  GCC          1320
Val  Leu  Ala  Tyr  Phe  Asp  Val  Gly  Val  Ser  Asn  Gly  Pro  Val  Glu  Ala
               385                      390                      395

ATC  AAT  GGA  CGC  CTA  GAA  CAC  CTC  CGC  GGA  ATC  GCG  CTT  GGA  TTC  CGC          1368
Ile  Asn  Gly  Arg  Leu  Glu  His  Leu  Arg  Gly  Ile  Ala  Leu  Gly  Phe  Arg
          400                      405                      410

AAC  CTC  ACC  CAC  TAC  ATC  CTT  CGA  TGC  CTC  ATC  CAC  TCC  GGA  CAG  CTC          1416
Asn  Leu  Thr  His  Tyr  Ile  Leu  Arg  Cys  Leu  Ile  His  Ser  Gly  Gln  Leu
     415                      420                      425

ACC  CAC  AAA  ATC  AAT  GCA  CTC  TAA  AAACGGAAGA  GCC                                  1453
Thr  His  Lys  Ile  Asn  Ala  Leu  *
430                      435
```

( 2 ) INFORMATION FOR SEQ ID NO:2:

( i ) SEQUENCE CHARACTERISTICS:
        ( A ) LENGTH: 436 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Ser  Thr  Gly  Asn  Ile  Ile  Ala  Asp  Thr  Ile  Cys  Arg  Thr  Ala
 1              5                        10                       15
```

```
Glu  Leu  Gly  Leu  Thr  Ile  Thr  Gly  Ala  Ser  Asp  Ala  Gly  Asp  Tyr  Thr
               20                  25                       30

Leu  Ile  Glu  Ala  Asp  Ala  Leu  Asp  Tyr  Thr  Ser  Thr  Cys  Pro  Glu  Cys
               35                  40                       45

Phe  Gln  Pro  Gly  Val  Phe  Arg  His  His  Thr  His  Arg  Met  Leu  Ile  Asp
          50                  55                  60

Leu  Pro  Ile  Val  Gly  Phe  Pro  Thr  Lys  Leu  Phe  Ile  Arg  Leu  Pro  Arg
 65                       70                  75                            80

Tyr  Arg  Cys  Thr  Asn  Pro  Thr  Cys  Lys  Gln  Lys  Tyr  Phe  Gln  Ala  Glu
                    85                  90                            95

Leu  Ser  Cys  Ala  Asp  His  Gly  Lys  Lys  Val  Thr  His  Arg  Val  Thr  Arg
               100                 105                      110

Trp  Ile  Leu  Gln  Arg  Leu  Ala  Ile  Asp  Arg  Met  Ser  Val  His  Ala  Thr
               115                 120                      125

Ala  Lys  Ala  Leu  Gly  Leu  Gly  Trp  Asp  Leu  Thr  Cys  Gln  Leu  Ala  Leu
          130                 135                      140

Asp  Met  Cys  Arg  Glu  Leu  Val  Tyr  Asn  Asp  Pro  His  His  Leu  Asp  Gly
145                      150                      155                      160

Val  Tyr  Val  Ile  Gly  Val  Asp  Glu  His  Lys  Trp  Ser  His  Asn  Arg  Ala
                    165                 170                           175

Lys  His  Gly  Asp  Gly  Phe  Val  Thr  Ile  Val  Asp  Met  Thr  Gly  His
               180                 185                      190

Arg  Tyr  Asp  Ser  Arg  Cys  Pro  Ala  Arg  Leu  Leu  Asp  Val  Val  Pro  Gly
               195                 200                      205

Arg  Ser  Ala  Asp  Ala  Leu  Arg  Ser  Trp  Leu  Gly  Ser  Arg  Gly  Glu  Gln
          210                 215                      220

Phe  Arg  Asn  Gln  Ile  Arg  Ile  Val  Ser  Met  Asp  Gly  Phe  Gln  Gly  Tyr
225                      230                      235                      240

Ala  Thr  Ala  Ser  Lys  Glu  Leu  Ile  Pro  Ser  Ala  Arg  Arg  Val  Met  Asp
                    245                 250                           255

Pro  Phe  His  Val  Val  Arg  Leu  Ala  Gly  Asp  Lys  Leu  Thr  Ala  Cys  Arg
               260                 265                      270

Gln  Arg  Leu  Gln  Arg  Glu  Lys  Tyr  Gln  Arg  Arg  Gly  Leu  Ser  Gln  Asp
          275                 280                      285

Pro  Leu  Tyr  Lys  Asn  Arg  Lys  Thr  Leu  Leu  Thr  Thr  His  Lys  Trp  Leu
290                      295                      300

Ser  Pro  Arg  Gln  Gln  Glu  Ser  Leu  Glu  Gln  Leu  Trp  Ala  Tyr  Asp  Lys
305                      310                      315                      320

Asp  Tyr  Gly  Val  Leu  Lys  Leu  Ala  Trp  Leu  Ala  Tyr  Gln  Ala  Ile  Ile
                    325                 330                           335

Asp  Cys  Tyr  Gln  Met  Gly  Asn  Lys  Arg  Glu  Ala  Lys  Lys  Lys  Met  Arg
               340                 345                      350

Thr  Ile  Ile  Asp  Gln  Leu  Arg  Val  Leu  Lys  Gly  Pro  Asn  Lys  Glu  Leu
               355                 360                      365

Ala  Gln  Leu  Gly  Arg  Ser  Leu  Phe  Lys  Arg  Leu  Gly  Asp  Val  Leu  Ala
          370                 375                      380

Tyr  Phe  Asp  Val  Gly  Val  Ser  Asn  Gly  Pro  Val  Glu  Ala  Ile  Asn  Gly
385                      390                      395                      400

Arg  Leu  Glu  His  Leu  Arg  Gly  Ile  Ala  Leu  Gly  Phe  Arg  Asn  Leu  Thr
                    405                 410                           415

His  Tyr  Ile  Leu  Arg  Cys  Leu  Ile  His  Ser  Gly  Gln  Leu  Thr  His  Lys
               420                 425                      430

Ile  Asn  Ala  Leu
```

4 3 5

( 2 ) INFORMATION FOR SEQ ID NO:3:

( i ) SEQUENCE CHARACTERISTICS:
    ( A ) LENGTH: 15 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Brevibacterium lactofermentum
    ( B ) STRAIN: AJ12036

( x i ) SEQUENCE DESCRIPTION: SEQ ID NO:3:

G G C C C T T C C G   G T T T T                              1 5

( 2 ) INFORMATION FOR SEQ ID NO:4:

( i ) SEQUENCE CHARACTERISTICS:
    ( A ) LENGTH: 15 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Brevibacterium lactofermentum
    ( B ) STRAIN: AJ12036

( x i ) SEQUENCE DESCRIPTION: SEQ ID NO:4:

G G C T C T T C C G   T T T T T                              1 5

( 2 ) INFORMATION FOR SEQ ID NO:5:

( i ) SEQUENCE CHARACTERISTICS:
    ( A ) LENGTH: 1453 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Brevibacterium lactofermentum
    ( B ) STRAIN: AJ12036

( i x ) FEATURE:
    ( A ) NAME/KEY: repeat_region
    ( B ) LOCATION: 1..15

( i x ) FEATURE:
    ( A ) NAME/KEY: repeat_region
    ( B ) LOCATION: 1439..1453

( i x ) FEATURE:
    ( A ) NAME/KEY: -35_signal
    ( B ) LOCATION: 71..76

( i x ) FEATURE:

(A) NAME/KEY: -10_signal
(B) LOCATION: 92..97

(ix) FEATURE:
(A) NAME/KEY: CDS
(B) LOCATION: 130..1440

(xi) SEQUENCE DESCRIPTION: SEQ ID NO:5:

```
GGCCCTTCCG GTTTTGGGGT ACATCACAGA ACCTGGGCTA GCGGTGTAGA CCCGAAAATA          60

AACGAGCCTT TTGTCAGGGT TAAGGTTTAG GTATCTAAGC TAACCAAACA CCAACAAAAG         120

GCTCTACCC ATG AAG TCT ACC GGC AAC ATC ATC GCT GAC ACC ATC TGC            168
          Met Lys Ser Thr Gly Asn Ile Ile Ala Asp Thr Ile Cys
          440                 445                 450

CGC ACT GCG GAA CTA GGA CTC ACC ATC ACC GGC GCT TCC GAT GCA GGT          216
Arg Thr Ala Glu Leu Gly Leu Thr Ile Thr Gly Ala Ser Asp Ala Gly
            455                 460                 465

GAT TAC ACC CTG ATC GAA GCA GAC GCA CTC GAC TAT ACC TCC ACC TGC          264
Asp Tyr Thr Leu Ile Glu Ala Asp Ala Leu Asp Tyr Thr Ser Thr Cys
            470                 475                 480

CCA GAA TGC TTC CAA CCT GGG GTG TTT CGT CAT CAC ACC CAC CGG ATG          312
Pro Glu Cys Phe Gln Pro Gly Val Phe Arg His His Thr His Arg Met
        485                 490                 495

CTC ATT GAT TTA CCC ATC GTC GGG TTT CCC ACC AAA CTG TTT ATC CGT          360
Leu Ile Asp Leu Pro Ile Val Gly Phe Pro Thr Lys Leu Phe Ile Arg
        500                 505                 510

CTA CCT CGC TAC CGC TGC ACC AAC CCG ACA TGT AAG CAA AAG TAT TTC          408
Leu Pro Arg Tyr Arg Cys Thr Asn Pro Thr Cys Lys Gln Lys Tyr Phe
515                 520                 525                 530

CAA GCA GAA CTA AGC TGC GCT GAC CAC GGT AAA AAG GTC ACC CAC CGG          456
Gln Ala Glu Leu Ser Cys Ala Asp His Gly Lys Lys Val Thr His Arg
            535                 540                 545

GTC ACC CGC TGG ATT TTG CAA CGC CTT GCT ATT GAC CGG ATG AGT GTT          504
Val Thr Arg Trp Ile Leu Gln Arg Leu Ala Ile Asp Arg Met Ser Val
            550                 555                 560

CAC GCA ACT GCG AAA GCA CTT GGG CTA GGG TGG GAT TTA ACC TGC CAA          552
His Ala Thr Ala Lys Ala Leu Gly Leu Gly Trp Asp Leu Thr Cys Gln
            565                 570                 575

CTA GCC CTC GAT ATG TGC CGT GAG CTG GTC TAT AAC GAT CCT CAC CAT          600
Leu Ala Leu Asp Met Cys Arg Glu Leu Val Tyr Asn Asp Pro His His
        580                 585                 590

CTT GAT GGA GTG TAT GTC ATT GGG GTG GAT GAG CAT AAG TGG TCA CAT          648
Leu Asp Gly Val Tyr Val Ile Gly Val Asp Glu His Lys Trp Ser His
595                 600                 605                 610

AAT AGG GCT AAG CAT GGT GAT GGG TTT GTC ACC GTG ATT GTC GAT ATG          696
Asn Arg Ala Lys His Gly Asp Gly Phe Val Thr Val Ile Val Asp Met
            615                 620                 625

ACC GGG CAT CGG TAT GAC TCA CGG TGT CCT GCC CGG TTA TTA GAT GTC          744
Thr Gly His Arg Tyr Asp Ser Arg Cys Pro Ala Arg Leu Leu Asp Val
            630                 635                 640

GTC CCA GGT CGT AGT GCT GAT GCT TTA CGG TCC TGG CTT GGC TCC CGC          792
Val Pro Gly Arg Ser Ala Asp Ala Leu Arg Ser Trp Leu Gly Ser Arg
            645                 650                 655

GGT GAA CAG TTC CGC AAT CAG ATA CGG ATC GTG TCC ATG GAT GGA TTC          840
Gly Glu Gln Phe Arg Asn Gln Ile Arg Ile Val Ser Met Asp Gly Phe
        660                 665                 670

CAA GGC TAC GCC ACA GCA AGT AAA GAA CTC ATT CCT TCT GCT CGT CGC          888
Gln Gly Tyr Ala Thr Ala Ser Lys Glu Leu Ile Pro Ser Ala Arg Arg
675                 680                 685                 690

GTG ATG GAT CCA TTC CAT GTT GTG CGG CTT GCT GGT GAC AAG CTC ACC          936
Val Met Asp Pro Phe His Val Val Arg Leu Ala Gly Asp Lys Leu Thr
            695                 700                 705
```

```
GCC  TGC  CGG  CAA  CGC  CTC  CAG  CGG  GAG  AAA  TAC  CAG  CGT  CGT  GGT  TTA      984
Ala  Cys  Arg  Gln  Arg  Leu  Gln  Arg  Glu  Lys  Tyr  Gln  Arg  Arg  Gly  Leu
          710                      715                      720

AGC  CAG  GAT  CCG  TTG  TAT  AAA  AAC  CGG  AAG  ACC  TTG  TTG  ACC  ACG  CAC     1032
Ser  Gln  Asp  Pro  Leu  Tyr  Lys  Asn  Arg  Lys  Thr  Leu  Leu  Thr  Thr  His
          725                      730                      735

AAG  TGG  TTG  AGT  CCT  CGT  CAG  CAA  GAA  AGC  TTG  GAG  CAG  TTG  TGG  GCG     1080
Lys  Trp  Leu  Ser  Pro  Arg  Gln  Gln  Glu  Ser  Leu  Glu  Gln  Leu  Trp  Ala
          740                      745                      750

TAT  GAC  AAA  GAC  TAC  GGG  GTG  TTA  AAG  CTT  GCG  TGG  CTT  GCG  TAT  CAG     1128
Tyr  Asp  Lys  Asp  Tyr  Gly  Val  Leu  Lys  Leu  Ala  Trp  Leu  Ala  Tyr  Gln
755                      760                      765                      770

GCG  ATT  ATT  GAT  TGT  TAT  CAG  ATG  GGT  AAT  AAG  CGT  GAA  GCG  AAG  AAG     1176
Ala  Ile  Ile  Asp  Cys  Tyr  Gln  Met  Gly  Asn  Lys  Arg  Glu  Ala  Lys  Lys
                    775                      780                      785

AAA  ATG  CGG  ACC  ATT  ATT  GAT  CAG  CTT  CGG  GTG  TTG  AAG  GGG  CCG  AAT     1224
Lys  Met  Arg  Thr  Ile  Ile  Asp  Gln  Leu  Arg  Val  Leu  Lys  Gly  Pro  Asn
          790                      795                      800

AAG  GAA  CTC  GCG  CAG  TTG  GGT  CGT  AGT  TTG  TTT  AAA  CGA  CTT  GGT  GAT     1272
Lys  Glu  Leu  Ala  Gln  Leu  Gly  Arg  Ser  Leu  Phe  Lys  Arg  Leu  Gly  Asp
          805                      810                      815

GTG  TTG  GCG  TAT  TTC  GAT  GTT  GGT  GTC  TCC  AAC  GGT  CCG  GTC  GAA  GCG     1320
Val  Leu  Ala  Tyr  Phe  Asp  Val  Gly  Val  Ser  Asn  Gly  Pro  Val  Glu  Ala
820                      825                      830

ATC  AAC  GGA  CGG  TTG  GAG  CAT  TTG  CGT  GGG  ATT  GCT  CTA  GGT  TTC  CGT     1368
Ile  Asn  Gly  Arg  Leu  Glu  His  Leu  Arg  Gly  Ile  Ala  Leu  Gly  Phe  Arg
835                      840                      845                      850

AAT  TTG  AAC  CAC  TAC  ATT  CTG  CGG  TGC  CTT  ATC  CAT  TCA  GGG  CAG  TTG     1416
Asn  Leu  Asn  His  Tyr  Ile  Leu  Arg  Cys  Leu  Ile  His  Ser  Gly  Gln  Leu
                    855                      860                      865

GTC  CAT  AAG  ATC  AAT  GCA  CTC  TAA  AACAGGAAGA  GCC                              1453
Val  His  Lys  Ile  Asn  Ala  Leu   *
870
```

( 2 ) INFORMATION FOR SEQ ID NO:6:

( i ) SEQUENCE CHARACTERISTICS:
( A ) LENGTH: 436 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met  Lys  Ser  Thr  Gly  Asn  Ile  Ile  Ala  Asp  Thr  Ile  Cys  Arg  Thr  Ala
 1                   5                   10                  15

Glu  Leu  Gly  Leu  Thr  Ile  Thr  Gly  Ala  Ser  Asp  Ala  Gly  Asp  Tyr  Thr
               20                  25                  30

Leu  Ile  Glu  Ala  Asp  Ala  Leu  Asp  Tyr  Thr  Ser  Thr  Cys  Pro  Glu  Cys
          35                  40                  45

Phe  Gln  Pro  Gly  Val  Phe  Arg  His  His  Thr  His  Arg  Met  Leu  Ile  Asp
     50                  55                  60

Leu  Pro  Ile  Val  Gly  Phe  Pro  Thr  Lys  Leu  Phe  Ile  Arg  Leu  Pro  Arg
65                   70                  75                       80

Tyr  Arg  Cys  Thr  Asn  Pro  Thr  Cys  Lys  Gln  Lys  Tyr  Phe  Gln  Ala  Glu
                    85                  90                       95

Leu  Ser  Cys  Ala  Asp  His  Gly  Lys  Lys  Val  Thr  His  Arg  Val  Thr  Arg
               100                 105                 110

Trp  Ile  Leu  Gln  Arg  Leu  Ala  Ile  Asp  Arg  Met  Ser  Val  His  Ala  Thr
          115                 120                 125
```

```
Ala  Lys  Ala  Leu  Gly  Leu  Gly  Trp  Asp  Leu  Thr  Cys  Gln  Leu  Ala  Leu
     130                 135                      140

Asp  Met  Cys  Arg  Glu  Leu  Val  Tyr  Asn  Asp  Pro  His  His  Leu  Asp  Gly
145                      150                      155                          160

Val  Tyr  Val  Ile  Gly  Val  Asp  Glu  His  Lys  Trp  Ser  His  Asn  Arg  Ala
               165                       170                          175

Lys  His  Gly  Asp  Gly  Phe  Val  Thr  Val  Ile  Val  Asp  Met  Thr  Gly  His
               180                 185                           190

Arg  Tyr  Asp  Ser  Arg  Cys  Pro  Ala  Arg  Leu  Leu  Asp  Val  Val  Pro  Gly
          195                      200                      205

Arg  Ser  Ala  Asp  Ala  Leu  Arg  Ser  Trp  Leu  Gly  Ser  Arg  Gly  Glu  Gln
     210                      215                      220

Phe  Arg  Asn  Gln  Ile  Arg  Ile  Val  Ser  Met  Asp  Gly  Phe  Gln  Gly  Tyr
225                      230                      235                          240

Ala  Thr  Ala  Ser  Lys  Glu  Leu  Ile  Pro  Ser  Ala  Arg  Arg  Val  Met  Asp
               245                      250                           255

Pro  Phe  His  Val  Val  Arg  Leu  Ala  Gly  Asp  Lys  Leu  Thr  Ala  Cys  Arg
               260                      265                      270

Gln  Arg  Leu  Gln  Arg  Glu  Lys  Tyr  Gln  Arg  Arg  Gly  Leu  Ser  Gln  Asp
          275                      280                      285

Pro  Leu  Tyr  Lys  Asn  Arg  Lys  Thr  Leu  Leu  Thr  Thr  His  Lys  Trp  Leu
     290                      295                      300

Ser  Pro  Arg  Gln  Gln  Glu  Ser  Leu  Glu  Gln  Leu  Trp  Ala  Tyr  Asp  Lys
305                      310                      315                          320

Asp  Tyr  Gly  Val  Leu  Lys  Leu  Ala  Trp  Leu  Ala  Tyr  Gln  Ala  Ile  Ile
               325                      330                           335

Asp  Cys  Tyr  Gln  Met  Gly  Asn  Lys  Arg  Glu  Ala  Lys  Lys  Lys  Met  Arg
               340                      345                           350

Thr  Ile  Ile  Asp  Gln  Leu  Arg  Val  Leu  Lys  Gly  Pro  Asn  Lys  Glu  Leu
          355                      360                      365

Ala  Gln  Leu  Gly  Arg  Ser  Leu  Phe  Lys  Arg  Leu  Gly  Asp  Val  Leu  Ala
     370                      375                      380

Tyr  Phe  Asp  Val  Gly  Val  Ser  Asn  Gly  Pro  Val  Glu  Ala  Ile  Asn  Gly
385                      390                      395                          400

Arg  Leu  Glu  His  Leu  Arg  Gly  Ile  Ala  Leu  Gly  Phe  Arg  Asn  Leu  Asn
               405                      410                           415

His  Tyr  Ile  Leu  Arg  Cys  Leu  Ile  His  Ser  Gly  Gln  Leu  Val  His  Lys
               420                      425                      430

Ile  Asn  Ala  Leu
               435
```

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Brevibacterium lactofermentum
        ( B ) STRAIN: AJ12036

(x i) SEQUENCE DESCRIPTION: SEQ ID NO:7:

GGCCCTTCCG GTTTT 15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: YES (v i) ORIGINAL SOURCE:
        (A) ORGANISM: Brevibacterium lactofermentum
        (B) STRAIN: AJ12036

(x i) SEQUENCE DESCRIPTION: SEQ ID NO:8:

GGCTCTTCCG GTTTT 15

(2) INFORMATION FOR SEQ ID NO:9:

(i) SEQUENCE CHARACTERISTICS:
        (A) LENGTH: 1279 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Brevibacterium lactofermentum
        (B) STRAIN: AJ12036

(i x) FEATURE:
        (A) NAME/KEY: repeat_region
        (B) LOCATION: 1..14

(i x) FEATURE:
        (A) NAME/KEY: repeat_region
        (B) LOCATION: 1266..1279

(x i) SEQUENCE DESCRIPTION: SEQ ID NO:9:

| | | | | | |
|---|---|---|---|---|---|
| GGGACTGACC | CCTGTTTGGT | GGACACCTTG | AAACCAGCAT | GATGCTGGAA | AGGTAATCTG | 60 |
| CCACCATGCC | ACGCAAGACC | TATACAGAGG | AGTTCAAGCG | CGATGCCGTC | GCCTTGTACG | 120 |
| AGAACTCCCC | AGAGGCTTCG | ATCCAGACCA | TCGCCACCGA | TCTCGGGGTC | AACCGCGCCA | 180 |
| CGTTGGCGAA | CTGGGTGAAA | AAATACGGCA | CCGCAGGCTC | CCAACGAAAC | ACCCTCGCCA | 240 |
| GCCTCTGTGA | ACGAGGCTGA | GCAGATCCGG | AAACTGGAAC | GGGAAAACGC | TCGCTTGAGA | 300 |
| GAAGAGCGCG | ATATCCTGCG | GAAAGCTGCA | AAATATTTCG | CGGAAGAGAC | GAATTGGTGA | 360 |
| TCCGCTTCCG | GTTCGTTGAT | GACGCCTCCA | AGACCTACTC | GGTCAAGCGG | ATATGTGACG | 420 |
| TCCTCAAACT | CAACAGGTCT | TCCTACTATA | AATGGAAAAG | TACCTGCTCA | GCACGCAGGA | 480 |
| AACGCCTCAT | GTCGACGCGA | TCCTCGGGGC | TCGAGTCAAG | GCTGTCTTCA | CCACCGAAAA | 540 |
| TGGTTGTTAT | GGGGCCAAGC | GGATCACCGC | TGAACTCAAA | GACCAGGTGG | ATCATGACCC | 600 |
| CGTAAATCAC | AAGCGGGTCG | CTCGGGTGAT | GCGCTCGTTG | AAGCTGTTTG | GCTACACAAA | 660 |
| TAAACGCAAG | GTCACCACCA | CTGTGTCGGA | TAAAACCAAG | ACAGTGTTTC | CTGACCTTGT | 720 |

| | | | | | | |
|---|---|---|---|---|---|---|
| CGGCCGGAAG | TTCACCGCTA | ATAAGCCAAA | TCAGGTGTAC | GTCGGGACAT | CACGTACCTG | 780 |
| CCGATTGCTG | ATGGGTCGAA | TATGTACCTG | GCTACGGTCA | TTGACTGCTA | TTCCCGCAGG | 840 |
| TTGGTGGGCT | TTTCTATCGC | ACATCACATG | CGTACCTCCC | TGGTGCAGAC | GCGCTGCTGA | 900 |
| TGGCTAAGGG | CCAGCGCGAA | GCTGACGGGG | GCGATCTTTC | ACTCGGATCA | CGGAAGTGTT | 960 |
| TACACTTCTC | ACGCATTCCA | GACACCTGTA | AAGACCTGGG | ATAAGGCAGT | CGATGGGATC | 1020 |
| AATCGGCACC | AGTGCGACAA | TGCCTCGCGG | AGTCCTTCAA | CGCAGCACTG | AAGCGGAAGT | 1080 |
| CCTCCAGGAT | TCCAAGACAT | TCATGAACCA | GTTGCGCTGT | CGCCGGACG | TCTTCCGCTG | 1140 |
| GTGTACCCGC | TACAACATGG | TGCGCCGGCA | TTCCTGGTGT | AAATATCTCG | CCCTGCGGTG | 1200 |
| TTTGAGAAGC | GCTGTCCTGC | TATCCTGAAA | TCTGCTTCCT | GATCAAATCC | TCCGTGTCTA | 1260 |
| CTATCCGGGG | GTCGGGCCC | | | | | 1279 |

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Brevibacterium lactofermentum
        (B) STRAIN: AJ12036

(xi) SEQUENCE DESCRIPTION: SEQ ID NO:10:

GGGACTGACC CCTG        14

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Brevibacterium lactofermentum
        (B) STRAIN: AJ12036

(xi) SEQUENCE DESCRIPTION: SEQ ID NO:11:

GGGCCCGACC CCCG        14

(2) INFORMATION FOR SEQ ID NO:12:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO ( x i ) SEQUENCE DESCRIPTION: SEQ ID NO:12:

GGTTTATT                                                                                                                                8

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: NO ( x i ) SEQUENCE DESCRIPTION: SEQ ID NO:13:

GTGGAGCCGA  CCATTCCGCG  AGG                                                                                                           23

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: YES ( x i ) SEQUENCE DESCRIPTION: SEQ ID NO:14:

CCAAAACCGC  CCTCCACGGC  GAA                                                                                                           23

( 2 ) INFORMATION FOR SEQ ID NO:15:

( i ) SEQUENCE CHARACTERISTICS:
        ( A ) LENGTH: 3579 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Brevibacterium lactofermentum
        ( B ) STRAIN: ATCC 13869

( i x ) FEATURE:
        ( A ) NAME/KEY: CDS
        ( B ) LOCATION: 533..2182

( i x ) FEATURE:
        ( A ) NAME/KEY: CDS
        ( B ) LOCATION: 2188..3522

( x i ) SEQUENCE DESCRIPTION: SEQ ID NO:15:

GTGGAGCCGA  CCATTCCGCG  AGGCTGCACT  GCAACGAGGT  CGTAGTTTTG  GTACATGGCT      60

TCTGGCCAGT  TCATGGATTG  GCTGCCGAAG  AAGCTATAGG  CATCGCACCA  GGGCCACCGA     120

GTTACCGAAG  ATGGTGCCGT  GCTTTTCGCC  TTGGGCAGGG  ACCTTGACAA  AGCCCACGCT     180

GATATCGCCA  AGTGAGGGAT  CAGAATAGTG  CATGGGCACG  TCGATGCTGC  CACATTGAGC     240

GGAGGCAATA  TCTACCTGAG  GTGGGCATTC  TTCCCAGCGG  ATGTTTCTT  GCGCTGCTGC      300

AGTGGGCATT  GATACCAAAA  AGGGGCTAAG  CGCAGTCGAG  GCGGCAAGAA  CTGCTACTAC     360

-continued

| | | | | |
|---|---|---|---|---|
| CCTTTTTATT | GTCGAACGGG | GCATTACGGC | TCCAAGGACG | TTTGTTTTCT GGGTCAGTTA | 420 |
| CCCCAAAAAG | CATATACAGA | GACCAATGAT | TTTTCATTAA | AAAGGCAGGG ATTTGTTATA | 480 |
| AGTATGGGTC | GTATTCTGTG | CGACGGGTGT | ACCTCGGCTA | GAATTCTCC CC ATG | 535 |
| | | | | Met | |

```
ACA CCA GCT GAT CTC GCA ACA TTG ATT AAA GAG ACC GCG GTA GAG GTT    583
Thr Pro Ala Asp Leu Ala Thr Leu Ile Lys Glu Thr Ala Val Glu Val
440             445                 450

TTG ACC TCC CGC GAG CTC GAT ACT TCT GTT CTT CCG GAG CAG GTA GTT    631
Leu Thr Ser Arg Glu Leu Asp Thr Ser Val Leu Pro Glu Gln Val Val
455             460                 465                 470

GTG GAG CGT CCG CGT AAC CCA GAG CAC GGC GAT TAC GCC ACC AAC ATT    679
Val Glu Arg Pro Arg Asn Pro Glu His Gly Asp Tyr Ala Thr Asn Ile
                475             480                 485

GCA TTG CAG GTG GCT AAA AAG GTC GGT CAG AAC CCT CGG GAT TTG GCT    727
Ala Leu Gln Val Ala Lys Lys Val Gly Gln Asn Pro Arg Asp Leu Ala
            490             495                 500

ACC TGG CTG GCA GAG GCA TTG GCT GCA GAT GAC GCC ATT GAT TCT GCT    775
Thr Trp Leu Ala Glu Ala Leu Ala Ala Asp Asp Ala Ile Asp Ser Ala
                505             510                 515

GAA ATT GCT GGC CCA GGC TTT TTG AAC ATT CGC CTT GCT GCA GCA GCA    823
Glu Ile Ala Gly Pro Gly Phe Leu Asn Ile Arg Leu Ala Ala Ala Ala
520             525                 530

CAG GGT GAA ATT GTG GCC AAG ATT CTG GCA CAG GGC GAG ACT TTC GGA    871
Gln Gly Glu Ile Val Ala Lys Ile Leu Ala Gln Gly Glu Thr Phe Gly
535             540                 545                 550

AAC TCC GAT CAC CTT TCC CAC TTG GAC GTG AAC CTC GAG TTC GTT TCT    919
Asn Ser Asp His Leu Ser His Leu Asp Val Asn Leu Glu Phe Val Ser
                555             560                 565

GCA AAC CCA ACC GGA CCT ATT CAC CTT GGC GGA ACC CGC TGG GCT GCC    967
Ala Asn Pro Thr Gly Pro Ile His Leu Gly Gly Thr Arg Trp Ala Ala
            570             575                 580

GTG GGT GAC TCT TTG GGT CGT GTG CTG GAG GCT TCC GGC GCG AAA GTG    1015
Val Gly Asp Ser Leu Gly Arg Val Leu Glu Ala Ser Gly Ala Lys Val
                585             590                 595

ACC CGC GAA TAC TAC TTC AAC GAT CAC GGT CGC CAG ATC GAT CGT TTC    1063
Thr Arg Glu Tyr Tyr Phe Asn Asp His Gly Arg Gln Ile Asp Arg Phe
600             605                 610

GCT TTG TCC CTT CTT GCA GCG GCG AAG GGC GAG CCA ACG CCA GAA GAC    1111
Ala Leu Ser Leu Leu Ala Ala Ala Lys Gly Glu Pro Thr Pro Glu Asp
615             620                 625                 630

GGT TAT GGC GGC GAA TAC ATT AAG GAA ATT GCG GAG GCA ATC GTC GAA    1159
Gly Tyr Gly Gly Glu Tyr Ile Lys Glu Ile Ala Glu Ala Ile Val Glu
                635             640                 645

AAG CAT CCT GAA GCG TTG GCT TTG GAG CCT GCC GCA ACC CAG GAG CTT    1207
Lys His Pro Glu Ala Leu Ala Leu Glu Pro Ala Ala Thr Gln Glu Leu
            650             655                 660

TTC CGC GCT GAA GGC GTG GAG ATG ATG TTC GAG CAC ATC AAA TCT TCC    1255
Phe Arg Ala Glu Gly Val Glu Met Met Phe Glu His Ile Lys Ser Ser
                665             670                 675

CTG CAT GAG TTC GGC ACC GAT TTC GAT GTC TAC TAC CAC GAG AAC TCC    1303
Leu His Glu Phe Gly Thr Asp Phe Asp Val Tyr Tyr His Glu Asn Ser
680             685                 690

CTG TTC GAG TCC GGT GCG GTG GAC AAG GCC GTG CAG GTG CTG AAG GAC    1351
Leu Phe Glu Ser Gly Ala Val Asp Lys Ala Val Gln Val Leu Lys Asp
695             700                 705                 710

AAC GGC AAC CTG TAC GAA AAC GAG GGC GCT TGG TGG CTG CGT TCC ACC    1399
Asn Gly Asn Leu Tyr Glu Asn Glu Gly Ala Trp Trp Leu Arg Ser Thr
                715             720                 725

GAA TTC GGC GAT GAC AAA GAC CGC GTG GTG ATC AAG TCT GAC GGC GAC    1447
```

|     |     |     |     |     |     |     |     |     |     |     |     |     |     |     |
| --- | --- | --- | --- | --- | --- | --- | --- | --- | --- | --- | --- | --- | --- | --- |
| Glu | Phe | Gly | Asp | Asp | Lys | Asp | Arg | Val | Val | Ile | Lys | Ser | Asp | Gly | Asp |
|     |     |     | 730 |     |     |     | 735 |     |     |     |     |     | 740 |     |     |

```
GCA GCC TAC ATC GCT GGC GAT ATC GCG TAC GTG GCT GAT AAG TTC TCC       1495
Ala Ala Tyr Ile Ala Gly Asp Ile Ala Tyr Val Ala Asp Lys Phe Ser
        745             750             755

CGC GGA CAC AAC CTA AAC ATC TAC ATG TTG GGT GCT GAC CAC CAT GGT       1543
Arg Gly His Asn Leu Asn Ile Tyr Met Leu Gly Ala Asp His His Gly
    760             765             770

TAC ATC GCG CGC CTG AAG GCA GCG GCG GCG GCA CTT GGC TAC AAG CCA       1591
Tyr Ile Ala Arg Leu Lys Ala Ala Ala Ala Ala Leu Gly Tyr Lys Pro
775             780             785             790

GAA GGC GTT GAA GTC CTG ATT GGC CAG ATG GTG AAC CTG CTT CGC GAC       1639
Glu Gly Val Glu Val Leu Ile Gly Gln Met Val Asn Leu Leu Arg Asp
                795             800             805

GGC AAG GCA GTG CGT ATG TCC AAG CGT GCA GGC ACC GTG GTC ACC CTA       1687
Gly Lys Ala Val Arg Met Ser Lys Arg Ala Gly Thr Val Val Thr Leu
            810             815             820

GAT GAC CTC GTT GAA GCA ATC GGC ATC GAT GCG GCG CGT TAC TCC CTG       1735
Asp Asp Leu Val Glu Ala Ile Gly Ile Asp Ala Ala Arg Tyr Ser Leu
        825             830             835

ATC CGT TCC TCC GTG GAT TCT TCC CTG GAT ATC GAT CTC GGC CTG TGG       1783
Ile Arg Ser Ser Val Asp Ser Ser Leu Asp Ile Asp Leu Gly Leu Trp
    840             845             850

GAA TCC CAG TCC TCC GAC AAC CCT GTG TAC TAC GTG CAG TAC GGA CAC       1831
Glu Ser Gln Ser Ser Asp Asn Pro Val Tyr Tyr Val Gln Tyr Gly His
855             860             865             870

GCT CGT CTG TGC TCC ATC GCG CGC AAG GCA GAG ACC TTG GGT GTC ACC       1879
Ala Arg Leu Cys Ser Ile Ala Arg Lys Ala Glu Thr Leu Gly Val Thr
                875             880             885

GAG GAA GGC GCA GAC CTA TCT CTA CTG ACC CAC GAC CGC GAA GGC GAT       1927
Glu Glu Gly Ala Asp Leu Ser Leu Leu Thr His Asp Arg Glu Gly Asp
            890             895             900

CTC ATC CGC ACA CTC GGA GAG TTC CCA GCA GTG GTG AAG GCT GCC GCT       1975
Leu Ile Arg Thr Leu Gly Glu Phe Pro Ala Val Val Lys Ala Ala Ala
        905             910             915

GAC CTA CGT GAA CCA CAC CGC ATT GCC CGC TAT GCT GAG GAA TTA GCT       2023
Asp Leu Arg Glu Pro His Arg Ile Ala Arg Tyr Ala Glu Glu Leu Ala
    920             925             930

GGA ACT TTC CAC CGC TTC TAC GAT TCC TGC CAC ATC CTT CCA AAG GTT       2071
Gly Thr Phe His Arg Phe Tyr Asp Ser Cys His Ile Leu Pro Lys Val
935             940             945             950

GAT GAG GAT ACG GCA CCA ATC CAC ACA GCA CGT CTG GCA CTT GCA GCA       2119
Asp Glu Asp Thr Ala Pro Ile His Thr Ala Arg Leu Ala Leu Ala Ala
                955             960             965

GCA ACC CGC CAG ACC CTC GCT AAC GCC CTG CAC CTG GTT GGC GTT TCC       2167
Ala Thr Arg Gln Thr Leu Ala Asn Ala Leu His Leu Val Gly Val Ser
            970             975             980

GCA CCG GAG AAG ATG TAACA ATG GCT ACA GTT GAA AAT TTC AAT GAA         2214
Ala Pro Glu Lys Met       Met Ala Thr Val Glu Asn Phe Asn Glu
        985                 1                   5

CTT CCC GCA CAC GTA TGG CCA CGC AAT GCC GTG CGC CAA GAA GAC GGC       2262
Leu Pro Ala His Val Trp Pro Arg Asn Ala Val Arg Gln Glu Asp Gly
 10             15              20              25

GTT GTC ACC GTC GCT GGT GTG CCT CTG CCT GAC CTC GCT GAA GAA TAC       2310
Val Val Thr Val Ala Gly Val Pro Leu Pro Asp Leu Ala Glu Glu Tyr
            30              35              40

GGA ACC CCA CTG TTC GTA GTC GAC GAG GAC GAT TTC CGT TCC CGC TGT       2358
Gly Thr Pro Leu Phe Val Val Asp Glu Asp Asp Phe Arg Ser Arg Cys
        45              50              55

CGC GAC ATG GCT ACC GCA TTC GGT GGA CCA GGC AAT GTG CAC TAC GCA       2406
```

|  |  |  |  |  |  |  |  |  |  |  |  |  |  |  |  |
|---|---|---|---|---|---|---|---|---|---|---|---|---|---|---|---|
| Arg | Asp | Met | Ala | Thr | Ala | Phe | Gly | Gly | Pro | Gly | Asn | Val | His | Tyr | Ala |
|  |  | 60 |  |  |  | 65 |  |  |  | 70 |  |  |  |  |  |

| TCT | AAA | GCG | TTC | CTG | ACC | AAG | ACC | ATT | GCA | CGT | TGG | GTT | GAT | GAA | GAG | 2454 |
|---|---|---|---|---|---|---|---|---|---|---|---|---|---|---|---|---|
| Ser | Lys | Ala | Phe | Leu | Thr | Lys | Thr | Ile | Ala | Arg | Trp | Val | Asp | Glu | Glu |  |
|  | 75 |  |  |  |  | 80 |  |  |  |  | 85 |  |  |  |  |  |

| GGG | CTG | GCA | CTG | GAC | ATT | GCA | TCC | ATC | AAC | GAA | CTG | GGC | ATT | GCC | CTG | 2502 |
|---|---|---|---|---|---|---|---|---|---|---|---|---|---|---|---|---|
| Gly | Leu | Ala | Leu | Asp | Ile | Ala | Ser | Ile | Asn | Glu | Leu | Gly | Ile | Ala | Leu |  |
| 90 |  |  |  |  | 95 |  |  |  |  | 100 |  |  |  |  | 105 |  |

| GCC | GCT | GGT | TTC | CCC | GCC | AGC | CGT | ATC | ACC | GCG | CAC | GGC | AAC | AAC | AAA | 2550 |
|---|---|---|---|---|---|---|---|---|---|---|---|---|---|---|---|---|
| Ala | Ala | Gly | Phe | Pro | Ala | Ser | Arg | Ile | Thr | Ala | His | Gly | Asn | Asn | Lys |  |
|  |  |  |  | 110 |  |  |  |  | 115 |  |  |  |  | 120 |  |  |

| GGC | GTA | GAG | TTC | CTG | CGC | GCG | TTG | GTT | CAA | AAC | GGT | GTG | GGA | CAC | GTG | 2598 |
|---|---|---|---|---|---|---|---|---|---|---|---|---|---|---|---|---|
| Gly | Val | Glu | Phe | Leu | Arg | Ala | Leu | Val | Gln | Asn | Gly | Val | Gly | His | Val |  |
|  |  |  |  | 125 |  |  |  |  | 130 |  |  |  |  | 135 |  |  |

| GTG | CTG | GAC | TCC | GCA | CAG | GAA | CTA | GAA | CTG | TTG | GAT | TAC | GTT | GCC | GCT | 2646 |
|---|---|---|---|---|---|---|---|---|---|---|---|---|---|---|---|---|
| Val | Leu | Asp | Ser | Ala | Gln | Glu | Leu | Glu | Leu | Leu | Asp | Tyr | Val | Ala | Ala |  |
|  |  | 140 |  |  |  |  | 145 |  |  |  |  | 150 |  |  |  |  |

| GGT | GAA | GGC | AAG | ATT | CAG | GAC | GTG | TTG | ATC | CGC | GTA | AAG | CCA | GGC | ATC | 2694 |
|---|---|---|---|---|---|---|---|---|---|---|---|---|---|---|---|---|
| Gly | Glu | Gly | Lys | Ile | Gln | Asp | Val | Leu | Ile | Arg | Val | Lys | Pro | Gly | Ile |  |
|  | 155 |  |  |  |  | 160 |  |  |  |  | 165 |  |  |  |  |  |

| GAA | GCA | CAC | ACC | CAC | GAG | TTC | ATC | GCC | ACT | AGC | CAC | GAA | GAC | CAG | AAG | 2742 |
|---|---|---|---|---|---|---|---|---|---|---|---|---|---|---|---|---|
| Glu | Ala | His | Thr | His | Glu | Phe | Ile | Ala | Thr | Ser | His | Glu | Asp | Gln | Lys |  |
| 170 |  |  |  |  | 175 |  |  |  |  | 180 |  |  |  |  | 185 |  |

| TTC | GGA | TTC | TCC | CTG | GCA | TCC | GGT | TCC | GCA | TTC | GAA | GCA | GCA | AAA | GCC | 2790 |
|---|---|---|---|---|---|---|---|---|---|---|---|---|---|---|---|---|
| Phe | Gly | Phe | Ser | Leu | Ala | Ser | Gly | Ser | Ala | Phe | Glu | Ala | Ala | Lys | Ala |  |
|  |  |  |  | 190 |  |  |  |  | 195 |  |  |  |  | 200 |  |  |

| GCC | AAC | AAC | GCA | GAA | AAC | CTG | AAC | CTG | GTT | GGC | CTG | CAC | TGC | CAC | GTT | 2838 |
|---|---|---|---|---|---|---|---|---|---|---|---|---|---|---|---|---|
| Ala | Asn | Asn | Ala | Glu | Asn | Leu | Asn | Leu | Val | Gly | Leu | His | Cys | His | Val |  |
|  |  |  | 205 |  |  |  |  | 210 |  |  |  |  | 215 |  |  |  |

| GGT | TCC | CAG | GTG | TTC | GAC | GCC | GAA | GGC | TTC | AAG | CTG | GCA | GCA | GAA | CGC | 2886 |
|---|---|---|---|---|---|---|---|---|---|---|---|---|---|---|---|---|
| Gly | Ser | Gln | Val | Phe | Asp | Ala | Glu | Gly | Phe | Lys | Leu | Ala | Ala | Glu | Arg |  |
|  |  | 220 |  |  |  |  | 225 |  |  |  |  | 230 |  |  |  |  |

| GTG | TTG | GGC | CTG | TAC | TCA | CAG | ATC | CAC | AGC | GAA | CTG | GGC | GTT | GCC | CTT | 2934 |
|---|---|---|---|---|---|---|---|---|---|---|---|---|---|---|---|---|
| Val | Leu | Gly | Leu | Tyr | Ser | Gln | Ile | His | Ser | Glu | Leu | Gly | Val | Ala | Leu |  |
|  | 235 |  |  |  |  | 240 |  |  |  |  | 245 |  |  |  |  |  |

| CCT | GAA | CTG | GAT | CTC | GGT | GGC | GGA | TAC | GGC | ATT | GCC | TAT | ACC | GCA | GCT | 2982 |
|---|---|---|---|---|---|---|---|---|---|---|---|---|---|---|---|---|
| Pro | Glu | Leu | Asp | Leu | Gly | Gly | Gly | Tyr | Gly | Ile | Ala | Tyr | Thr | Ala | Ala |  |
| 250 |  |  |  |  | 255 |  |  |  |  | 260 |  |  |  |  | 265 |  |

| GAA | GAA | CCA | CTC | AAC | GTC | GCA | GAA | GTT | GCC | TCC | GAC | CTG | CTC | ACC | GCA | 3030 |
|---|---|---|---|---|---|---|---|---|---|---|---|---|---|---|---|---|
| Glu | Glu | Pro | Leu | Asn | Val | Ala | Glu | Val | Ala | Ser | Asp | Leu | Leu | Thr | Ala |  |
|  |  |  |  | 270 |  |  |  |  | 275 |  |  |  |  | 280 |  |  |

| GTC | GGA | AAA | ATG | GCA | GCG | GAA | CTA | GGC | ATC | GAC | GCA | CCA | ACC | GTG | CTT | 3078 |
|---|---|---|---|---|---|---|---|---|---|---|---|---|---|---|---|---|
| Val | Gly | Lys | Met | Ala | Ala | Glu | Leu | Gly | Ile | Asp | Ala | Pro | Thr | Val | Leu |  |
|  |  |  | 285 |  |  |  |  | 290 |  |  |  |  | 295 |  |  |  |

| GTT | GAG | CCC | GGC | CGC | GCT | ATC | GCA | GGC | CCC | TCC | ACC | GTG | ACC | ATC | TAC | 3126 |
|---|---|---|---|---|---|---|---|---|---|---|---|---|---|---|---|---|
| Val | Glu | Pro | Gly | Arg | Ala | Ile | Ala | Gly | Pro | Ser | Thr | Val | Thr | Ile | Tyr |  |
|  |  | 300 |  |  |  |  | 305 |  |  |  |  | 310 |  |  |  |  |

| GAA | GTC | GGC | ACC | ACC | AAA | GAC | GTC | CAC | GTA | GAC | GAC | GAC | AAA | ACC | CGC | 3174 |
|---|---|---|---|---|---|---|---|---|---|---|---|---|---|---|---|---|
| Glu | Val | Gly | Thr | Thr | Lys | Asp | Val | His | Val | Asp | Asp | Asp | Lys | Thr | Arg |  |
|  | 315 |  |  |  |  | 320 |  |  |  |  | 325 |  |  |  |  |  |

| CGT | TAC | ATC | GCC | GTG | GAC | GGA | GGC | ATG | TCC | GAC | AAC | ATC | CGC | CCA | GCA | 3222 |
|---|---|---|---|---|---|---|---|---|---|---|---|---|---|---|---|---|
| Arg | Tyr | Ile | Ala | Val | Asp | Gly | Gly | Met | Ser | Asp | Asn | Ile | Arg | Pro | Ala |  |
| 330 |  |  |  |  | 335 |  |  |  |  | 340 |  |  |  |  | 345 |  |

| CTC | TAC | GGC | TCC | GAA | TAC | GAC | GCC | CGT | GTA | GTA | TCC | CGC | TTC | GCC | GAA | 3270 |
|---|---|---|---|---|---|---|---|---|---|---|---|---|---|---|---|---|
| Leu | Tyr | Gly | Ser | Glu | Tyr | Asp | Ala | Arg | Val | Val | Ser | Arg | Phe | Ala | Glu |  |
|  |  |  |  | 350 |  |  |  |  | 355 |  |  |  |  | 360 |  |  |

| GGA | GAC | CCA | GTA | AGC | ACC | CGC | ATC | GTG | GGC | TCC | CAC | TGC | GAA | TCC | GGC | 3318 |
|---|---|---|---|---|---|---|---|---|---|---|---|---|---|---|---|---|
| Gly | Asp | Pro | Val | Ser | Thr | Arg | Ile | Val | Gly | Ser | His | Cys | Glu | Ser | Gly |  |
|  |  |  | 365 |  |  |  |  | 370 |  |  |  |  | 375 |  |  |  |

| GAT | ATC | CTG | ATC | AAC | GAT | GAA | ATC | TAC | CCA | TCT | GAC | ATC | ACC | AGC | GGC | 3366 |
|---|---|---|---|---|---|---|---|---|---|---|---|---|---|---|---|---|

```
Asp Ile Leu Ile Asn Asp Glu Ile Tyr Pro Ser Asp Ile Thr Ser Gly
        380                 385                 390

GAC TTC CTT GCA CTC GCA GCC ACC GGC GCA TAC TGC TAC GCC ATG AGC          3414
Asp Phe Leu Ala Leu Ala Ala Thr Gly Ala Tyr Cys Tyr Ala Met Ser
    395                 400                 405

TCC CGC TAC AAC GCC TTC ACA CGG CCC GCC GTC GTG TCC GTC CGC GCT          3462
Ser Arg Tyr Asn Ala Phe Thr Arg Pro Ala Val Val Ser Val Arg Ala
410                 415                 420                 425

GGC AGC TCC CGC CTC ATG CTG CGC CGC GAA ACG CTC GAC GAC ATC CTC          3510
Gly Ser Ser Arg Leu Met Leu Arg Arg Glu Thr Leu Asp Asp Ile Leu
                430                 435                 440

TCA CTA GAG GCA TAACGCTTTT CGACGCCTGA CCCCGCCCTT CACCTTCGCC              3562
Ser Leu Glu Ala
            445

GTGGAGGGCG GTTTTGG                                                        3579

( 2 ) INFORMATION FOR SEQ ID NO:16:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "Synthetic DNA"

( i v ) ANTI-SENSE: NO ( x i ) SEQUENCE DESCRIPTION: SEQ ID NO:16:

GTCGACGGAT CGCAAATGGC AAC                                                  23

( 2 ) INFORMATION FOR SEQ ID NO:17:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:17:

GGATCCTTGA GCACCTTGCG CAG                                                  23

( 2 ) INFORMATION FOR SEQ ID NO:18:

( i ) SEQUENCE CHARACTERISTICS:
                ( A ) LENGTH: 1411 base pairs
                ( B ) TYPE: nucleic acid
                ( C ) STRANDEDNESS: double
                ( D ) TOPOLOGY: linear ( i i ) MOLECULE TYPE: DNA (genomic)

( i v ) ANTI-SENSE: NO ( v i ) ORIGINAL SOURCE:
                ( A ) ORGANISM: Brevibacterium lactofermentum
                ( B ) STRAIN: ATCC 13869

( i x ) FEATURE:
                ( A ) NAME/KEY: CDS
                ( B ) LOCATION: 311..1213

( x i ) SEQUENCE DESCRIPTION: SEQ ID NO:18:

CTCTCGATAT CGAGAGAGAA GCAGCGCCAC GGTTTTTCGG TGATTTTGAG ATTGAAACTT          60
```

```
TGGCAGACGG ATCGCAAATG GCAACAAGCC CGTATGTCAT GGACTTTTAA CGCAAAGCTC     120

ACACCCACGA GCTAAAAATT CATATAGTTA AGACAACATT TTTGGCTGTA AAGACAGCC      180

GTAAAAACCT CTTGCTCATG TCAATTGTTC TTATCGGAAT GTGGCTTGGG CGATTGTTAT     240

GCAAAGTTG  TTAGGTTTTT TGCGGGGTTG TTTAACCCCC AAATGAGGGA AGAAGGTAAC     300

CTTGAACTCT ATG AGC ACA GGT TTA ACA GCT AAG ACC GGA GTA GAG CAC        349
           Met Ser Thr Gly Leu Thr Ala Lys Thr Gly Val Glu His
                              450                 455

TTC GGC ACC GTT GGA GTA GCA ATG GTT ACT CCA TTC ACG GAA TCC GGA       397
Phe Gly Thr Val Gly Val Ala Met Val Thr Pro Phe Thr Glu Ser Gly
460                 465                 470

GAC ATC GAT ATC GCT GCT GGC CGC GAA GTC GCG GCT TAT TTG GTT GAT       445
Asp Ile Asp Ile Ala Ala Gly Arg Glu Val Ala Ala Tyr Leu Val Asp
475                 480                 485                 490

AAG GGC TTG GAT TCT TTG GTT CTC GCG GGC ACC ACT GGT GAA TCC CCA       493
Lys Gly Leu Asp Ser Leu Val Leu Ala Gly Thr Thr Gly Glu Ser Pro
                495                 500                 505

ACG ACA ACC GCC GCT GAA AAA CTA GAA CTG CTC AAG GCC GTT CGT GAG       541
Thr Thr Thr Ala Ala Glu Lys Leu Glu Leu Leu Lys Ala Val Arg Glu
510                 515                 520

GAA GTT GGG GAT CGG GCG AAC GTC ATC GCC GGT GTC GGA ACC AAC AAC       589
Glu Val Gly Asp Arg Ala Asn Val Ile Ala Gly Val Gly Thr Asn Asn
            525                 530                 535

ACG CGG ACA TCT GTG GAA CTT GCG GAA GCT GCT GCT TCT GCT GGC GCA       637
Thr Arg Thr Ser Val Glu Leu Ala Glu Ala Ala Ala Ser Ala Gly Ala
540                 545                 550

GAC GGC CTT TTA GTT GTA ACT CCT TAT TAC TCC AAG CCG AGC CAA GAG       685
Asp Gly Leu Leu Val Val Thr Pro Tyr Tyr Ser Lys Pro Ser Gln Glu
555                 560                 565                 570

GGA TTG CTG GCG CAC TTC GGT GCA ATT GCT GCA GCA ACA GAG GTT CCA       733
Gly Leu Leu Ala His Phe Gly Ala Ile Ala Ala Ala Thr Glu Val Pro
                575                 580                 585

ATT TGT CTC TAT GAC ATT CCT GGT CGG TCA GGT ATT CCA ATT GAG TCT       781
Ile Cys Leu Tyr Asp Ile Pro Gly Arg Ser Gly Ile Pro Ile Glu Ser
                590                 595                 600

GAT ACC ATG AGA CGC CTG AGT GAA TTA CCT ACG ATT TTG GCG GTC AAG       829
Asp Thr Met Arg Arg Leu Ser Glu Leu Pro Thr Ile Leu Ala Val Lys
            605                 610                 615

GAC GCC AAG GGT GAC CTC GTT GCA GCC ACG TCA TTG ATC AAA GAA ACG       877
Asp Ala Lys Gly Asp Leu Val Ala Ala Thr Ser Leu Ile Lys Glu Thr
        620                 625                 630

GGA CTT GCC TGG TAT TCA GGC GAT GAC CCA CTA AAC CTT GTT TGG CTT       925
Gly Leu Ala Trp Tyr Ser Gly Asp Asp Pro Leu Asn Leu Val Trp Leu
635                 640                 645                 650

GCT TTG GGC GGA TCA GGT TTC ATT TCC GTA ATT GGA CAT GCA GCC CCC       973
Ala Leu Gly Gly Ser Gly Phe Ile Ser Val Ile Gly His Ala Ala Pro
                655                 660                 665

ACA GCA TTA CGT GAG TTG TAC ACA AGC TTC GAG GAA GGC GAC CTC GTC      1021
Thr Ala Leu Arg Glu Leu Tyr Thr Ser Phe Glu Glu Gly Asp Leu Val
            670                 675                 680

CGT GCG CGG GAA ATC AAC GCC AAA CTA TCA CCG CTG GTA GCT GCC CAA      1069
Arg Ala Arg Glu Ile Asn Ala Lys Leu Ser Pro Leu Val Ala Ala Gln
        685                 690                 695

GGT CGC TTG GGT GGA GTC AGC TTG GCA AAA GCT GCT CTG CGT CTG CAG      1117
Gly Arg Leu Gly Gly Val Ser Leu Ala Lys Ala Ala Leu Arg Leu Gln
700                 705                 710

GGC ATC AAC GTA GGA GAT CCT CGA CTT CCA ATT ATG GCT CCA AAT GAG      1165
Gly Ile Asn Val Gly Asp Pro Arg Leu Pro Ile Met Ala Pro Asn Glu
715                 720                 725                 730
```

| CAG | GAA | CTT | GAG | GCT | CTC | CGA | GAA | GAC | ATG | AAA | AAA | GCT | GGA | GTT | CTA | 1213 |
| Gln | Glu | Leu | Glu | Ala | Leu | Arg | Glu | Asp | Met | Lys | Lys | Ala | Gly | Val | Leu | |
| | | | 735 | | | | | 740 | | | | | 745 | | | |

TAAATATGAA TGATTCCCGA AATCGCGGCC GGAAGGTTAC CCGCAAGGCG GCCCACCAGA 1273

AGCTGGTCAG GAAAACCATC TGGATACCCC TGTCTTTCAG GCACCAGATG CTTCCTCTAA 1333

CCAGAGCGCT GTAAAAGCTG AGACCGCCGG AAACGACAAT CGGGATGCTG CGCAAGGTGC 1393

TCAAGGATCC CAACATTC 1411

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: NO ( x i ) SEQUENCE DESCRIPTION: SEQ ID NO:19:

TCGCGAAGTA GCACCTGTCA CTT 23

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: YES ( x i ) SEQUENCE DESCRIPTION: SEQ ID NO:20:

ACGGAATTCA ATCTTACGGC C 21

( 2 ) INFORMATION FOR SEQ ID NO:21:

( i ) SEQUENCE CHARACTERISTICS:
        ( A ) LENGTH: 1643 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Brevibacterium lactofermentum
        ( B ) STRAIN: ATCC 13869

( x i ) SEQUENCE DESCRIPTION: SEQ ID NO:21:

TCGCGAAGTA GCACCTGTCA CTTTTGTCTC AAATATTAAA TCGAATATCA ATATACGGTC 60

TGTTTATTGG AACGCATCCC AGTGGCTGAG ACGCATCCGC TAAAGCCCCA GGAACCCTGT 120

GCAGAAAGAA AACACTCCTC TGGCTAGGTA GACACAGTTT ATAAAGGTAG AGTTGAGCGG 180

GTAACTGTCA GCACGTAGAT CGAAAGGTGC ACAAGGTGG CCCTGGTCGT ACAGAAATAT 240

GGCGGTTCCT CGCTTGAGAG TGCGGAACGC ATTAGAAACG TCGCTGAACG GATCGTTGCC 300

ACCAAGAAGG CTGGAAATGA TGTCGTGGTT GTCTGCTCCG CAATGGGAGA CACCACGGAT 360

| | | | | | |
|---|---|---|---|---|---|
| GAACTTCTAG | AACTTGCAGC | GGCAGTGAAT | CCCGTTCCGC | CAGCTCGTGA | AATGGATATG | 420
| CTCCTGACTG | CTGGTGAGCG | TATTTCTAAC | GCTCTCGTCG | CCATGGCTAT | TGAGTCCCTT | 480
| GGCGCAGAAG | CTCAATCTTT | CACTGGCTCT | CAGGCTGGTG | TGCTCACCAC | CGAGCGCCAC | 540
| GGAAACGCAC | GCATTGTTGA | CGTCACACCG | GGTCGTGTGC | GTGAAGCACT | CGATGAGGGC | 600
| AAGATCTGCA | TTGTTGCTGG | TTTTCAGGGT | GTTAATAAAG | AAACCCGCGA | TGTCACCACG | 660
| TTGGGTCGTG | GTGGTTCTGA | CACCACTGCA | GTTGCGTTGG | CAGCTGCTTT | GAACGCTGAT | 720
| GTGTGTGAGA | TTTACTCGGA | CGTTGACGGT | GTGTATACCG | CTGACCCGCG | CATCGTTCCT | 780
| AATGCACAGA | AGCTGGAAAA | GCTCAGCTTC | GAAGAAATGC | TGGAACTTGC | TGCTGTTGGC | 840
| TCCAAGATTT | TGGTGCTGCG | CAGTGTTGAA | TACGCTCGTG | CATTCAATGT | GCCACTTCGC | 900
| GTACGCTCGT | CTTATAGTAA | TGATCCCGGC | ACTTTGATTG | CCGGCTCTAT | GGAGGATATT | 960
| CCTGTGGAAG | AAGCAGTCCT | TACCGGTGTC | GCAACCGACA | AGTCCGAAGC | CAAAGTAACC | 1020
| GTTCTGGGTA | TTTCCGATAA | GCCAGGCGAG | GCTGCCAAGG | TTTTCCGTGC | GTTGGCTGAT | 1080
| GCAGAAATCA | ACATTGACAT | GGTTCTGCAG | AACGTCTCCT | CTGTGGAAGA | CGGCACCACC | 1140
| GACATCACGT | TCACCTGCCC | TCGCGCTGAC | GGACGCCGTG | CGATGGAGAT | CTTGAAGAAG | 1200
| CTTCAGGTTC | AGGGCAACTG | GACCAATGTG | CTTTACGACG | ACCAGGTCGG | CAAAGTCTCC | 1260
| CTCGTGGGTG | CTGGCATGAA | GTCTCACCCA | GGTGTTACCG | CAGAGTTCAT | GGAAGCTCTG | 1320
| CGCGATGTCA | ACGTGAACAT | CGAATTGATT | TCCACCTCTG | AGATCCGCAT | TTCCGTGCTG | 1380
| ATCCGTGAAG | ATGATCTGGA | TGCTGCTGCA | CGTGCATTGC | ATGAGCAGTT | CCAGCTGGGC | 1440
| GGCGAAGACG | AAGCCGTCGT | TTATGCAGGC | ACCGGACGCT | AAAGTTTTAA | AGGAGTAGTT | 1500
| TTACAATGAC | CACCATCGCA | GTTGTTGGTG | CAACCGGCCA | GGTCGGCCAG | GTTATGCGCA | 1560
| CCCTTTTGGA | AGAGCGCAAT | TTCCCAGCTG | ACACTGTTCG | TTTCTTTGCT | TCCCCGCGTT | 1620
| CCGCAGGCCG | TAAGATTGAA | TTC | | | | 1643

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: NO ( x i ) SEQUENCE DESCRIPTION: SEQ ID NO:22:

| | | |
|---|---|---|
| GGATCCCCAA | TCGATACCTG | GAA | 23

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: YES ( x i ) SEQUENCE DESCRIPTION: SEQ ID NO:23:

| | | |
|---|---|---|
| CGGTTCATCG | CCAAGTTTTT | CTT | 23

( 2 ) INFORMATION FOR SEQ ID NO:24:

( i ) SEQUENCE CHARACTERISTICS:
        ( A ) LENGTH: 2001 base pairs
        ( B ) TYPE: nucleic acid
        ( C ) STRANDEDNESS: double
        ( D ) TOPOLOGY: linear ( i i ) MOLECULE TYPE: DNA (genomic)

( i v ) ANTI-SENSE: NO ( v i ) ORIGINAL SOURCE:
        ( A ) ORGANISM: Brevibacterium lactofermentum
        ( B ) STRAIN: ATCC 13869

( i x ) FEATURE:
        ( A ) NAME/KEY: CDS
        ( B ) LOCATION: 730..1473

( x i ) SEQUENCE DESCRIPTION: SEQ ID NO:24:

```
GGATCCCCAA  TCGATACCTG  GAACGACAAC  CTGATCAGGA  TATCCAATGC  CTTGAATATT      60

GACGTTGAGG  AAGGAATCAC  CAGCCATCTC  AACTGGAAGA  CCTGACGCCT  GCTGAATTGG     120

ATCAGTGGCC  CAATCGACCC  ACCAACCAGG  TTGGCTATTA  CCGGCGATAT  CAAAAACAAC     180

TCGCGTGAAC  GTTTCGTGCT  CGGCAACGCG  GATGCCAGCG  ATCGACATAT  CGGAGTCACC     240

AACTTGAGCC  TGCTGCTTCT  GATCCATCGA  CGGGGAACCC  AACGGCGGCA  AAGCAGTGGG     300

GGAAGGGGAG  TTGGTGGACT  CTGAATCAGT  GGGCTCTGAA  GTGGTAGGCG  ACGGGGCAGC     360

ATCTGAAGGC  GTGCGAGTTG  TGGTGACCGG  GTTAGCGGTT  TCAGTTTCTG  TCACAACTGG     420

AGCAGGACTA  GCAGAGGTTG  TAGGCGTTGA  GCCGCTTCCA  TCACAAGCAC  TTAAAAGTAA     480

AGAGGCGGAA  ACCACAAGCG  CCAAGGAACT  ACCTGCGGAA  CGGGCGGTGA  AGGGCAACTT     540

AAGTCTCATA  TTTCAAACAT  AGTTCCACCT  GTGTGATTAA  TCTCCAGAAC  GGAACAAACT     600

GATGAACAAT  CGTTAACAAC  ACAGACCAAA  ACGGTCAGTT  AGGTATGGAT  ATCAGCACCT     660

TCTGAATGGG  TACGTCTAGA  CTGGTGGGCG  TTTGAAAAAC  TCTTCGCCCC  ACGAAAATGA     720

AGGAGCATA  ATG GGA ATC AAG GTT GGC GTT CTC GGA GCC AAA GGC CGT             768
           Met Gly Ile Lys Val Gly Val Leu Gly Ala Lys Gly Arg
                    305             310

GTT GGT CAA ACT ATT GTG GCA GCA GTC AAT GAG TCC GAC GAT CTG GAG            816
Val Gly Gln Thr Ile Val Ala Ala Val Asn Glu Ser Asp Asp Leu Glu
315             320             325                     330

CTT GTT GCA GAG ATC GGC GTC GAC GAT GAT TTG AGC CTT CTG GTA GAC            864
Leu Val Ala Glu Ile Gly Val Asp Asp Asp Leu Ser Leu Leu Val Asp
                335             340             345

AAC GGC GCT GAA GTT GTC GTT GAC TTC ACC ACT CCT AAC GCT GTG ATG            912
Asn Gly Ala Glu Val Val Val Asp Phe Thr Thr Pro Asn Ala Val Met
            350             355             360

GGC AAC CTG GAG TTC TGC ATC AAC AAC GGC ATT TCT GCG GTT GTT GGA            960
Gly Asn Leu Glu Phe Cys Ile Asn Asn Gly Ile Ser Ala Val Val Gly
        365             370             375

ACC ACG GGC TTC GAT GAT GCT CGT TTG GAG CAG GTT CGC GCC TGG CTT           1008
Thr Thr Gly Phe Asp Asp Ala Arg Leu Glu Gln Val Arg Ala Trp Leu
    380             385             390

GAA GGA AAA GAC AAT GTC GGT GTT CTG ATC GCA CCT AAC TTT GCT ATC           1056
Glu Gly Lys Asp Asn Val Gly Val Leu Ile Ala Pro Asn Phe Ala Ile
395             400             405             410

TCT GCG GTG TTG ACC ATG GTC TTT TCC AAG CAG GCT GCC CGC TTC TTC           1104
Ser Ala Val Leu Thr Met Val Phe Ser Lys Gln Ala Ala Arg Phe Phe
            415             420             425

GAA TCA GCT GAA GTT ATT GAG CTG CAC CAC CCC AAC AAG CTG GAT GCA           1152
```

|  |  |  |  |  |  |  |  |  |  |  |  |  |  |  |
|---|---|---|---|---|---|---|---|---|---|---|---|---|---|---|
| Glu | Ser | Ala | Glu | Val | Ile | Glu | Leu | His | His | Pro | Asn | Lys | Leu | Asp | Ala |
|  |  |  | 430 |  |  |  |  | 435 |  |  |  |  | 440 |  |  |

| CCT | TCA | GGC | ACC | GCG | ATC | CAC | ACT | GCT | CAG | GGC | ATT | GCT | GCG | GCA | CGC | 1200 |
|---|---|---|---|---|---|---|---|---|---|---|---|---|---|---|---|---|
| Pro | Ser | Gly | Thr | Ala | Ile | His | Thr | Ala | Gln | Gly | Ile | Ala | Ala | Ala | Arg |  |
|  |  | 445 |  |  |  |  | 450 |  |  |  |  | 455 |  |  |  |  |

| AAA | GAA | GCA | GGC | ATG | GAC | GCA | CAG | CCA | GAT | GCG | ACC | GAG | CAG | GCA | CTT | 1248 |
|---|---|---|---|---|---|---|---|---|---|---|---|---|---|---|---|---|
| Lys | Glu | Ala | Gly | Met | Asp | Ala | Gln | Pro | Asp | Ala | Thr | Glu | Gln | Ala | Leu |  |
|  | 460 |  |  |  |  | 465 |  |  |  |  | 470 |  |  |  |  |  |

| GAG | GGT | TCC | CGT | GGC | GCA | AGC | GTA | GAT | GGA | ATC | CCA | GTT | CAC | GCA | GTC | 1296 |
|---|---|---|---|---|---|---|---|---|---|---|---|---|---|---|---|---|
| Glu | Gly | Ser | Arg | Gly | Ala | Ser | Val | Asp | Gly | Ile | Pro | Val | His | Ala | Val |  |
| 475 |  |  |  |  | 480 |  |  |  |  | 485 |  |  |  |  | 490 |  |

| CGC | ATG | TCC | GGC | ATG | GTT | GCT | CAC | GAG | CAA | GTT | ATC | TTT | GGC | ACC | CAG | 1344 |
|---|---|---|---|---|---|---|---|---|---|---|---|---|---|---|---|---|
| Arg | Met | Ser | Gly | Met | Val | Ala | His | Glu | Gln | Val | Ile | Phe | Gly | Thr | Gln |  |
|  |  |  |  | 495 |  |  |  |  | 500 |  |  |  |  | 505 |  |  |

| GGT | CAG | ACC | TTG | ACC | ATC | AAG | CAG | GAC | TCC | TAT | GAT | CGC | AAC | TCA | TTT | 1392 |
|---|---|---|---|---|---|---|---|---|---|---|---|---|---|---|---|---|
| Gly | Gln | Thr | Leu | Thr | Ile | Lys | Gln | Asp | Ser | Tyr | Asp | Arg | Asn | Ser | Phe |  |
|  |  |  | 510 |  |  |  |  | 515 |  |  |  |  | 520 |  |  |  |

| GCA | CCA | GGT | GTC | TTG | GTG | GGT | GTG | CGC | AAC | ATT | GCA | CAG | CAC | CCA | GGC | 1440 |
|---|---|---|---|---|---|---|---|---|---|---|---|---|---|---|---|---|
| Ala | Pro | Gly | Val | Leu | Val | Gly | Val | Arg | Asn | Ile | Ala | Gln | His | Pro | Gly |  |
|  |  | 525 |  |  |  |  | 530 |  |  |  |  | 535 |  |  |  |  |

| CTA | GTC | GTA | GGA | CTT | GAG | CAT | TAC | CTA | GGC | CTG | TAAAGGCTCA | TTTCAGCAGC | 1493 |
|---|---|---|---|---|---|---|---|---|---|---|---|---|---|
| Leu | Val | Val | Gly | Leu | Glu | His | Tyr | Leu | Gly | Leu |  |  |  |
|  | 540 |  |  |  |  | 545 |  |  |  |  |  |  |  |

| GGGTGGAATT | TTTTAAAAGG | AGCGTTTAAA | GGCTGTGGCC | GAACAAGTTA | AATTGAGCGT | 1553 |
|---|---|---|---|---|---|---|
| GGAGTTGATA | GCGTGCAGTT | CTTTTACTCC | ACCCGCTGAT | GTTGAGTGGT | CAACTGATGT | 1613 |
| TGAGGGCGCG | GAAGCACTCG | TCGAGTTTGC | GGGTCGTGCC | TGCTACGAAA | CTTTTGATAA | 1673 |
| GCCGAACCCT | CGAACTGCTT | CCAATGCTGC | GTATCTGCGC | CACATCATGG | AAGTGGGGCA | 1733 |
| CACTGCTTTG | CTTGAGCATG | CCAATGCCAC | GATGTATATC | CGAGGCATTT | CTCGGTCCGC | 1793 |
| GACCCATGAA | TTGGTCCGAC | ACCGCCATTT | TTCCTTCTCT | CAACTGTCTC | AGCGTTTCGT | 1853 |
| GCACAGCGGA | GAATCGGAAG | TAGTGGTGCC | CACTCTCATC | GATGAAGATC | CGCAGTTGCG | 1913 |
| TGAACTTTTC | ATGCACGCCA | TGGATGAGTC | TCGGTTCGCT | TCAATGAGC | TGCTTAATGC | 1973 |
| GCTGGAAGAA | AAACTTGGCG | ATGAACCG |  |  |  | 2001 |

( 2 ) INFORMATION FOR SEQ ID NO:25:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: NO ( x i ) SEQUENCE DESCRIPTION: SEQ ID NO:25:

CCGGACAGCT CACCCACAAA ATCAATGCAC TCTAAAAGG TACCT     45

( 2 ) INFORMATION FOR SEQ ID NO:26:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: YES ( x i ) SEQUENCE DESCRIPTION: SEQ ID NO:26:

CTAGAGGTAC CTTTTTAGAG TGCATTGATT TTGTGGGTGA GCTGT                45

( 2 ) INFORMATION FOR SEQ ID NO:27:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: NO ( x i ) SEQUENCE DESCRIPTION: SEQ ID NO:27:

CTAGCTCGAG ATATCAGATC TACTAGTCGA CCGC                34

( 2 ) INFORMATION FOR SEQ ID NO:28:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i v ) ANTI-SENSE: YES ( x i ) SEQUENCE DESCRIPTION: SEQ ID NO:28:

GGTCGACTAG TAGATCTGAT ATCTCGAG                28

( 2 ) INFORMATION FOR SEQ ID NO:29:

( i ) SEQUENCE CHARACTERISTICS:
        ( A ) LENGTH: 550 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Met  Thr  Pro  Ala  Asp  Leu  Ala  Thr  Leu  Ile  Lys  Glu  Thr  Ala  Val  Glu
1              5                        10                       15

Val  Leu  Thr  Ser  Arg  Glu  Leu  Asp  Thr  Ser  Val  Leu  Pro  Glu  Gln  Val
              20                       25                       30

Val  Val  Glu  Arg  Pro  Arg  Asn  Pro  Glu  His  Gly  Asp  Tyr  Ala  Thr  Asn
          35                       40                       45

Ile  Ala  Leu  Gln  Val  Ala  Lys  Lys  Val  Gly  Gln  Asn  Pro  Arg  Asp  Leu
     50                       55                       60

Ala  Thr  Trp  Leu  Ala  Glu  Ala  Leu  Ala  Ala  Asp  Asp  Ala  Ile  Asp  Ser
65                       70                       75                       80

Ala  Glu  Ile  Ala  Gly  Pro  Gly  Phe  Leu  Asn  Ile  Arg  Leu  Ala  Ala  Ala
                    85                       90                       95

Ala  Gln  Gly  Glu  Ile  Val  Ala  Lys  Ile  Leu  Ala  Gln  Gly  Glu  Thr  Phe
               100                      105                      110

Gly  Asn  Ser  Asp  His  Leu  Ser  His  Leu  Asp  Val  Asn  Leu  Glu  Phe  Val
               115                      120                      125

Ser  Ala  Asn  Pro  Thr  Gly  Pro  Ile  His  Leu  Gly  Gly  Thr  Arg  Trp  Ala
          130                      135                      140
```

```
Ala Val Gly Asp Ser Leu Gly Arg Val Leu Glu Ala Ser Gly Ala Lys
145                 150                 155                 160

Val Thr Arg Glu Tyr Tyr Phe Asn Asp His Gly Arg Gln Ile Asp Arg
            165                 170                 175

Phe Ala Leu Ser Leu Leu Ala Ala Ala Lys Gly Glu Pro Thr Pro Glu
            180                 185                 190

Asp Gly Tyr Gly Gly Glu Tyr Ile Lys Glu Ile Ala Glu Ala Ile Val
            195                 200                 205

Glu Lys His Pro Glu Ala Leu Ala Leu Glu Pro Ala Ala Thr Gln Glu
210                 215                 220

Leu Phe Arg Ala Glu Gly Val Glu Met Met Phe Glu His Ile Lys Ser
225                 230                 235                 240

Ser Leu His Glu Phe Gly Thr Asp Phe Asp Val Tyr Tyr His Glu Asn
            245                 250                 255

Ser Leu Phe Glu Ser Gly Ala Val Asp Lys Ala Val Gln Val Leu Lys
            260                 265                 270

Asp Asn Gly Asn Leu Tyr Glu Asn Glu Gly Ala Trp Trp Leu Arg Ser
            275                 280                 285

Thr Glu Phe Gly Asp Asp Lys Asp Arg Val Val Ile Lys Ser Asp Gly
    290                 295                 300

Asp Ala Ala Tyr Ile Ala Gly Asp Ile Ala Tyr Val Ala Asp Lys Phe
305                 310                 315                 320

Ser Arg Gly His Asn Leu Asn Ile Tyr Met Leu Gly Ala Asp His His
                325                 330                 335

Gly Tyr Ile Ala Arg Leu Lys Ala Ala Ala Ala Leu Gly Tyr Lys
                340             345                 350

Pro Glu Gly Val Glu Val Leu Ile Gly Gln Met Val Asn Leu Leu Arg
        355                 360                 365

Asp Gly Lys Ala Val Arg Met Ser Lys Arg Ala Gly Thr Val Val Thr
    370                 375                 380

Leu Asp Asp Leu Val Glu Ala Ile Gly Ile Asp Ala Ala Arg Tyr Ser
385                 390                 395                 400

Leu Ile Arg Ser Ser Val Asp Ser Ser Leu Asp Ile Asp Leu Gly Leu
            405                 410                 415

Trp Glu Ser Gln Ser Ser Asp Asn Pro Val Tyr Tyr Val Gln Tyr Gly
            420                 425                 430

His Ala Arg Leu Cys Ser Ile Ala Arg Lys Ala Glu Thr Leu Gly Val
            435                 440                 445

Thr Glu Glu Gly Ala Asp Leu Ser Leu Leu Thr His Asp Arg Glu Gly
    450                 455                 460

Asp Leu Ile Arg Thr Leu Gly Glu Phe Pro Ala Val Val Lys Ala Ala
465                 470                 475                 480

Ala Asp Leu Arg Glu Pro His Arg Ile Ala Arg Tyr Ala Glu Glu Leu
            485                 490                 495

Ala Gly Thr Phe His Arg Phe Tyr Asp Ser Cys His Ile Leu Pro Lys
            500                 505                 510

Val Asp Glu Asp Thr Ala Pro Ile His Thr Ala Arg Leu Ala Leu Ala
            515                 520                 525

Ala Ala Thr Arg Gln Thr Leu Ala Asn Ala Leu His Leu Val Gly Val
    530                 535                 540

Ser Ala Pro Glu Lys Met
545                 550
```

( 2 ) INFORMATION FOR SEQ ID NO:30:

( i ) SEQUENCE CHARACTERISTICS:
        ( A ) LENGTH: 445 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:30:

```
Met Ala Thr Val Glu Asn Phe Asn Glu Leu Pro Ala His Val Trp Pro
 1               5                  10                  15
Arg Asn Ala Val Arg Gln Glu Asp Gly Val Val Thr Val Ala Gly Val
            20                  25                  30
Pro Leu Pro Asp Leu Ala Glu Tyr Gly Thr Pro Leu Phe Val Val
        35                  40                  45
Asp Glu Asp Asp Phe Arg Ser Arg Cys Arg Asp Met Ala Thr Ala Phe
    50                  55                  60
Gly Gly Pro Gly Asn Val His Tyr Ala Ser Lys Ala Phe Leu Thr Lys
65                  70                  75                  80
Thr Ile Ala Arg Trp Val Asp Glu Glu Gly Leu Ala Leu Asp Ile Ala
                85                  90                  95
Ser Ile Asn Glu Leu Gly Ile Ala Leu Ala Ala Gly Phe Pro Ala Ser
                100                 105                 110
Arg Ile Thr Ala His Gly Asn Asn Lys Gly Val Glu Phe Leu Arg Ala
            115                 120                 125
Leu Val Gln Asn Gly Val Gly His Val Val Leu Asp Ser Ala Gln Glu
        130                 135                 140
Leu Glu Leu Leu Asp Tyr Val Ala Ala Gly Glu Gly Lys Ile Gln Asp
145                 150                 155                 160
Val Leu Ile Arg Val Lys Pro Gly Ile Glu Ala His Thr His Glu Phe
                165                 170                 175
Ile Ala Thr Ser His Glu Asp Gln Lys Phe Gly Phe Ser Leu Ala Ser
                180                 185                 190
Gly Ser Ala Phe Glu Ala Ala Lys Ala Ala Asn Asn Ala Glu Asn Leu
            195                 200                 205
Asn Leu Val Gly Leu His Cys His Val Gly Ser Gln Val Phe Asp Ala
        210                 215                 220
Glu Gly Phe Lys Leu Ala Ala Glu Arg Val Leu Gly Leu Tyr Ser Gln
225                 230                 235                 240
Ile His Ser Glu Leu Gly Val Ala Leu Pro Glu Leu Asp Leu Gly Gly
                245                 250                 255
Gly Tyr Gly Ile Ala Tyr Thr Ala Glu Glu Pro Leu Asn Val Ala
                260                 265                 270
Glu Val Ala Ser Asp Leu Leu Thr Ala Val Gly Lys Met Ala Ala Glu
            275                 280                 285
Leu Gly Ile Asp Ala Pro Thr Val Leu Val Glu Pro Gly Arg Ala Ile
        290                 295                 300
Ala Gly Pro Ser Thr Val Thr Ile Tyr Glu Val Gly Thr Thr Lys Asp
305                 310                 315                 320
Val His Val Asp Asp Asp Lys Thr Arg Arg Tyr Ile Ala Val Asp Gly
                325                 330                 335
Gly Met Ser Asp Asn Ile Arg Pro Ala Leu Tyr Gly Ser Glu Tyr Asp
                340                 345                 350
Ala Arg Val Val Ser Arg Phe Ala Glu Gly Asp Pro Val Ser Thr Arg
            355                 360                 365
```

| | | | | | | | | | | | | | | |
|---|---|---|---|---|---|---|---|---|---|---|---|---|---|---|
|Ile|Val|Gly|Ser|His|Cys|Glu|Ser|Gly|Asp|Ile|Leu|Ile|Asn|Asp|Glu|
|   |   |370|   |   |   |375|   |   |   |380|   |   |   |   |   |
|Ile|Tyr|Pro|Ser|Asp|Ile|Thr|Ser|Gly|Asp|Phe|Leu|Ala|Leu|Ala|Ala|
|385|   |   |   |   |390|   |   |   |   |395|   |   |   |   |400|
|Thr|Gly|Ala|Tyr|Cys|Tyr|Ala|Met|Ser|Ser|Arg|Tyr|Asn|Ala|Phe|Thr|
|   |   |   |   |405|   |   |   |   |410|   |   |   |   |415|   |
|Arg|Pro|Ala|Val|Val|Ser|Val|Arg|Ala|Gly|Ser|Ser|Arg|Leu|Met|Leu|
|   |   |   |420|   |   |   |   |425|   |   |   |   |430|   |   |
|Arg|Arg|Glu|Thr|Leu|Asp|Asp|Ile|Leu|Ser|Leu|Glu|Ala|   |   |   |
|   |   |435|   |   |   |   |440|   |   |   |   |445|   |   |   |

(2) INFORMATION FOR SEQ ID NO:31:

(i) SEQUENCE CHARACTERISTICS:
    (A) LENGTH: 301 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:31:

| | | | | | | | | | | | | | | |
|---|---|---|---|---|---|---|---|---|---|---|---|---|---|---|
|Met|Ser|Thr|Gly|Leu|Thr|Ala|Lys|Thr|Gly|Val|Glu|His|Phe|Gly|Thr|
|1|   |   |   |5|   |   |   |   |10|   |   |   |   |15|   |
|Val|Gly|Val|Ala|Met|Val|Thr|Pro|Phe|Thr|Glu|Ser|Gly|Asp|Ile|Asp|
|   |   |   |20|   |   |   |   |25|   |   |   |   |30|   |   |
|Ile|Ala|Ala|Gly|Arg|Glu|Val|Ala|Ala|Tyr|Leu|Val|Asp|Lys|Gly|Leu|
|   |   |35|   |   |   |   |40|   |   |   |   |45|   |   |   |
|Asp|Ser|Leu|Val|Leu|Ala|Gly|Thr|Thr|Gly|Glu|Ser|Pro|Thr|Thr|Thr|
|   |50|   |   |   |   |55|   |   |   |   |60|   |   |   |   |
|Ala|Ala|Glu|Lys|Leu|Glu|Leu|Leu|Lys|Ala|Val|Arg|Glu|Glu|Val|Gly|
|65|   |   |   |   |70|   |   |   |   |75|   |   |   |   |80|
|Asp|Arg|Ala|Asn|Val|Ile|Ala|Gly|Val|Gly|Thr|Asn|Asn|Thr|Arg|Thr|
|   |   |   |   |85|   |   |   |   |90|   |   |   |   |95|   |
|Ser|Val|Glu|Leu|Ala|Glu|Ala|Ala|Ala|Ser|Ala|Gly|Ala|Asp|Gly|Leu|
|   |   |   |100|   |   |   |   |105|   |   |   |   |110|   |   |
|Leu|Val|Val|Thr|Pro|Tyr|Tyr|Ser|Lys|Pro|Ser|Gln|Glu|Gly|Leu|Leu|
|   |   |115|   |   |   |   |120|   |   |   |   |125|   |   |   |
|Ala|His|Phe|Gly|Ala|Ile|Ala|Ala|Ala|Thr|Glu|Val|Pro|Ile|Cys|Leu|
|   |130|   |   |   |   |135|   |   |   |   |140|   |   |   |   |
|Tyr|Asp|Ile|Pro|Gly|Arg|Ser|Gly|Ile|Pro|Ile|Glu|Ser|Asp|Thr|Met|
|145|   |   |   |   |150|   |   |   |   |155|   |   |   |   |160|
|Arg|Arg|Leu|Ser|Glu|Leu|Pro|Thr|Ile|Leu|Ala|Val|Lys|Asp|Ala|Lys|
|   |   |   |   |165|   |   |   |   |170|   |   |   |   |175|   |
|Gly|Asp|Leu|Val|Ala|Ala|Thr|Ser|Leu|Ile|Lys|Glu|Thr|Gly|Leu|Ala|
|   |   |   |180|   |   |   |   |185|   |   |   |   |190|   |   |
|Trp|Tyr|Ser|Gly|Asp|Asp|Pro|Leu|Asn|Leu|Val|Trp|Leu|Ala|Leu|Gly|
|   |   |195|   |   |   |   |200|   |   |   |   |205|   |   |   |
|Gly|Ser|Gly|Phe|Ile|Ser|Val|Ile|Gly|His|Ala|Ala|Pro|Thr|Ala|Leu|
|   |210|   |   |   |   |215|   |   |   |   |220|   |   |   |   |
|Arg|Glu|Leu|Tyr|Thr|Ser|Phe|Glu|Glu|Gly|Asp|Leu|Val|Arg|Ala|Arg|
|225|   |   |   |   |230|   |   |   |   |235|   |   |   |   |240|
|Glu|Ile|Asn|Ala|Lys|Leu|Ser|Pro|Leu|Val|Ala|Ala|Gln|Gly|Arg|Leu|
|   |   |   |   |245|   |   |   |   |250|   |   |   |   |255|   |
|Gly|Gly|Val|Ser|Leu|Ala|Lys|Ala|Ala|Leu|Arg|Leu|Gln|Gly|Ile|Asn|
|   |   |   |260|   |   |   |   |265|   |   |   |   |270|   |   |

-continued

```
Val  Gly  Asp  Pro  Arg  Leu  Pro  Ile  Met  Ala  Pro  Asn  Glu  Gln  Glu  Leu
          275                      280                    285

Glu  Ala  Leu  Arg  Glu  Asp  Met  Lys  Lys  Ala  Gly  Val  Leu
     290                      295                    300
```

( 2 ) INFORMATION FOR SEQ ID NO:32:

( i ) SEQUENCE CHARACTERISTICS:
 ( A ) LENGTH: 248 amino acids
 ( B ) TYPE: amino acid
 ( C ) STRANDEDNESS: single
 ( D ) TOPOLOGY: linear ( i i ) MOLECULE TYPE: protein ( x i ) SEQUENCE DESCRIPTION: SEQ ID NO:32:

```
Met  Gly  Ile  Lys  Val  Gly  Val  Leu  Gly  Ala  Lys  Gly  Arg  Val  Gly  Gln
1              5                        10                       15

Thr  Ile  Val  Ala  Ala  Val  Asn  Glu  Ser  Asp  Asp  Leu  Glu  Leu  Val  Ala
               20                  25                       30

Glu  Ile  Gly  Val  Asp  Asp  Asp  Leu  Ser  Leu  Leu  Val  Asp  Asn  Gly  Ala
          35                   40                       45

Glu  Val  Val  Val  Asp  Phe  Thr  Thr  Pro  Asn  Ala  Val  Met  Gly  Asn  Leu
     50                        55                   60

Glu  Phe  Cys  Ile  Asn  Asn  Gly  Ile  Ser  Ala  Val  Val  Gly  Thr  Thr  Gly
65                       70                  75                            80

Phe  Asp  Asp  Ala  Arg  Leu  Glu  Gln  Val  Arg  Ala  Trp  Leu  Glu  Gly  Lys
                    85                       90                            95

Asp  Asn  Val  Gly  Val  Leu  Ile  Ala  Pro  Asn  Phe  Ala  Ile  Ser  Ala  Val
               100                 105                      110

Leu  Thr  Met  Val  Phe  Ser  Lys  Gln  Ala  Ala  Arg  Phe  Phe  Glu  Ser  Ala
          115                      120                      125

Glu  Val  Ile  Glu  Leu  His  His  Pro  Asn  Lys  Leu  Asp  Ala  Pro  Ser  Gly
     130                      135                      140

Thr  Ala  Ile  His  Thr  Ala  Gln  Gly  Ile  Ala  Ala  Ala  Arg  Lys  Glu  Ala
145                           150                 155                      160

Gly  Met  Asp  Ala  Gln  Pro  Asp  Ala  Thr  Glu  Gln  Ala  Leu  Glu  Gly  Ser
                    165                      170                      175

Arg  Gly  Ala  Ser  Val  Asp  Gly  Ile  Pro  Val  His  Ala  Val  Arg  Met  Ser
               180                 185                      190

Gly  Met  Val  Ala  His  Glu  Gln  Val  Ile  Phe  Gly  Thr  Gln  Gly  Gln  Thr
          195                      200                      205

Leu  Thr  Ile  Lys  Gln  Asp  Ser  Tyr  Asp  Arg  Asn  Ser  Phe  Ala  Pro  Gly
     210                      215                      220

Val  Leu  Val  Gly  Val  Arg  Asn  Ile  Ala  Gln  His  Pro  Gly  Leu  Val  Val
225                      230                      235                      240

Gly  Leu  Glu  His  Tyr  Leu  Gly  Leu
                    245
```